US010197652B2

(12) United States Patent
Hürlimann et al.

(10) Patent No.: US 10,197,652 B2
(45) Date of Patent: Feb. 5, 2019

(54) METHOD AND SYSTEM FOR APPLYING NMR PULSE SEQUENCES WITH INTERACTING SHELLS

(71) Applicant: SCHLUMBERGER TECHNOLOGY CORPORATION, Houston, TX (US)

(72) Inventors: Martin D. Hürlimann, Newton, MA (US); Yi-Qiao Song, Newton, MA (US); Soumyajit Mandal, Cambridge, MA (US)

(*) Notice: Subject to any disclaimer, the term of this patent is extended or adjusted under 35 U.S.C. 154(b) by 1314 days.

(21) Appl. No.: 13/774,425

(22) Filed: Feb. 22, 2013

(65) Prior Publication Data
US 2013/0234704 A1 Sep. 12, 2013

Related U.S. Application Data

(60) Provisional application No. 61/608,457, filed on Mar. 8, 2012.

(51) Int. Cl.
G01R 33/46 (2006.01)
G01R 33/28 (2006.01)
G01V 3/32 (2006.01)
G01N 24/08 (2006.01)
G01R 33/44 (2006.01)
G01R 33/36 (2006.01)
G01R 33/38 (2006.01)

(52) U.S. Cl.
CPC ........... *G01R 33/46* (2013.01); *G01N 24/081* (2013.01); *G01R 33/28* (2013.01); *G01R 33/445* (2013.01); *G01V 3/32* (2013.01); *G01R 33/3621* (2013.01); *G01R 33/3808* (2013.01)

(58) Field of Classification Search
CPC ...... G01R 33/46; G01R 33/28; G01R 33/445; G01R 33/3621; G01R 33/3808; G01N 24/081; G01V 3/32
See application file for complete search history.

(56) References Cited

U.S. PATENT DOCUMENTS

| 5,433,196 A | 7/1995 | Fiat |
| 5,629,623 A | 5/1997 | Sezginer et al. |
| 6,031,422 A | 2/2000 | Ideler |

(Continued)

FOREIGN PATENT DOCUMENTS

KR 20100051411 A 5/2010

OTHER PUBLICATIONS

Brill et al., "Nonresonant Multiple Spin Echoes", Jul. 19, 2002, Science, vol. 297, pp. 369-372.*

(Continued)

*Primary Examiner* — Dixomara Vargas

(57) ABSTRACT

A method and system for determining a nuclear magnetic resonance (NMR) property are described herein. The method includes applying a static magnetic field to a substance and applying an NMR pulse sequence to the substance. The NMR pulse sequence comprises a first pulse sequence segment applied at a first frequency to a shell and a second pulse sequence segment applied at a second frequency. The first pulse sequence segment generates a resonant signal in the shell and the second pulse sequence segment generates a characteristic within the resonant signal. The resonant signal is detected and an NMR property is determined using the characteristic within the detected resonant signal.

24 Claims, 29 Drawing Sheets

(56) References Cited

U.S. PATENT DOCUMENTS

| | | | | |
|---|---|---|---|---|
| 6,133,735 | A * | 10/2000 | Hurlimann | G01N 24/081 324/300 |
| 6,441,613 | B1 * | 8/2002 | Rosenfeld | G01R 33/446 324/307 |
| 6,615,069 | B1 * | 9/2003 | Komura | G01R 33/4804 324/315 |
| 6,956,371 | B2 * | 10/2005 | Prammer | G01V 3/32 324/300 |
| 6,963,769 | B1 * | 11/2005 | Balaban | A61B 5/055 324/307 |
| 6,972,564 | B2 * | 12/2005 | Chen | G01N 24/081 324/303 |
| 7,375,520 | B2 * | 5/2008 | Nezafat | G01R 33/5635 324/307 |
| 7,501,819 | B2 * | 3/2009 | Ong | G01F 1/716 324/306 |
| 7,777,493 | B2 * | 8/2010 | Desvaux | G01R 33/3628 324/318 |
| 7,949,384 | B2 * | 5/2011 | Lewin | G01R 33/022 324/306 |
| 8,558,547 | B2 * | 10/2013 | Sacolick | G01R 33/246 324/309 |
| 8,704,522 | B2 * | 4/2014 | Akita | G01R 33/3692 324/318 |
| 9,069,998 | B2 * | 6/2015 | Bulumulla | G06K 9/00 |
| 9,709,511 | B2 * | 7/2017 | Lee | G01N 23/02 |
| 2006/0255799 | A1 | 11/2006 | Reiderman | |
| 2006/0272786 | A1 | 12/2006 | Svedman et al. | |
| 2011/0241667 | A1 * | 10/2011 | Blumich | G01N 24/08 324/303 |
| 2012/0001629 | A1 | 1/2012 | Hopper et al. | |
| 2012/0280683 | A1 * | 11/2012 | Sacolick | G01R 33/5612 324/309 |
| 2013/0234705 | A1 | 9/2013 | Mandal et al. | |
| 2013/0234706 | A1 | 9/2013 | Mandal et al. | |

OTHER PUBLICATIONS

Lepaisant et al., "Low- noise preamplifier with input and feedback transformers for low source resistance sensors." Review of Scientific Instruments 63.3 (1992): 2089-2094.

Hopper et al. "Low-frequency NMR with a non-resonant circuit." Journal of Magnetic Resonance 210.1 (2011): 69-74.

Office Action issued in U.S. Appl. No. 13/774,487 dated Oct. 19, 2016. 14 pages.

Office Action issued in U.S. Appl. No. 13/774,457 dated Mar. 9, 2017. 16 pages.

Basse-Lusebrink, et al., "Fast CPMG-based Bloch-Siegert B1+ mapping", Magnetic Resonance in Medicine, vol. 67 (2), 2011, pp. 405-418.

Bloch, et al., "Magnetic Resonance for Nonrotating Fields", Phys. Rev., vol. 57 (6), 1940, pp. 522-527.

Emsley, et al., "Phase Shifts Induced by Transient Bloch-Siegert Effects in NMR", Chemical Physics Letters, vol. 168 (3,4), 1990, pp. 297-303.

Hurlimann, et al., "Spin dynamics of Carr-Purcell-Meiboom-Gill-like sequences in grossly inhomogeneous B0 and B1 fields and application to NMR well logging", Journal of Magnetic Resonance, vol. 143 (1), 2000, pp. 120-135.

Sacolick, et al., "B1 mapping by Bloch-Siegert shift", Magnetic Resonance in Medicine, vol. 62 (5), 2010, pp. 1315-1322.

Sacolick, et al., "Fast radiofrequency flip angle calibration by Bloch—Siegert shift", Magnetic Resonance in Medicine, vol. 66 (5), 2011, pp. 1333-1338.

Chandler, et al., "Improved Log Quality With a Dual-Frequency Pulsed NMR Tool", SPE 28365—SPE Annual Technical Conference and Exhibition, New Orleans, Louisiana, Sep. 25-28, 1994, 13 pages.

Prammer, et al., "A New Multiband Generation of NMR Logging Tools", SPE 69670—SPE Reservoir Evaluation & Engineering, vol. 4 (1), 2001, pp. 59-63.

Depavia, et al., "A Next-Generation Wireline NMR Logging Tool", SPE 84482—SPE Annual Technical Conference and Exhibition, Denver Colorado, Oct. 5-8, 2003, 7 pages.

Heaton, et al., "Applications of a New-Generation NMR Wireline Logging Tool", SPE 77400—SPE Annual Technical Conference and Exhibition, San Antonio, Texas, 2002, 10 pages.

Chen, et al., "MR Explorer Log Acquisition Methods: Petrophysical-Objective-Oriented Approaches", SPWLA 44th Annual Logging Symposium, Galveston, Texas, Jun. 22-25, 2003, 13 pages.

Khamatdinov, et al., "Field Test of a New Nuclear Magnetic Resonance Tool", SPWLA 44th Annual Logging Symposium, Glaveston, Texas, Jun. 22-25, 2003, 12 pages.

Prammer, et al., "Directional Resonance: New Applications for MRIL", SPE 84479—SPE Annual Technical Conference and Exhibition, Denver, Colorado, Oct. 5-8, 2003, 9 pages.

Hurlimann, et al., "Quantitative Measurement of Two-Dimensional Distribution Functions of Diffusion and Relaxation in Grossly Inhomogeneous Fields", Journal of Magnetic Resonance vol. 157 (1), 2002, pp. 31-42.

English Translation of Examination Report issued in Saudi Arabia patent application 113340365 dated Jan. 4, 1438 H [2017]. 5 pages.

* cited by examiner

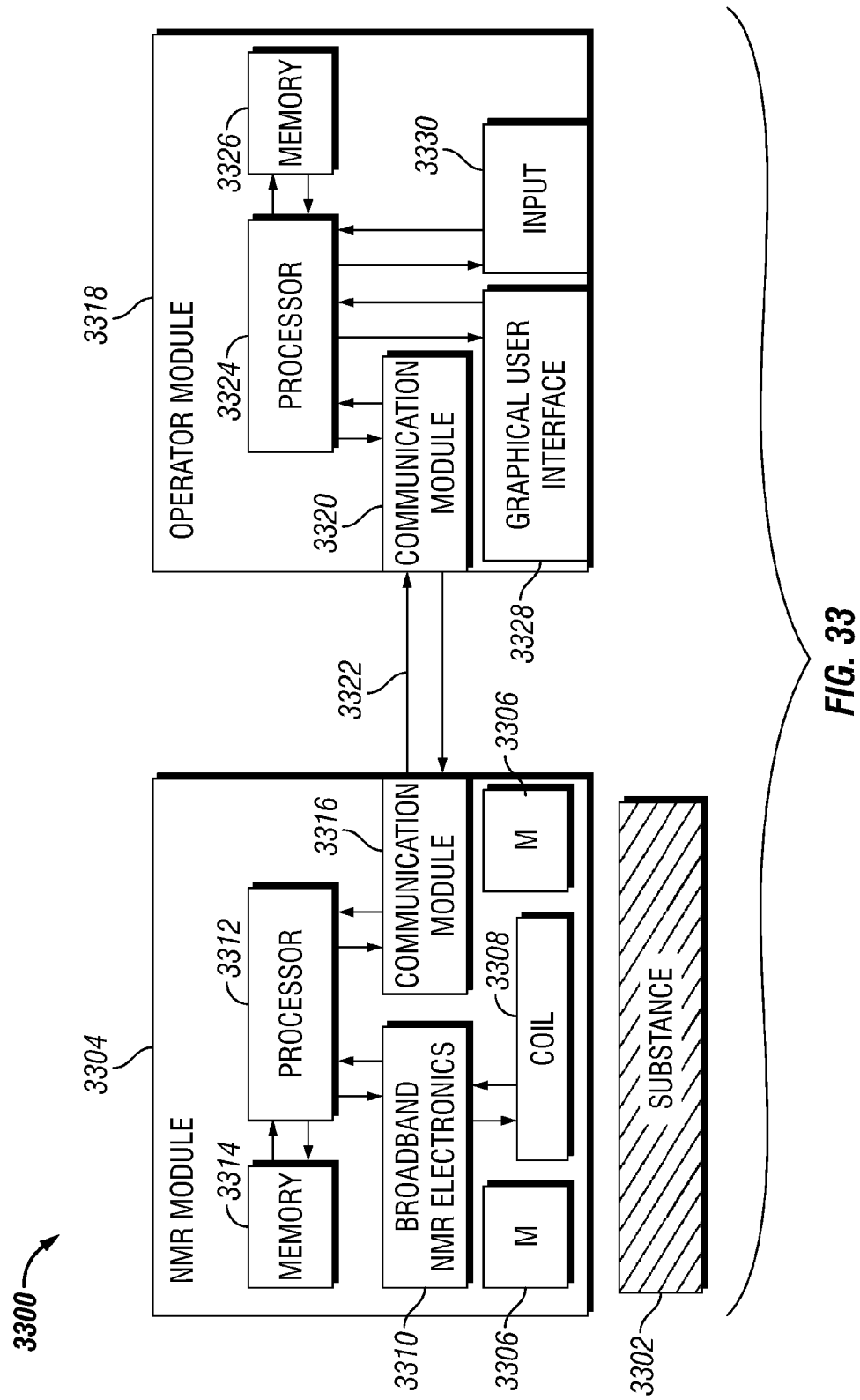

METHOD AND SYSTEM FOR APPLYING NMR PULSE SEQUENCES WITH INTERACTING SHELLS

CROSS-REFERENCE TO RELATED APPLICATIONS

This application claims the benefit of U.S. Patent Application Ser. No. 61/608,457 filed Mar. 8, 2012, which is incorporated herein by reference in its entirety. This application is also related to U.S. patent application Ser. No. 13/774,457 filed Feb. 22, 2013, entitled, "Method and System for Applying NMR Pulse Sequences Using Different Frequencies."

TECHNICAL FIELD

This disclosure relates to nuclear magnetic resonance (NMR) and, more particularly, to using nuclear magnetic resonance (NMR) to determine NMR properties.

BACKGROUND

Nuclear magnetic resonance (NMR) can be used to determine properties of a substance. An NMR procedure typically includes applying a static magnetic field to the substance. The static magnetic field generates an initial magnetization of atomic nuclei within the substance. Then, an NMR system is used to apply an oscillating magnetic field at a particular frequency to the substance. The oscillating field is composed of a sequence of pulses that tip the magnetization of the atomic nuclei away from the initial magnetization. The sequence of pulses can be arranged so that pulses and the static field interact with the nuclei to produce a resonant signal composed of "echoes" within at least a portion of the substance. The portion of the substance where the resonant signal is generated is known as a "shell."

The resonant signal is detected and then used to determine NMR properties such as $T_1$ relaxation time, $T_2$ relaxation time and attenuation of the signal due to molecular diffusion. These NMR properties can be used to determine the properties of the substance within the shell.

The pulse sequence is typically repeated a number of times so that the resonant signal can be more accurately determined. The next pulse sequence is not initiated until the atomic nuclei within the shell reach thermal equilibrium and are aligned with the initial magnetization. In some cases, it may take several seconds (e.g., 10 seconds) for the shell to reach thermal equilibrium. This means that the NMR system sits idle while the shell reaches thermal equilibrium.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a method for determining a nuclear magnetic resonance (NMR) property. The method includes applying a static magnetic field to a substance and applying an NMR pulse sequence to the substance. The NMR pulse sequence includes a first pulse sequence segment applied at a first frequency to a shell and a second pulse sequence segment applied at a second frequency. The first pulse sequence segment generates a resonant signal in the shell and the second pulse sequence segment generates a characteristic within the resonant signal. The resonant signal is detected and an NMR property is determined using the characteristic within the detected resonant signal.

In some embodiments, the NMR property is a property of the substance being measured. In other embodiments, the NMR property is a property of the NMR measurement itself.

Various embodiments of the present disclosure are also directed to a system for determining a nuclear magnetic resonance (NMR) property. The system includes a coil for applying a NMR pulse sequence to a substance and detecting a resonant signal within the substance. The system also includes a NMR transmitter with a non-resonant NMR transmitter circuit electronically coupled to the coil and a NMR receiver that receives resonant signals generated within the substance and detected at the coil. The system further includes a processor and a memory that stores instructions executable by the processor to perform processes. These processes include providing the NMR pulse sequence to the NMR transmitter. The NMR pulse sequence includes a first pulse sequence segment for application at a first frequency to a shell and a second pulse sequence segment for application at a second frequency. The first pulse sequence segment generates a resonant signal in the shell and the second pulse sequence segment generates a characteristic within the resonant signal. The processes also include determining an NMR property using the characteristic within the detected resonant signal.

Exemplary embodiments of the present disclosure are further directed to a method for determining an NMR property of a substance. The method includes applying a static magnetic field to the substance. Also, the method includes applying a first NMR pulse sequence to a first shell within the substance and applying a second NMR pulse sequence to a second shell within the substance. The first pulse sequence generates a resonant signal in the first shell and the second pulse sequence generates a characteristic within the resonant signal. The resonant signal is detected and the NMR property of the substance is determined using the characteristic within the detected resonant signal.

BRIEF DESCRIPTION OF THE DRAWINGS

Further features and advantages will become more readily apparent from the following detailed description when taken in conjunction with the accompanying drawings:

FIG. 33 shows a broadband NMR system for applying multi-segment sequences to a substance in accordance with one embodiment of the present disclosure;

DETAILED DESCRIPTION

Illustrative embodiments of the present disclosure are directed to a method for determining a nuclear magnetic resonance (NMR) property. The method includes applying a static magnetic field to a substance and applying an NMR pulse sequence to the substance. The NMR pulse sequence comprises a first pulse sequence segment applied at a first frequency to a shell and a second pulse sequence segment applied at a second frequency. The first pulse sequence segment generates a resonant signal in the shell and the second pulse sequence segment generates a characteristic within the resonant signal. The resonant signal is detected and an NMR property, such as $T_1$ relaxation time, is determined using the characteristic within the detected resonant signal. Details of various pulses sequences and systems for implementing the sequences are discussed below.

Figure 1:
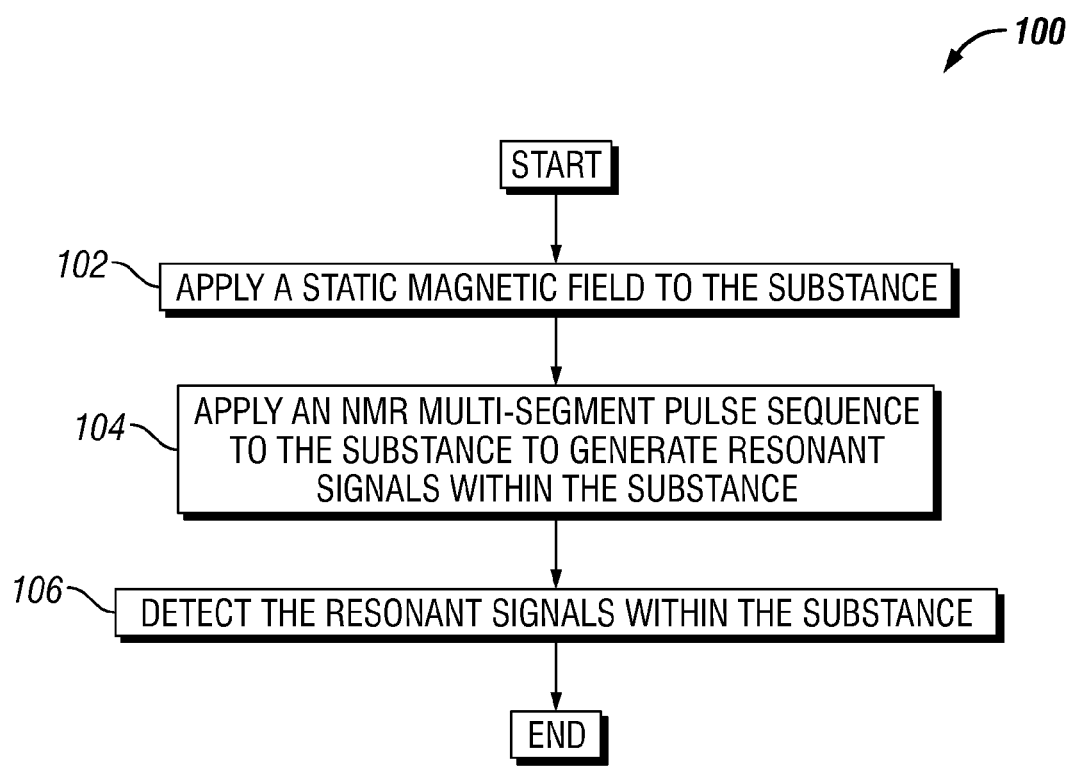
FIG. 1 shows a method of applying an NMR pulse sequence in accordance with one embodiment of the present disclosure.

FIG. 1 shows a method 100 of applying an NMR pulse sequence with multiple segments in accordance with one embodiment of the present disclosure. The method 100 includes applying a static magnetic field ($B_0$) to an area of interest within a substance 102, such as a reservoir formation containing hydrocarbons. In some embodiments, an inhomogeneous magnetic field is applied to the substance. The term "inhomogeneous" should be considered in the context of the NMR art. Many NMR well logging tools deploy inhomogeneous static magnetic fields due to the limitations and constraints of a borehole environment. In this context, an inhomogeneous static magnetic field is a static magnetic field that varies in intensity or direction within an area of interest of the substance. In one example, an inhomogeneous static magnetic field within a shell may vary in intensity by a value approximately equal to or greater than a nominal RF magnetic field ($B_1$) amplitude of an NMR pulse sequence applied to the area of interest. The inhomogeneous static field variation within a shell will be proportional to the intensity of $B_1$. For example, with rectangular pulses the variation is approximately $2B_1$. As $B_1$ increases the shell becomes thicker, so more variation in the static field occurs within the shell.

Figure 2:
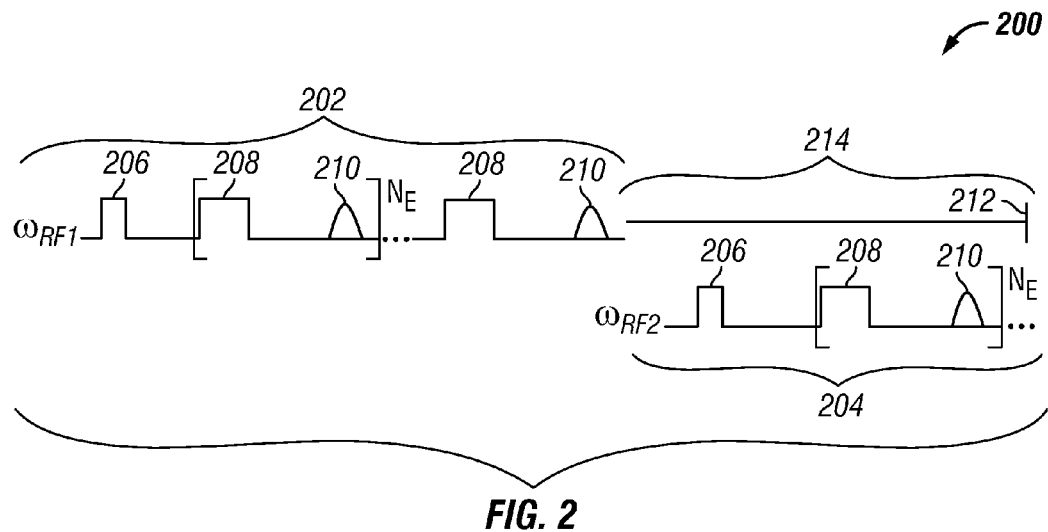
FIG. 2 shows an NMR pulse sequence with multiple pulse sequence segments in accordance with one embodiment of the present disclosure.

Once the static magnetic field is applied to the area of interest, the method includes applying an NMR pulse sequence to the area of interest within the substance 104. In some embodiments, the NMR pulse sequence is a series of radio frequency (RF) pulses. FIG. 2 shows an NMR pulse sequence 200 with multiple pulse sequence segments in accordance with one embodiment of the present disclosure. The NMR pulse sequence 200 includes at least a first pulse sequence segment 202 and a second pulse sequence segment 204. Each segment includes an excitation pulse 206, a series of refocusing pulses 208, and a series of echoes 210. In various embodiments, the excitation pulses have a length of $T_{90}$ and the refocusing pulses have a length of $T_{180}$. $T_{90}$ is defined as: $T_{90} = \pi/2(\gamma \times B_1)$, where $\gamma$ is the gyromagnetic ratio of a nucleus of interest and $B_1$ is the maximum amplitude of an applied circularly-polarized magnetic field in a rotating frame within the area of interest within the substance (e.g., in many cases, $B_1$ is half the amplitude of the linearly-polarized magnetic field produced by a coil). $T_{180}$ is defined as: $T_{180} = \pi/(\gamma \times B_1)$. The pulses also have amplitudes that typically range between 1 G (Gauss) and 10 G. In one specific example, the sequence segments 202, 204 are Carr, Purcell, Meiboom and Gill (CPMG) sequences. In various other embodiments, the sequence segments 202, 204 can be spin echo, inversion recovery, saturation recovery, and/or stimulated echo sequences. Illustrative embodiments of the present disclosure, however, are not limited to such specific sequences, pulse lengths, and amplitudes.

As shown in FIG. 2, the first segment 202 is applied to the substance at a first set of frequencies ($\omega_{RF1}$) and the second segment 204 is applied to the substance at a second set of frequencies ($\omega_{RF2}$). An average of the first set of frequencies and an average of the second frequencies are different by a value of $\Delta\omega_{RF}$. In some embodiments, the frequency difference ($\Delta\omega_{RF}$) is as great as 10% of the average of the first set of frequencies. In various other embodiments, the frequency difference can be even greater (e.g., 20%, 30%, or 50%). In a specific example, the frequency of a first pulse segment is approximately 1 MHz and the next segment is applied at 0.5 MHz or 0.75 MHz (e.g., $\Delta\omega_{RF}/2\pi = 0.5$ MHz or 0.25 MHz). In another specific example, the frequency difference is sufficient to switch between the resonant frequencies of hydrogen nuclei ($^1$H, or protons) and sodium nuclei ($^{23}$Na). The hydrogen nuclei and sodium nuclei can be different by as much as a factor of four.

The term "set" of frequencies is used because the frequency within a pulse segment or a single pulse may not be a single frequency. The frequency within a pulse sequence segment or a single pulse can vary over a set of frequencies (e.g., over a range of frequencies). In some embodiments, the frequency may be specifically selected to vary within a pulse sequence segment or a single pulse. Furthermore, resonant signals generated within a shell can also vary over a set of frequencies. Reference within the present disclosure to a specific frequency should not be interpreted as limited to that specific frequency because that frequency may vary within a pulse sequence segment or even a single pulse.

The NMR pulse sequence 200 applied to the substance generates resonant signals within the substance. The resonant signals are composed of a series of echoes. The first pulse sequence segment 202 will generate a first resonant signal in a first shell, while the second pulse sequence segment 204 will create a second resonant signal within a second shell. A "shell" is a region of the substance that produces a resonant signal in response to an NMR pulse sequence applied with a particular set of frequencies. In a homogenous static magnetic field, the shell will be broad across an area of interest within the substance because the field ($B_0$) is constant. In an inhomogeneous static magnetic field, the field changes across the area of interest and NMR pulse sequences at a particular frequency produce resonant signals in a limited region within area of interest. This limited region is referred to herein as a "shell" or a "slice."

Figure 3:
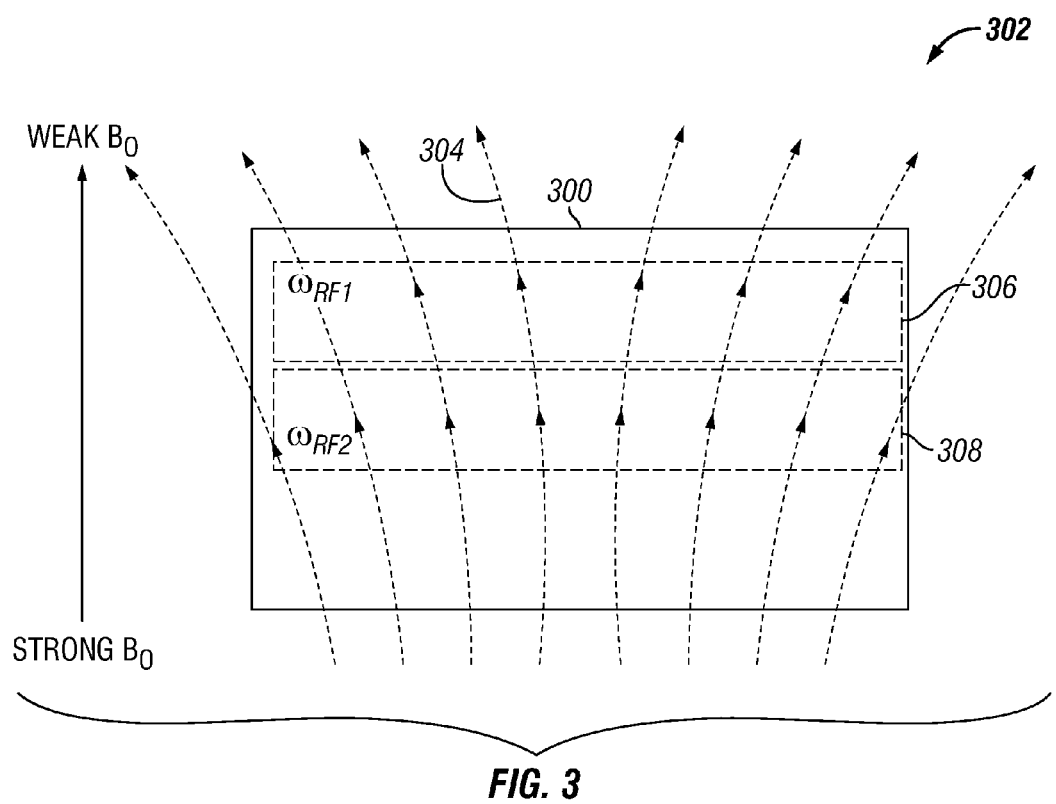
FIG. 3 shows an area of interest within a substance in accordance with one embodiment of the present disclosure.

FIG. 3 shows an area of interest 300 within a substance 302 in accordance with one embodiment of the present disclosure. In FIG. 3, an inhomogeneous magnetic field 304 is applied to the area of interest 300 within the substance 302. When the first pulse sequence segment 202 and the second pulse sequence segment 204 are applied to the area of interest 300 within the substance 302, the substance generates two resonant signals with two different frequencies (e.g., sets of frequencies). The first resonant signal originates at a first shell 306 and a second resonant signal originates at a second shell 308 within the area of interest 300. The two resonant signals have different frequencies because the static magnetic field 304 is different at each location within the area of interest 300 of the substance 302. The frequency of each signal can be determined using the following equation:

$$\omega_0 = \gamma \times B_0 \qquad \text{Eq. 1}$$

where $B_0$ is the strength of the static magnetic field 304, $\gamma$ is the gyromagnetic ratio of the atomic nuclei of interest, and $\omega_0$ is the frequency of the resonant signal that is produced by the atomic nuclei. The frequency of the resonant signals is also known as the Larmor frequency. For a hydrogen nucleus, the gyromagnetic ratio is 4258 Hz/Gauss. Given the relationship defined in Equation 1, if a static magnetic field of 235 Gauss is applied to the nucleus, the frequency of the resulting signal would be 1 MHz.

NMR pulse sequences are typically applied a number of times to a single shell within the substance (e.g., N=10, N=100, or N=1000) to improve the accuracy of the measurement. Conventional NMR systems typically do not apply a second NMR pulse sequence to the shell immediately after a first NMR pulse sequence. Instead, conventional systems sit idle until the shell reaches thermal equilibrium. Conventional wisdom suggests that applying a second NMR sequence before the shell reaches thermal equilibrium may produce inaccuracies in the second measurement. In some cases, conventional systems sit idle for several $T_1$ time constants before resuming application of NMR sequences. For example, if the substance of interest includes light oil, the idle time can be as great as 10 seconds. This idle time increases measurement time, which is costly in NMR borehole logging applications and also decreases the SNR available per unit time.

Illustrative embodiments of the present disclosure initiate the second pulse sequence segment 204 before the first shell 306 reaches thermal equilibrium. In this manner, various embodiments speed up NMR measurements and improve SNR. As shown in FIG. 2, the first pulse sequence segment 202 includes a refocusing pulse 208 and a corresponding echo 210 that are repeated a number of times (e.g., $N_E = 10$, $N_E$=100, $N_E$=1000) to form a series (e.g., train) of refocusing pulses and corresponding echoes. Once the first pulse sequence segment 202 is complete, the first shell 306 will reach a point of thermal equilibrium 212 during a time period 214. Before this point of thermal equilibrium 212, the second pulse sequence 204 segment is initiated and applied to the second shell 308. The term "thermal equilibrium" should be considered in the context of the NMR art. Many NMR logging tools do not apply a subsequent pulse sequence to a shell until most of the nuclei of interest within the shell are aligned with the initial magnetization induced by the static magnetic field. The approach to thermal equilibrium is exponential. The approach can be written as $M(t)=M(0)e^{-t/T1}+M(\infty)(1-e^{-t/T1})$, where $M(0)$ and $M(\infty)$ are the initial magnetization and thermal equilibrium magnetization, respectively, and t=0 corresponds to the end of the first pulse sequence segment 202. For practical purposes this infinitely long process is assumed to have completed once the term $e^{-t/T1}$ becomes very small (e.g., t is much greater than $T_1$). In one example, a shell is assumed to reach thermal equilibrium over a time period (e.g., 214) that is five times $T_1$, resulting in $e^{-t/T1}$=0.00674. The time period begins when the prior pulse sequence (e.g., 202) is completed. In another specific example, the time period (e.g., 214) is less than five times $T_1$ (e.g., four times $T_1$).

In accordance with the method 100 shown in FIG. 1, the first resonant signal generated at the first shell 306 and/or the second resonant signal generated at the second shell 308 are detected. These detected signals can be used to determine NMR properties for the substance 302 (e.g., $T_1$ relaxation time, $T_2$ relaxation time, diffusion, and/or a correlation function of such properties). In turn, the NMR properties can be used to determine physical properties of the substance, such as the chemical composition of the substance and/or the presence of a solid phase, a liquid phase, and/or a gas phase within the substance.

Figure 4:
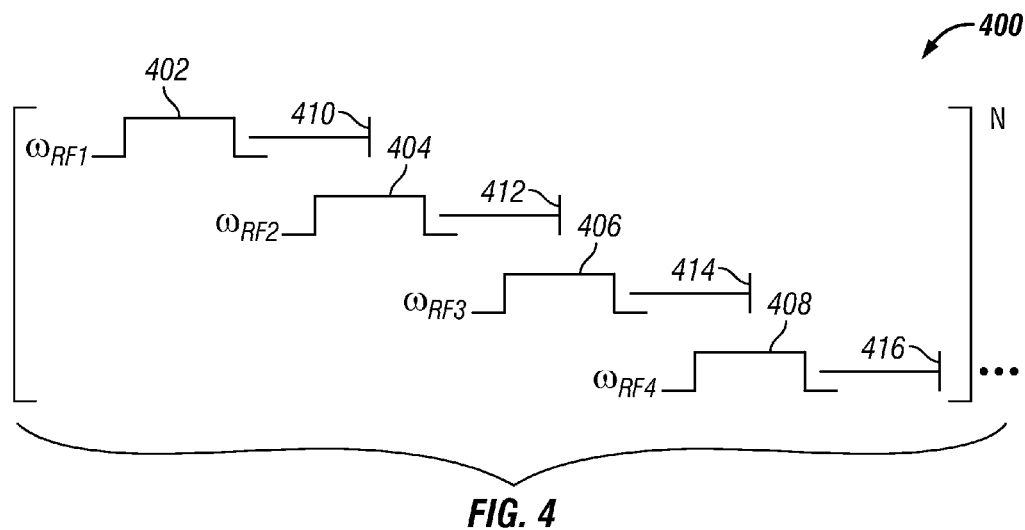
FIG. 4 shows an NMR pulse sequence with multiple pulse sequence segments in accordance with another embodiment of the present disclosure.
Figure 5:
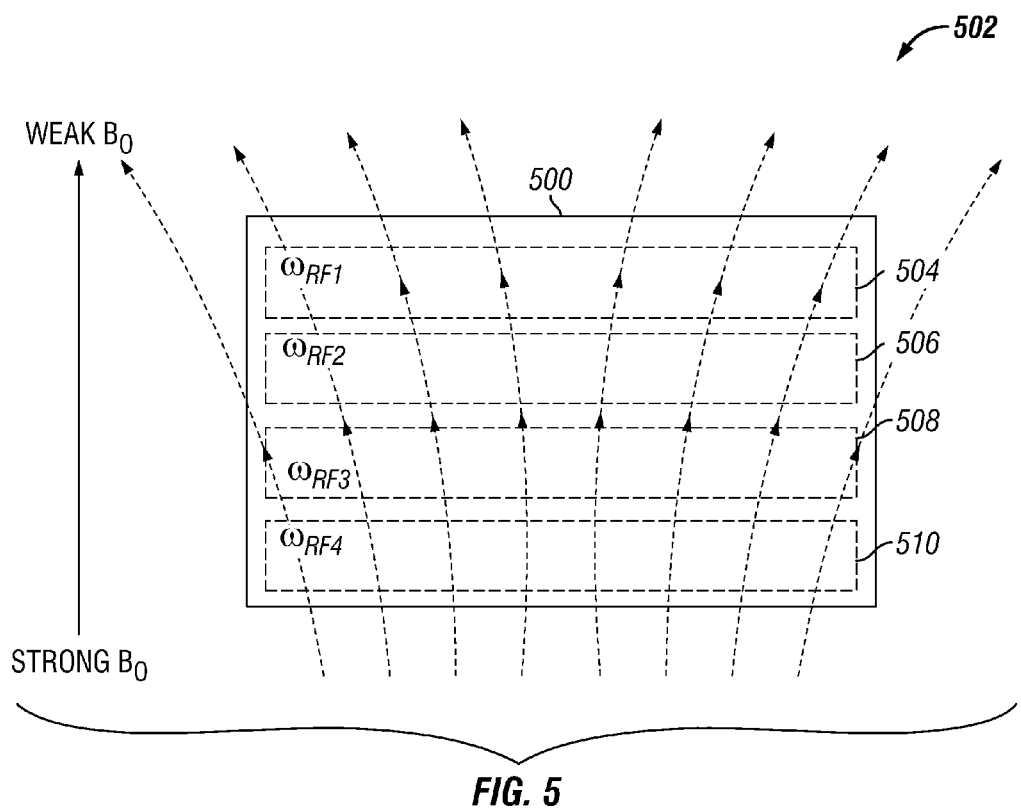
FIG. 5 shows four shells generated by a four-segment NMR pulse sequence in accordance with another embodiment of the present disclosure.

FIG. 4 shows an NMR pulse sequence 400 with multiple pulse sequence segments in accordance with another embodiment of the present disclosure. In FIG. 4, the NMR pulse sequence 400 includes four pulse sequence segments. A first segment 402 is applied to the substance with a first set of frequencies ($\omega_{RF1}$), a second segment 404 is applied to the substance with a second set of frequencies ($\omega_{RF2}$), a third segment 406 is applied to the substance with a third set of frequencies ($\omega_{RF3}$), and a fourth segment 408 is applied to the substance with a fourth set of frequencies ($\omega_{RF4}$). These frequencies are substantially similar to the average Larmor frequency of each shell in order to satisfy the resonance condition ($\omega_0=\omega_{RF}$) within each shell. FIG. 5 shows four shells 504, 506, 508, 510 generated by the four-segment NMR pulse sequence 400 within an area of interest 500 of the substance 502. In this case, an inhomogeneous static magnetic field is applied to the area of interest 500.

As shown in FIG. 4, the second segment 404 is initiated before the first shell 504 reaches a point of thermal equilibrium 410. The third segment 406 is initiated before the second shell 506 reaches a point of thermal equilibrium 412. The fourth segment 408 is initiated before the third shell 508 reaches a point of thermal equilibrium 414. At this point, in some embodiments, the NMR measurement stops. In various other embodiments, the NMR pulse sequence is repeated a number of times (N) and the first segment 402 is initiated before the fourth shell 510 reaches a point of thermal equilibrium 416.

Illustrative embodiments of the present disclosure are not limited to two, three or four pulse sequence segments.

Exemplary embodiments of the NMR pulse sequences may include five, six, nine, or more such pulse sequence segments.

Figure 6:
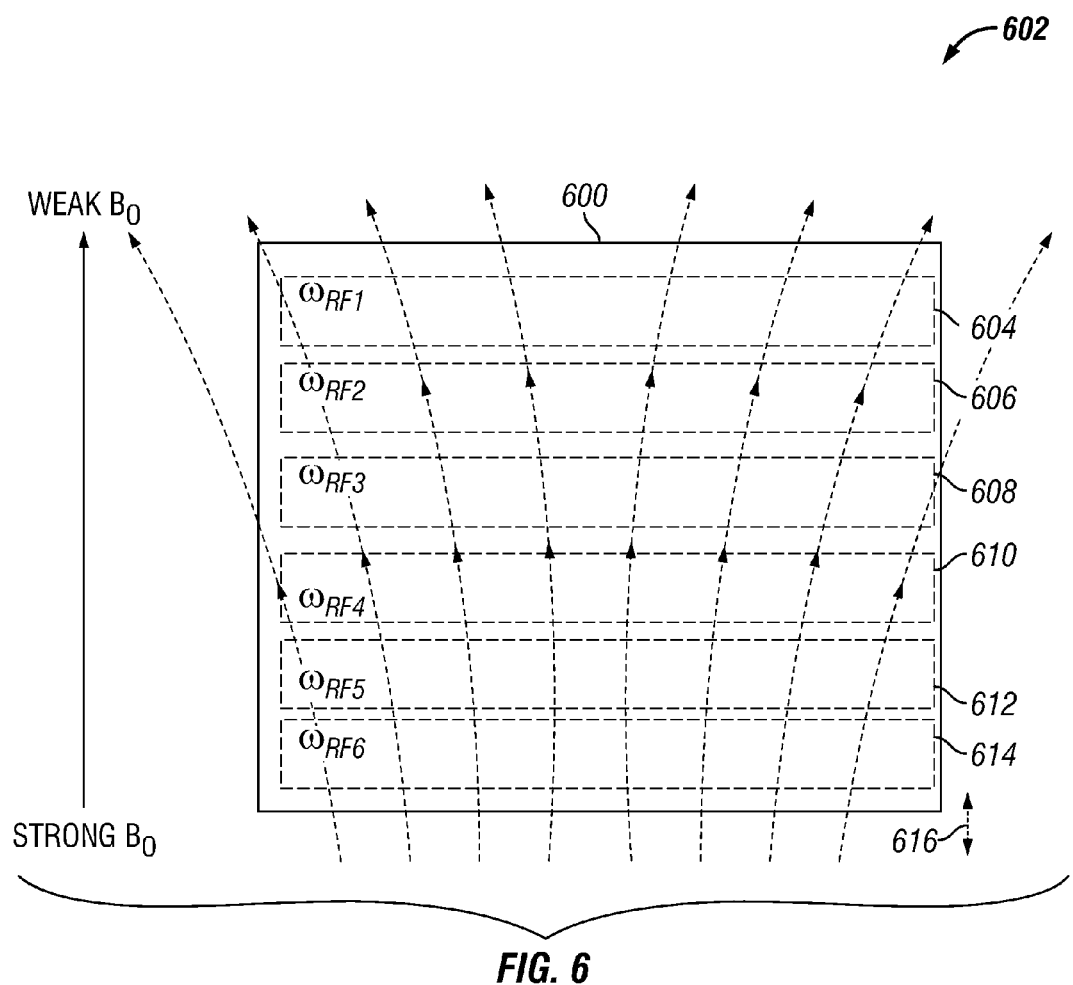
FIG. 6 shows interleaved shells in accordance with one embodiment of the present disclosure.

Illustrative embodiments of the present disclosure are also directed to methods for avoiding interaction between shells because interactions between shells can produce inaccuracies in the measurement. In one such embodiment, NMR pulse sequence segments are interleaved to avoid interaction between shells. An NMR pulse sequence is interleaved when at least some of the shells are temporally skipped to avoid interaction with adjacent shells. FIG. 6 shows interleaved shells in accordance with one embodiment of the present disclosure. In this case, an NMR pulse sequence is applied to an area of interest 600 within a substance 602. The NMR sequence includes six pulse sequence segments applied at six different frequencies ($\omega_{RF1}$, $\omega_{RF2}$, $\omega_{RF3}$, $\omega_{RF4}$, $\omega_{RF5}$ and $\omega_{RF6}$). The six pulse sequence segments generate six shells 604, 606, 608, 610, 612, 614 within the area of interest 600. Instead of applying the pulse sequence segments in order of increasing frequency (e.g., $\omega_{RF1}$, 604→$\omega_{RF2}$, 606→$\omega_{RF3}$, 608→$\omega_{RF4}$, 610→$\omega_{RF5}$, 612→$\omega_{RF6}$, 614) or decreasing frequency (e.g., $\omega_{RF6}$, 614→$\omega_{RF5}$, 612→$\omega_{RF4}$, 610→$\omega_{RF3}$, 608→$\omega_{RF2}$, 606→$\omega_{RF1}$, 604), the shells are temporally skipped to avoid interaction with adjacent shells. The shells that are skipped are then analyzed at a later time. The following is a non-limiting list of interleaved pulse sequence segments:

$\omega_{RF1}$, 604→$\omega_{RF3}$, 608→$\omega_{RF5}$, 612→$\omega_{RF2}$, 606→$\omega_{RF4}$, 610→$\omega_{RF6}$, 614

$\omega_{RF2}$, 606→$\omega_{RF4}$, 610→$\omega_{RF6}$, 614→$\omega_{RF1}$, 604→$\omega_{RF3}$, 608→$\omega_{RF5}$, 612

$\omega_{RF1}$, 604→$\omega_{RF6}$, 614→$\omega_{RF2}$, 606→$\omega_{RF4}$, 610→$\omega_{RF3}$, 608→$\omega_{RF5}$, 612

In this manner, pulse sequence segments can be interleaved to avoid interaction with adjacent shells.

In illustrative embodiments of the present disclosure, NMR pulse sequences are applied to a substance using an NMR system. In some embodiments, the NMR system may include a single coil. Also, the resonant signals generated by the NMR sequences are detected by the coil. In additional or alternative embodiments, the NMR system includes one coil for applying NMR pulse sequences and another coil for detecting resonant signals. In various embodiments, the NMR system includes broadband NMR electronics that are coupled to the coil. The broadband electronics are configured to transmit an NMR pulse sequence to the coil and/or to receive resonant signals that are detected by the coil. Further details of broadband NMR electronics are shown in FIGS. 32A, 32B, 32C, 32D, and 32E.

In various embodiments of the present disclosure, the detected resonant signals that are received by the broadband electronics can be used to determine various properties of the substance, such as an NMR property for the substance. The NMR property can be one or more of $T_1$ relaxation time, $T_2$ relaxation time, diffusion, and/or correlation function of such properties.

In some embodiments, one or more properties can be determined for each of the shells based on the resonant signals originating at the respective shell. In this manner, a depth profile can be determined for the substance. For example, in FIG. 6, the $T_1$ relaxation time for each shell 604, 606, 608, 610, 612, 614 can be determined. Such a profile provides information about how the properties of the substance are changing over the area of interest 600 along a depth dimension 616. In such exemplary embodiments, the multi-segment sequences advantageously speed up measurement of the depth profile by initiating the next pulse sequence before the prior shell reaches thermal equilibrium.

In additional or alternative embodiments, the resonant signals from a plurality of shells ($N_S$) are combined. For example, the amplitudes of each resonant signal can be added together. In some cases, the resonant signals add coherently across the shells, while the noise adds incoherently. The combined signal is used to differentiate the actual resonant signal from noise. In this manner, the combination of signals improves the signal to noise ratio (SNR). According to one exemplary measure, SNR increases by a factor of the square root of the number of pulse sequence segments ($\sqrt{N_S}$). In this manner, illustrative embodiments of the present disclosure improve SNR for NMR measurements.

Figure 7:
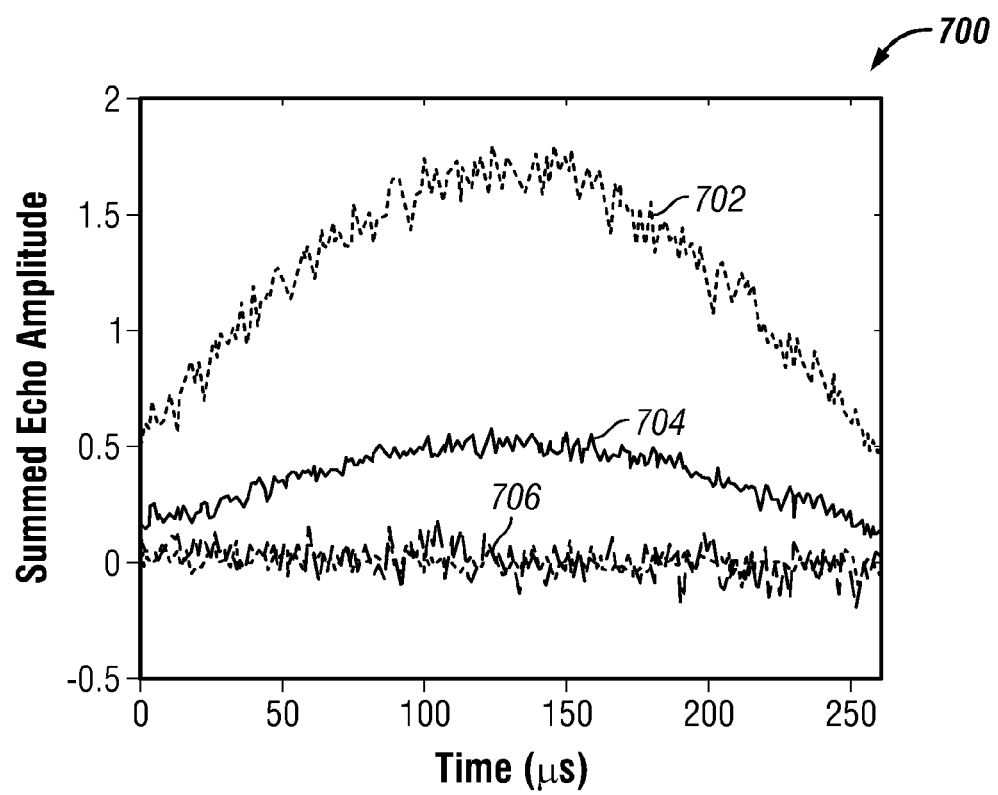
FIG. 7 shows a plot of summed echo amplitude versus time in accordance with one embodiment of the present disclosure.

FIG. 7 shows a plot 700 of summed echo amplitude versus time in accordance with one embodiment of the present disclosure. More specifically, the plot shows a summed amplitude for an NMR pulse sequence with four pulse sequence segments at four different shells (e.g., $N_S$=4) as compared with an NMR pulse sequence at a single shell. The top curve 702 is the sum of the four-shell sequence, the second curve 704 is the single-shell sequence, and the lower curves 706 are noise channels. The SNR for the four-segment sequence 702 was 303, while the SNR for the single-shell sequence 704 was 190. The NMR sequences were applied to a doped-water sample. The doped-water sample had a $T_2$ relaxation time of 120 ms. The NMR pulse sequences were applied to the sample using broadband NMR electronics, as described further below. Within the four-segment sequence, the first segment was applied at 2.0 MHz (e.g., $\omega_{RF}/2\pi$=2.0 MHz) and the frequency difference between the segments was 10 kHz (e.g., $\Delta\omega_{RF}/2\pi$=10 kHz=5.6 $\omega_1$). Also, the excitation pulses for each segment had a duration of 140 μs (e.g., $T_{90}$=140 μs). The echo spacing within each shell was 800 μs (e.g., $T_E$=800 μs) and the four-segment sequence was repeated four times (e.g., N=4). The SNR for the four-segment sequence was greatly improved even though the total time for applying the four-segment sequence was approximately equal to the total time for applying the one-shell sequence. This is so because, in the one-shell sequence, there was an idle time of 500 ms between repetitions of the sequence (e.g., wait time $T_W$=500 ms), whereas, there was no idle time between repetitions of the four-segment sequence (e.g., $T_W$=0 ms).

In yet another embodiment of the present disclosure, multi-segment sequences are applied in 2D NMR measurements. In one exemplary embodiment, each different shell number (e.g., $N_S$) of a multi-segment sequence is used as an indirect dimension (e.g., second dimension). In other words, each shell can be encoded with a different value of an indirect variable, such as a delay between two pulses in the pulse sequence. In this manner, illustrative embodiments of multi-shell sequences speed up 2D NMR measurements (e.g., diffusion and $T_1$ relaxation time) because at least some of the wait times between the sequences can be nullified. The speed up factor can be determined by:

$$S = 1 + \frac{T_W}{N_E T_E} \qquad \text{Eq. 2}$$

Where $T_W$ is the wait time between pulse sequence segments, $N_E$ is the number of refocusing pulses and corresponding echoes within each pulse sequence segment, and $T_E$ is the echo spacing. In some embodiments, $T_W$ is approximately equal to 3 times $T_1$ to allow for longitudinal relaxation of the shell. Also, in some embodiments $N_E T_E$ is approximately equal to 1.26 times $T_2$ to maximize SNR. Given the relationship defined in Equation 2, the speed up factor can be determined by:

$$S \approx 1 + 2.4 \frac{T_1}{T_2} \qquad \text{Eq. 3}$$

Figure 8:
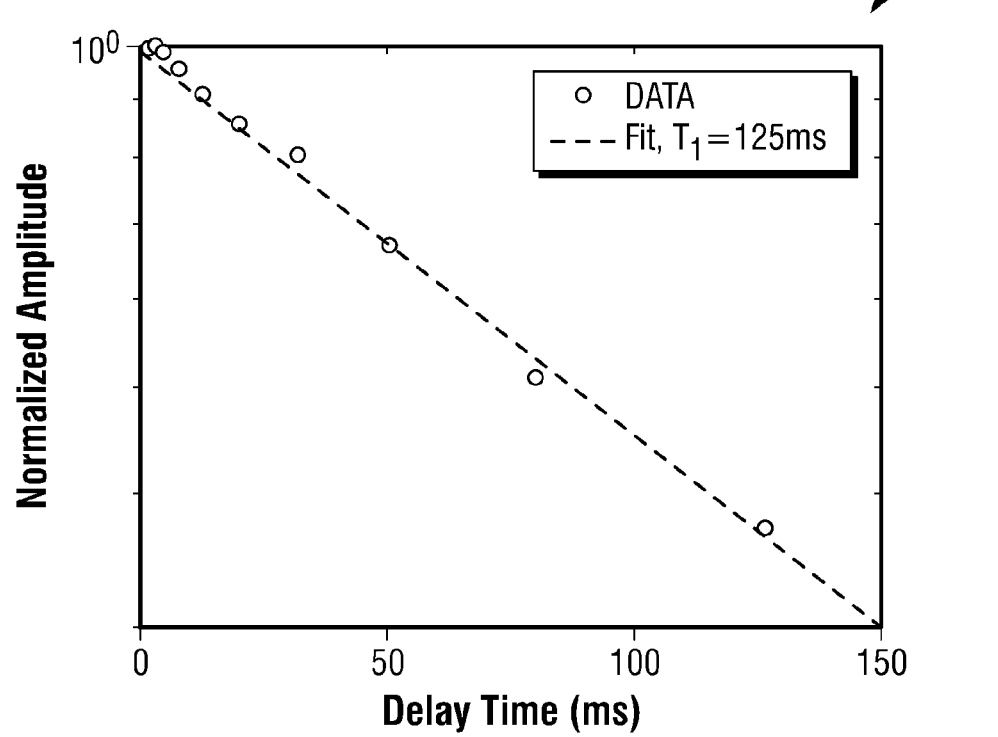
FIG. 8 shows a plot of normalized amplitude versus delay time in accordance with one embodiment of the present disclosure.

FIG. 8 shows a plot 800 of normalized amplitude versus delay time in accordance with one embodiment of the present disclosure. More specifically, the plot shows normalized amplitude for a 2D NMR measurement. The measurement used an inversion recovery sequence for measuring $T_1$ that was accelerated by encoding each shell with a different recovery time. Also, the measurement used a multi-segment sequence with six pulse sequence segments at six different shells (e.g., $N_S$=6). The pulse sequence segments were interleaved to reduce interaction between shells. The pulse sequence segments were interleaved in the following manner: $\omega_{RF1}, \to \omega_{RF3}, \to \omega_{RF5}, \to \omega_{RF2}, \to \omega_{RF4}, \to \omega_{RF6}$. The sequence had no idle time between segments.

The 2D NMR measurement was applied to a doped-water sample. The doped-water sample had a $T_2$ relaxation time of 120 ms. The NMR pulse sequences were applied to the sample using broadband NMR electronics. The first pulse sequence segment was applied at 1.25 MHz (e.g., $\omega_{RF}/2\pi$=1.25 MHz) and the frequency difference between the pulse sequence segments was 13 kHz (e.g., $\Delta\omega_{RF}/2\pi$=13 kHz=4.4 $\omega_1$). Also, the excitation pulses for each segment had a duration of 90 μs (e.g., $T_{90}$=90 μs). The echo spacing within each shell was 1 ms (e.g., $T_E$=1 ms) and the pulse sequence were repeated 128 times (e.g., N=128). The 2D NMR measurement determines the value of $T_1$ from decay data, as shown in for example FIG. 8. In this example, $T_1$ is equal to 125 ms.

Figure 9:
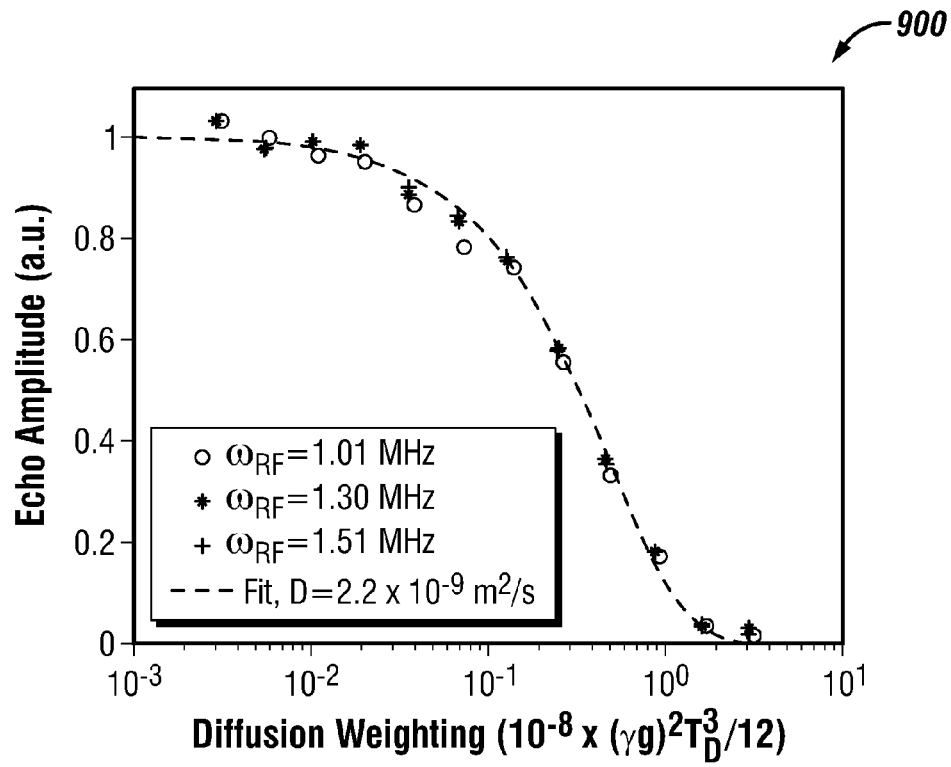
FIG. 9 shows a plot of echo amplitude versus diffusion weighting in accordance with one embodiment of the present disclosure.

FIG. 9 shows a plot 900 of echo amplitude versus diffusion weighting in accordance with one embodiment of the present disclosure. More specifically, the plot shows echo amplitude for another 2D NMR measurement at three different locations within a sample. The measurement used a low-gradient diffusion editing (LG-DE) sequence for measuring a molecular diffusion coefficient. The LG-DE sequence was accelerated by encoding each shell with a different diffusion time. The measurement used a multi-segment sequence with six pulse sequence segments at six different shells (e.g., $N_S$=6). The pulse sequence segments were also interleaved in the following manner: $\omega_{RF1}, \to \omega_{RF3}, \to \omega_{RF5}, \to \omega_{RF2}, \to \omega_{RF4}, \to \omega_{RF6}$. In this case, the sequence had an idle time of 5 ms between segments. Such a small delay can reduce artifacts in the decay curve by ensuring that diffusion nullifies at least a portion of the transverse magnetization before the next shell is excited. During the measurement, a dummy shell (e.g., separated from the first shell by the normal shell separation) was excited before the first shell was excited. A dummy shell further reduces artifacts in the decay curve by ensuring that all shells are equally spoiled by preceding excitations.

The 2D NMR measurement was applied to a doped-water sample at three different sample locations. The doped-water sample had a $T_2$ relaxation time of 120 ms. The NMR pulse sequences were applied to the sample using broadband NMR electronics. The first pulse sequence segments were applied at the following frequencies: 1.51 MHz; 1.30 MHz; 1.01 MHz (e.g., $\omega_{RF}/2\pi$=1.51 MHz; $\omega_{RF}/2\pi$=1.30 MHz; $\omega_{RF}/2\pi$=1.01 MHz). The frequency difference between the pulse sequence segments was 10 kHz (e.g., $\Delta\omega_{RF}/2\pi=10$ kHz). Also, the excitation pulses for each segment at the three different locations had a duration of 105 µs, 87.5 µs, and 70 µs (e.g., $T_{90}=105$ µs; $T_{90}=87.5$ µs; $T_{90}=70$ µs). The echo spacing within each shell was 1 ms (e.g., $T_E=1$ ms) and the pulse sequence was repeated 128 times (e.g., N=128). As shown in FIG. 9, the 2D NMR measurement determines a correct value for a diffusion coefficient (D). The figure also shows that the measurements are independent of the nominal Larmor frequency of the sample (e.g., the location of the measurement within the sample). Further measurements demonstrated similar favorable results for more widely-separated locations within the sample.

Figure 10:
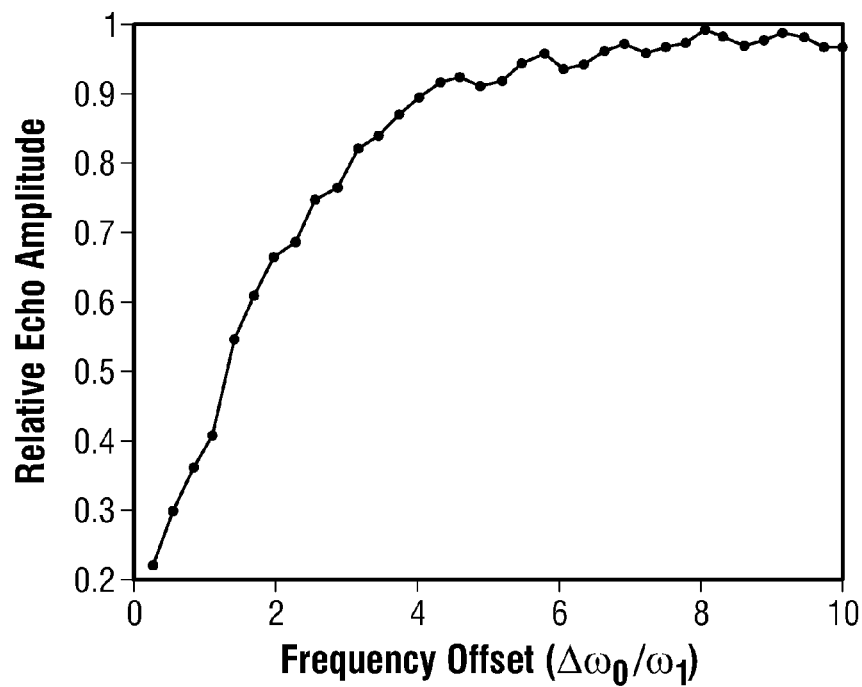
FIG. 10 shows a plot of relative echo amplitude versus frequency offset in accordance with one embodiment of the present disclosure.

FIG. 10 shows a plot 1000 of relative echo amplitude versus frequency offset in accordance with one embodiment of the present disclosure. More specifically, the plot shows measured "spoiling" between nearby shells for rectangular pulses as a function of the frequency offset. The thickness of a shell is defined at least in part by the longitudinal magnetization of the nuclei within the shell. When applying NMR sequences, in many cases, it is much easier to nullify longitudinal magnetization than to generate the required transverse magnetization. For this reason, common pulse sequences, such as CPMG sequences, create "holes" in longitudinal magnetization that are much wider than the shells from which they produce detectable resonant signals. Such "hole burning" or "spoiling" limits the minimum spacing between adjacent shells. The plot in FIG. 10 shows measured "spoiling" between nearby shells for rectangular pulses as a function of the frequency offset. The measurement was performed using a series of CPMG sequences applied at different offset frequency values (e.g., $\Delta\omega_{RF}$). The measurement was applied to a doped-water sample having a $T_2$ relaxation time of 120 ms. Furthermore, the pulse sequences were applied to the sample using broadband NMR electronics. FIG. 10 shows that a frequency offset $\Delta\omega_0$ between shells of greater than four times $\omega_1$ provides for less than 10% spoiling, where $\omega_1=\gamma B_1$. Also, there is very little spoiling for frequency offset values $\Delta\omega_0$ that are greater than 8 times $\omega_1$. For 90 degree rectangular pulses and 180 degree rectangular pulses zero spoiling occurs when the resonant offset frequency has the values determined by Equation 4 and Equation 5, respectively:

$$\Delta\omega_0 = \pm(\sqrt{16n^2-1})\omega_1 \quad \text{Eq. 4}$$

$$\Delta\omega_0 = \pm(\sqrt{4n^2-1})\omega_1 \quad \text{Eq. 5}$$

where n is an integer (e.g., 1, 2, . . . ).

Figure 11:
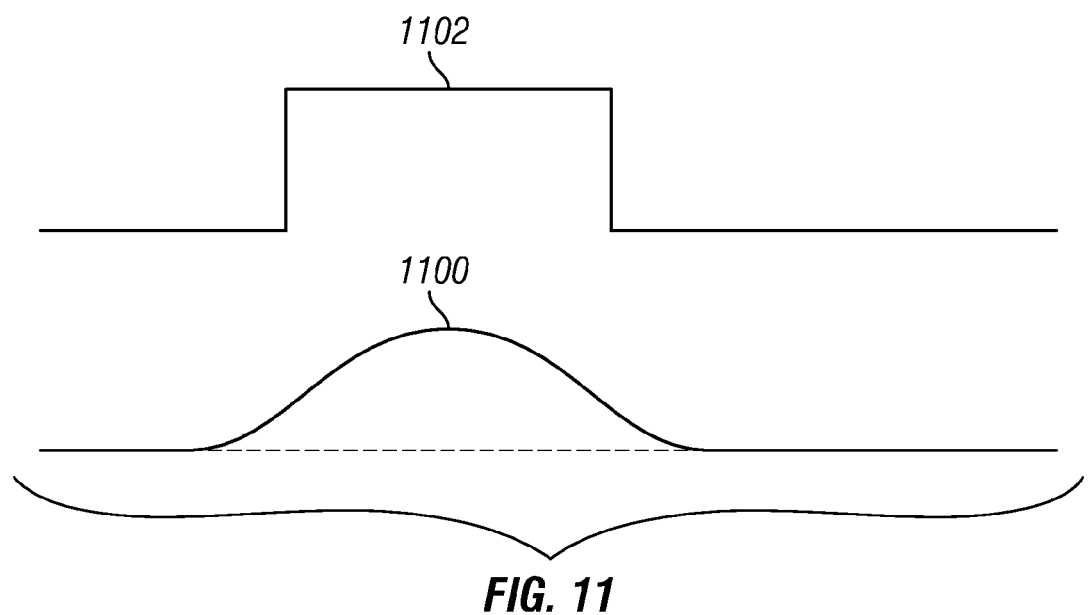
FIG. 11 shows a pulse with a Gaussian envelope as compared with a rectangular pulse in accordance with one embodiment of the present disclosure.

In illustrative embodiments of the present disclosure, such interactions between shells can be reduced by using shaped pulses that gradually turn on and off. In one such example, pulses with Gaussian envelopes reduce the amount of spoiling and hole burning between shells. FIG. 11 shows a pulse with a Gaussian envelope 1100 as compared with a rectangular pulse 1102 in accordance with one embodiment of the present disclosure. In this manner, illustrative embodiments reduce interactions between shells.

Illustrative embodiments of the present disclosure are directed to multi-segment sequences that further improve the efficiency of NMR measurements (e.g., interposed sequences). To this end, various embodiments apply at least two pulse sequence segments to a substance. The NMR pulse sequence segments are applied at two different frequencies and are interposed within each other. In this manner, such various interposed sequences perform measurements in parallel, whereas in many conventional systems, the measurements are performed in series.

Figure 12:
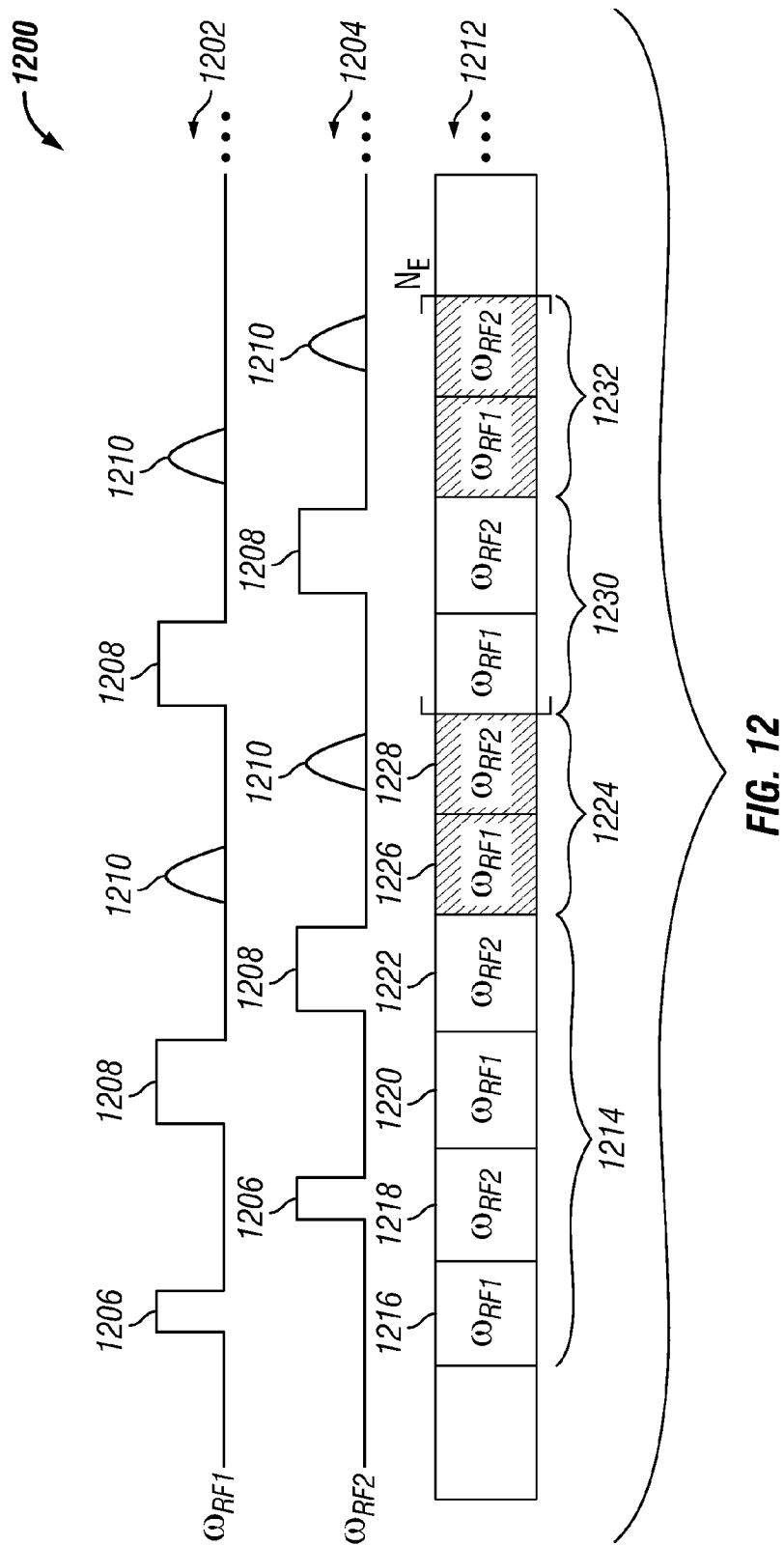
FIG. 12 shows an NMR pulse sequence with interposed pulse sequence segments in accordance with one embodiment of the present disclosure.

FIG. 12 shows an NMR pulse sequence 1200 with interposed pulse sequence segments in accordance with one embodiment of the present disclosure. The NMR pulse sequence 1200 includes at least a first pulse sequence segment 1202 and a second pulse sequence segment 1204. Each segment includes an excitation pulse 1206, a series of refocusing pulses 1208, and a series of echoes 1210. In various embodiments, the excitation pulses have a length of $T_{90}$ and the refocusing pulses have a length of $T_{180}$. The pulses also have amplitudes that typically range between 1 G and 10 G. In one specific example, the sequence segments 1202, 1204 are CPMG sequences. In various other embodiments, the sequence segments 202, 204 can be spin echo, inversion recovery, saturation recovery, and/or stimulated echo sequences. Illustrative embodiments of the present disclosure, however, are not limited to such specific sequences, pulse lengths and amplitudes.

As shown in FIG. 12, the second segment 1204 is interposed within the first segment 1202. In other words, at least one pulse or detected echo of the second sequence segment 1204 occurs before the first pulse sequence segment 1202 is completed. The first segment 1202 is applied to the substance with a first set of frequencies ($\omega_{RF1}$) and the second segment 1204 is applied to the substance with a second set of frequencies ($\omega_{RF2}$). An average of the first set of frequencies and an average a second set of frequencies are different by a difference of $\Delta\omega_{RF}$. In some embodiments, the frequency difference of $\Delta\omega_{RF}$ is as great as 10% of the first frequency. In various other embodiments, the frequency can be even greater (e.g., 20% 30% or 50%).

The NMR pulse sequence 1200 applied to the substance generates resonant signals within the substance. The resonant signals are composed of a series of echoes. The first pulse sequence segment 1202 will generate a first resonant signal in a first shell, while the second pulse sequence segment 1204 will create a second resonant signal within a second shell.

Figure 13:
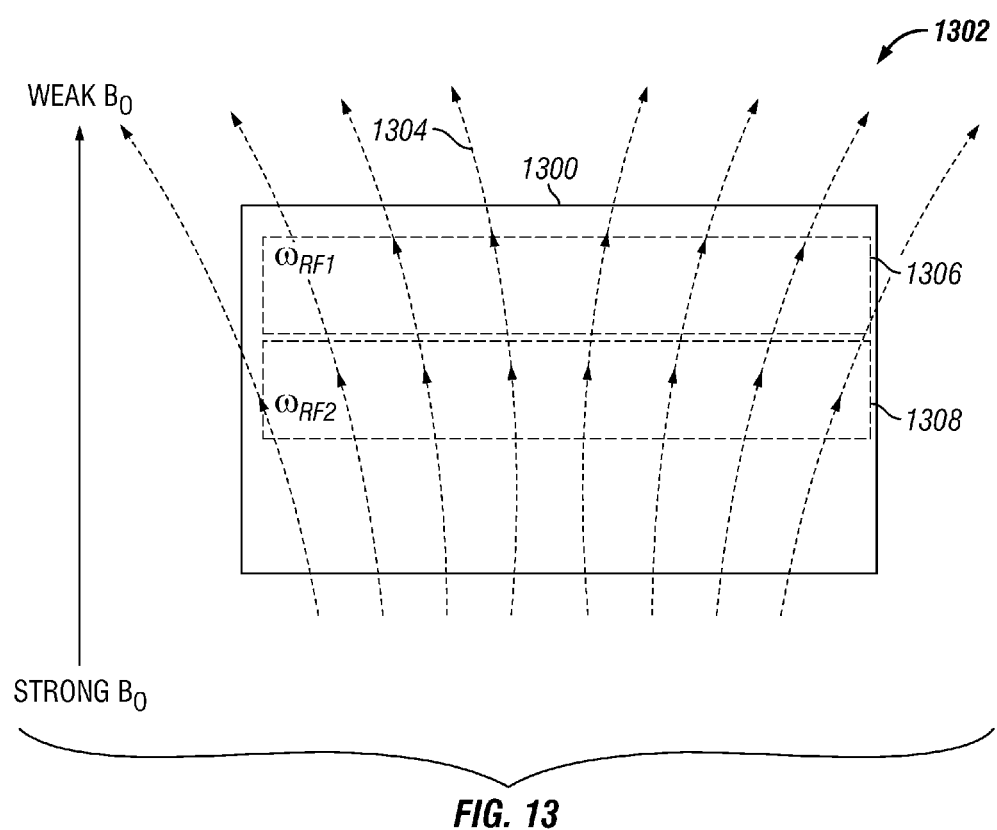
FIG. 13 shows an area of interest within a substance in accordance with one embodiment of the present disclosure.

FIG. 13 shows an area of interest 1300 within a substance 1302 in accordance with one embodiment of the present disclosure. In FIG. 13, an inhomogeneous magnetic field 1304 is applied to the area of interest 1300 within the substance 1302. When the first pulse sequence segment 1202 and the second pulse sequence segment 1204 are applied to the area of interest 1300 within the substance 1302, the substance generates two resonant signals with two different frequencies (e.g., sets of frequencies). The first resonant signal originates at a first shell 1306 and a second resonant signal originates at a second shell 1308 within the area of interest 1300. The two resonant signals have different frequencies because the static magnetic field 1304 is different at each location within the area of interest 1300 of the substance 1302. The frequency of each signal can be determined using, for example, Equation 1, where $B_0$ is the strength of the static magnetic field 1304, $\gamma$ is the gyromagnetic ratio of the atomic nuclei of interest and $\omega_0$ is the frequency of the resonant signal that is produced by the atomic nuclei.

The first resonant signal and the second resonant signal are detected. These detected signals can be used to determine NMR properties for the substance 1302 (e.g., $T_1$ relaxation time, $T_2$ relaxation time and/or diffusion). In turn, the NMR properties can be used to determine physical properties of the substance, such as the chemical composition of the substance and/or the presence of solid phase and/or liquid phase within the substance.

Figure 14:
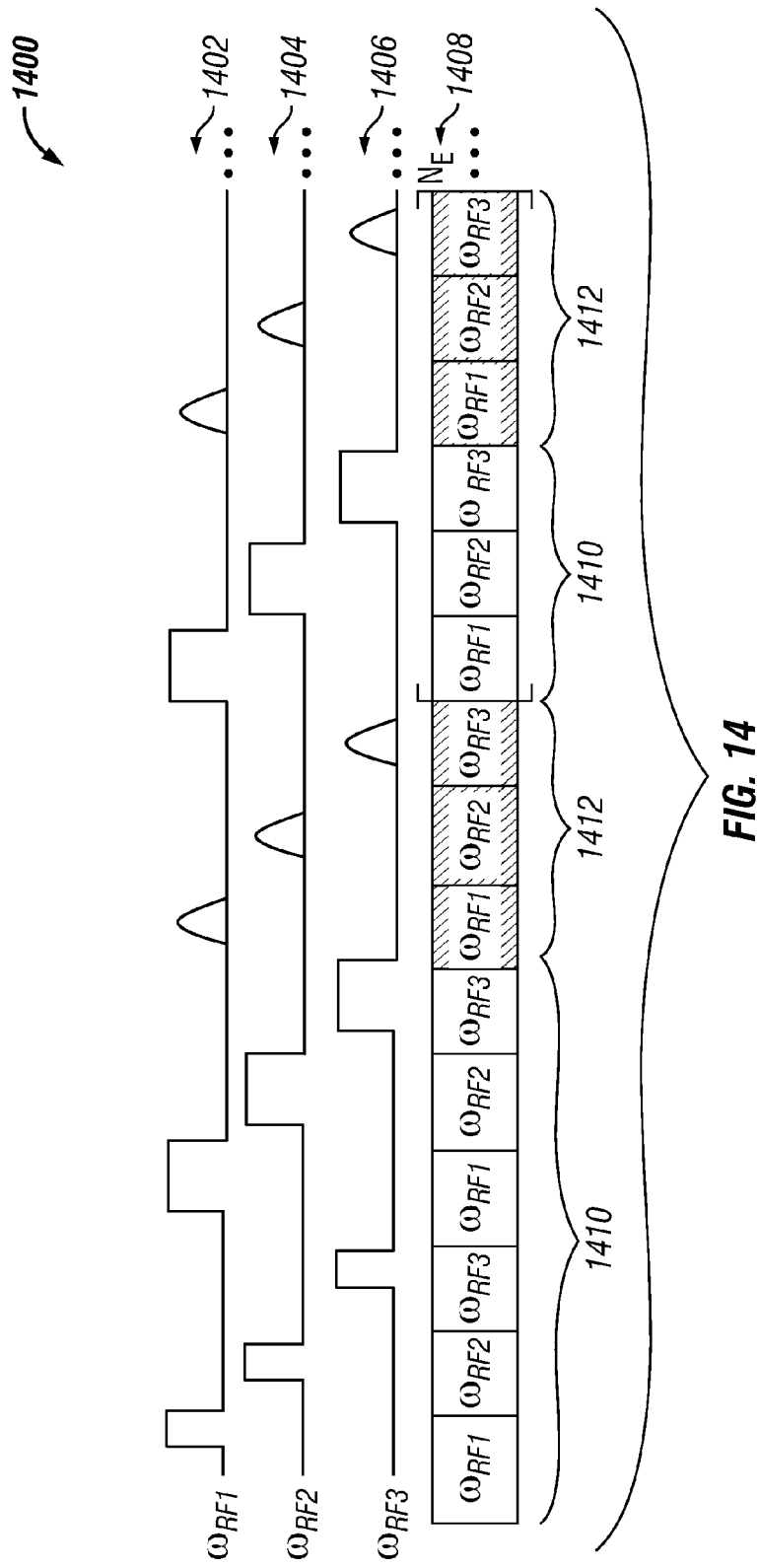
FIG. 14 shows an NMR pulse sequence with interposed pulse sequence segments in accordance with another embodiment of the present disclosure.
Figure 15:
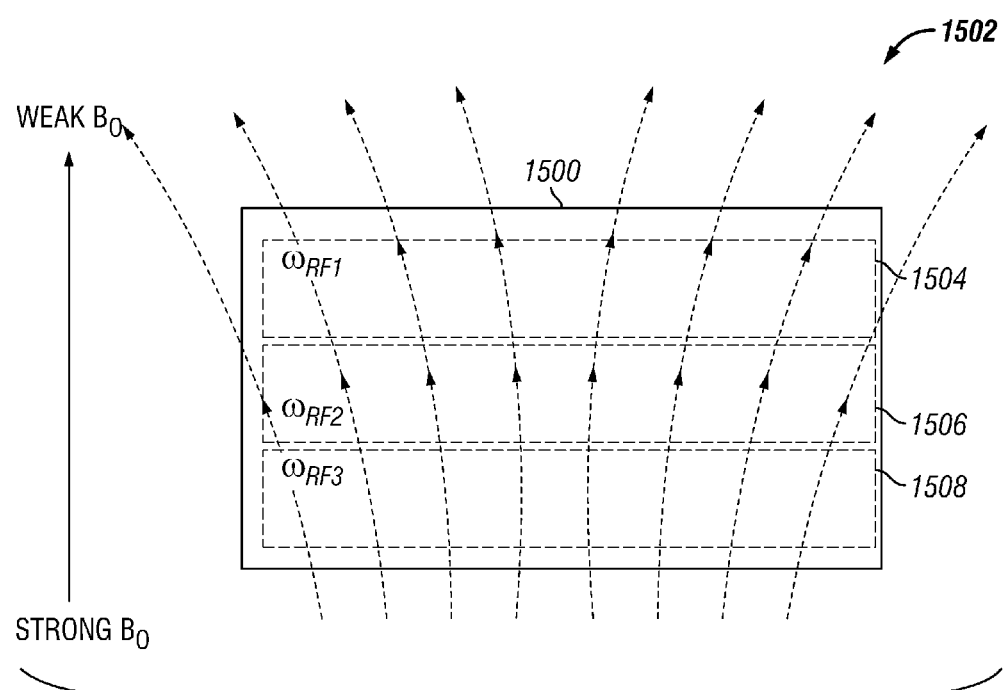
FIG. 15 shows three shells generated by a three-segment NMR pulse sequence within an area of interest of a substance in accordance with one embodiment of the present disclosure.

FIG. 14 shows an NMR pulse sequence 1400 with interposed pulse sequence segments in accordance with another embodiment of the present disclosure. In FIG. 14, the NMR pulse sequence 1400 includes three pulse sequence segments. A first segment 1402 is applied to the substance with a first set of frequencies ($\omega_{RF1}$), a second segment 1404 is applied to the substance with a second set of frequencies ($\omega_{RF2}$), and a third segment 1406 is applied to the substance with a third set of frequencies ($\omega_{RF3}$). Each of the second segment 1404 and the third segment 1406 are interposed within the first segment 1402. Such an NMR pulse sequence 1400 generates resonant signals within three shells. FIG. 15 shows three shells 1504, 1506, 1508 generated by the three-segment NMR pulse sequence 1400 within an area of interest 1500 of the substance 1502. Illustrative embodiments of the present disclosure are not limited to two or three interposed pulse sequence segments. Exemplary embodiments may include 4, 5, 9 or more interposed pulse sequence segments.

Figure 16:
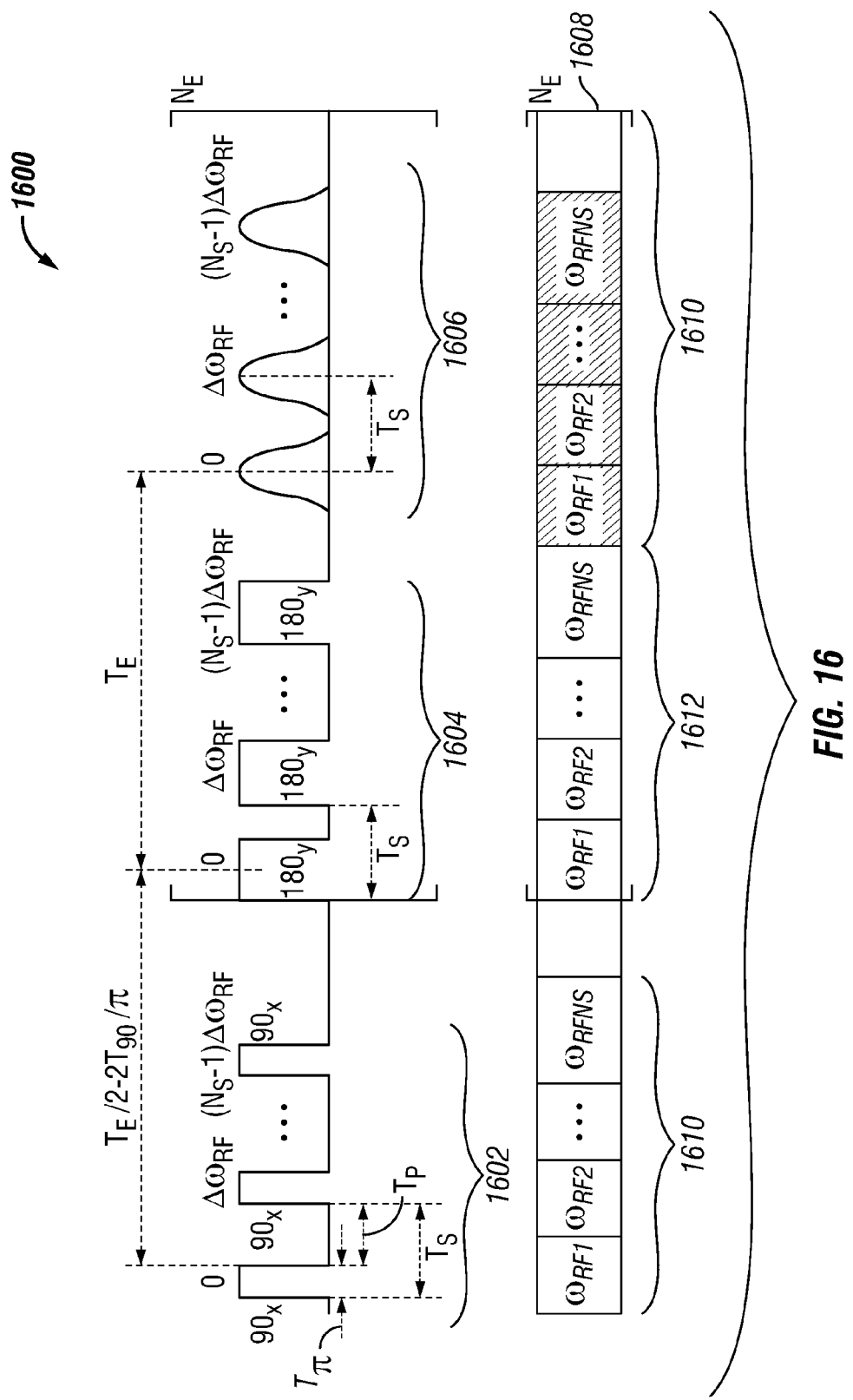
FIG. 16 shows an NMR pulse sequence with greater than two interposed pulse sequence segments in accordance with one embodiment of the present disclosure.

FIG. 16 shows an NMR pulse sequence 1600 with greater than two interposed pulse sequence segments in accordance with one embodiment of the present disclosure. The NMR pulse sequence 1600 includes a number of pulse sequence segments ($N_S$). Each segment includes an excitation pulse 1602, a series of refocusing pulses 1604, and a series of echoes 1606. The sequence segments are applied to the substance with different frequencies. In the specific example shown in FIG. 16, the frequency of the n-th segment is given by $\omega_{RF}+(n-1)\Delta\omega_{RF}$, where $\Delta\omega_{RF}$ is the separation between adjacent shells and $1 \leq n \leq N_S$. In various other embodiments, the separation between shells is not constant and varies.

Also, in one specific embodiment, the refocusing pulse lengths and delays between refocusing pulses can be set to integer multiples of $1/(\Delta\omega_{RF})$ to maintain phase coherence within each shell. In additional or alternative embodiments, phase coherence can be maintained by explicitly tracking the phase of each shell in a rotating frame and appropriately modulating the phase of the refocusing pulses.

As shown in FIG. 16, echoes from each shell form sequentially in time (e.g., separated by $T_S$, where $T_S$ is the length of each refocusing interval and excitation interval). Given this phenomenon, the echoes can be distinguished from each other based upon their placement in time. In additional or alternative embodiments, the echoes can be distinguished from each other based upon their frequency content.

Illustrative embodiments of the present disclosure are also directed to compensating for the Bloch-Siegert (B-S) phase shift. The inventors herein have discovered that interposed pulse sequence segments with different frequencies can be adversely affected by the B-S phase shift. In particular, the B-S phase shift can cause rapid signal decay when applying an NMR pulse sequence with interposed pulse sequence segments. To prevent this rapid signal decay, the B-S phase shift can be corrected by phase shifting excitation pulses for the second and successive pulse sequence segment (e.g., $N_S>1$). In other words, each excitation pulse applied subsequent to the first excitation pulse is applied with a shifted phase. In an additional or alternative embodiment, the time interval between each excitation pulse is varied to account for the B-S shift within a single shell. Details of these corrections are provided below.

In various embodiments, the timing of a pulse sequence segment is adjusted such that the phase acquired between the excitation pulse and the first refocusing pulse is about half the phase acquired in each refocusing cycle. In some embodiments, this phase is proportional to the Larmor frequency and can be determined by:

$$\varphi_L = \gamma \omega_{RF} T_E \qquad \text{Eq. 6}$$

where $\gamma$ is the gyromagnetic ratio of a nucleus of interest, $\omega_{RF}$ is the frequency of the pulse sequence segment, and $T_E$ is the echo spacing. When multiple pulse sequence segments are run simultaneously on different shells, various embodiments of the present disclosure compensate for interactions between the shells that result from the B-S shift. In one example, a first pulse sequence segment with a first frequency $\omega_{RF1}$ is applied to the substance and a second pulse sequence segment with a second frequency $\omega_{RF2}$ is applied to the substance. An offset $\Delta\omega_{RF}$ between the first frequency and the second frequency induces an extra phase shift on the transverse magnetization. This so-called "Bloch-Siegert" shift is designated herein as $\varphi_{BS}$. In cases where $\Delta\omega_{RF}$ is much larger (e.g., larger than $2\omega_1$) than the frequency $\omega_1$, the phase shift for on-resonance magnetization can be determined by:

$$\varphi_{BS} = \left(\frac{\theta}{2}\right)\frac{\omega_1}{\Delta\omega_{RF}}. \qquad \text{Eq. 7}$$

where $\theta$ is the nominal tipping angle of the pulse. The nominal tipping angle can be determined by:

$$\theta = \gamma 2\pi t_p \qquad \text{Eq. 8}$$

where $t_p$ is the duration of the pulse and $\gamma$ is the gyromagnetic ratio of the nucleus of interest.

Figure 19:
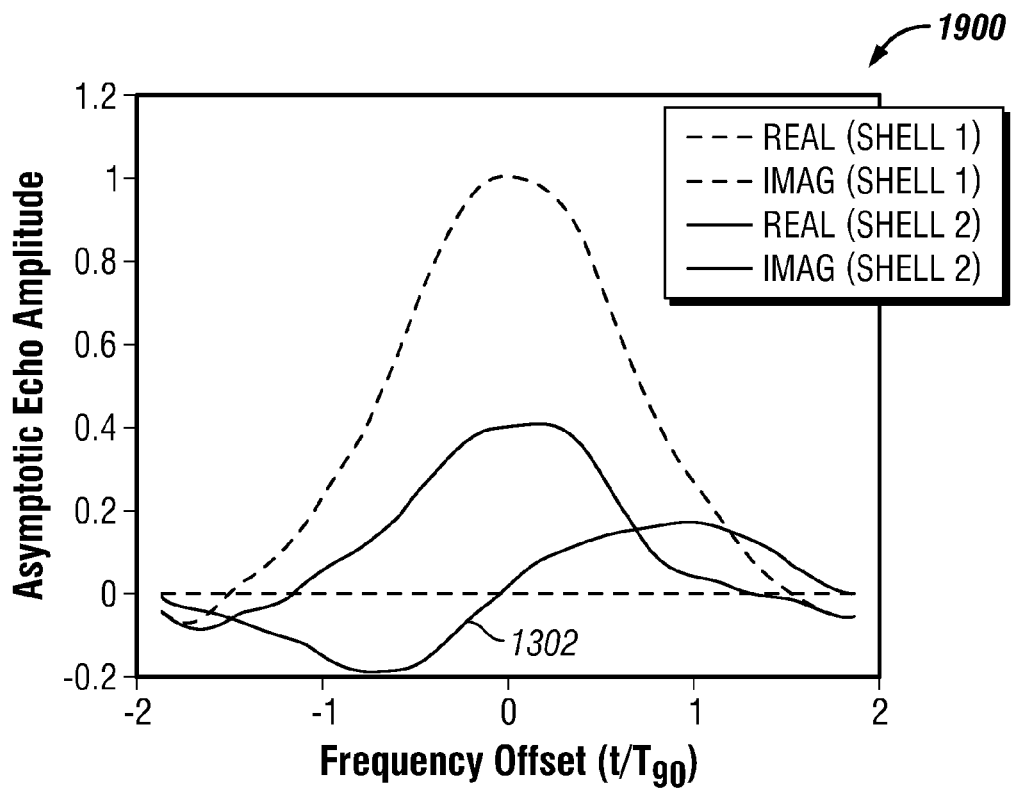
FIG. 19 shows a simulated plot of asymptotic echo amplitude versus echo acquisition time in accordance with one embodiment of the present disclosure.

The NMR pulse sequence shown in FIG. 19 includes a plurality of interposed pulse sequence segments ($N_S$). Various embodiments of the present disclosure compensate for the B-S phase shift by modulating the phase and/or timing of excitation pulses within the plurality of interposed pulse sequence segments. The phase shift for a spin in a shell consists of the standard Larmor phase shift between two refocusing pulses. This phase shift can be determined by adding the result of Equation 6 to the phase shifts induced by the pulse sequence segments (e.g., $N_S-1$) applied to previous shells. For the pulse sequence segment applied to the first shell, the phase shift between the excitation pulse and the first refocusing pulse remains half the total phase shift because the B-S phase shift is proportional to pulse duration. In one example, the B-S phase shift is proportional to the pulse duration when the refocusing pulses are twice as long and have the same amplitude as the excitation pulse (e.g., the excitation pules is 90 degrees and the excitation pulses are 180 degrees).

For a second pulse sequence segment applied to a second shell, this proportionally is not fulfilled. During the time interval between when the excitation pulse of the second pulse sequence segment and the first refocusing pulse of the second pulse sequence segment are applied, a refocusing pulse is applied to the first shell as part of the first pulse sequence segment. This refocusing pulse adversely affects the second pulse sequence segment. If the refocusing pulse is a 180 degree pulse, then the associated B-S phase shift is twice as long, as compared with the 90 degree excitation pulse. The total phase shift caused by first pulse sequence segment and the first shell can be determined by:

$$\Delta\varphi_{BS,2} = -\left(\frac{\pi}{4}\right)\frac{\omega_1}{\Delta\omega_{RF}} \qquad \text{Eq. 9}$$

The first pulse sequence segment and second pulse sequence segment also produce phase shifts that affect any potential third pulse sequence segment. Furthermore, each subsequent pulse sequence segment is affected by phase shifts produced by segments applied before the subsequent segment. These phase shifts can be compensated by determining and summing the phase shift contribution of each previous pulse sequence segment. Equation 10 below can be used to determine the total phase shift for a plurality of previous pulse sequence segments:

$$\Delta\varphi_{BS,k} = -\frac{\pi}{4}\frac{\omega_1}{\Delta\omega_{RF}}\left(1 + \frac{1}{2} + \frac{1}{3} + \dots \frac{1}{k-1}\right) \quad \text{Eq. 10}$$

The integer k is the pulse sequence segment of interest and (k−1) is the number of pulse sequence segments that contribute to the total phase shift. Using Equation 10, the B-S phase shift can be corrected by replacing the standard excitation pulse (e.g., $90_x$) within the k-th pulse sequence segment with an excitation pulse that has a modulated phase. In a particular embodiment, the phase of the excitation pulse is modulated by the total phase shift produced by the previous pulse sequence segments. In other words, the phase of the excitation pulse within the k-th pulse sequence segment is equal to the phase of the excitation pulse in the first segment minus the result of Equation 10 (e.g., 90−$\Delta\varphi_{BS,k}$).

Illustrative embodiments of the present disclosure are also directed to correcting for the B-S phase shift when the phase shift is not constant within a single shell. Equation 9 shows that the B-S phase shift can vary within a shell because the offset frequency ($\Delta\omega_{RF}$) varies linearly across the shell. This phenomenon can be addressed by shifting the position of the excitation pulse for the k-th pulse sequence segment by:

$$\delta\tau_k = \frac{t_\pi}{2}\left(1 + \frac{1}{2^2} + \frac{1}{3^2} + \dots \frac{1}{(k-1)^2}\right). \quad \text{Eq. 11}$$

In Equation 11, $t_x$ is the length of the excitation pulse within the first pulse sequence segment. In this manner, the B-S phase shift can be corrected by replacing a standard time interval ($T_p$) between the excitation pulses within the first and second segments with a time interval ($T_p$) that is varied. In a particular embodiment, the initial time interval ($T_p$) is modulated by the result of Equation 11 (e.g., $\delta_{Tk}$). In other words, the time interval between the excitation pulse in the k-th pulse sequence segment and the excitation pulse of the next pulse sequence segment is equal to the initial time interval ($T_p$) plus the result of Equation 11 (e.g., $\delta_{Tk}$). In this manner, various embodiments of the present disclosure account for the B-S phase shift within interposed pulse sequence segments.

In various embodiments, the multi-segment sequences described herein are applied at a plurality of different frequencies. In some embodiments, the segments within each sequence are interposed. To apply the sequences and detect resonant signals, various embodiments of the present disclosure are directed to NMR electronics that are configured to switch between a transmitting mode and a receiving mode. Within a transmitting mode, the electronics are further configured to switch between various frequencies so that the coil can apply pulse sequence segments at different frequencies. Within a receiving mode, the electronics are configured to switch between various frequencies so that the coil and electronics can detect resonant signals at different frequencies. In various embodiments, the switching of frequencies is performed according to a particular schedule.

FIG. 14 shows a switching schedule 1412 for the NMR pulse sequence 1400 in accordance with one embodiment of the present disclosure. In the specific example, the switching schedule 1412 begins with a first set of time intervals 1414. During the first set of time intervals 1414, the broadband NMR electronics are set to a transmitting mode. The first set of time intervals includes four time intervals 1416, 1418, 1420, 1422. During the first time interval 1416, the electronics are set to a first frequency ($\omega_{RF1}$) so that the coil can apply the first excitation pulse 1406 of the first pulse sequence segment 1402. During the second time interval 1418, the electronics are set to a second frequency ($\omega_{RF2}$) so that the coil can apply the first excitation pulse 1406 of a second pulse sequence segment 1404. During the third time interval 1418, the electronics are set to the first frequency ($\omega_{RF1}$) so that the coil can apply the first refocusing pulse 1408 of the first pulse sequence segment 1402. During the fourth time interval 1422, the electronics are set to the second frequency ($\omega_{RF2}$) so that the coil can apply the first refocusing pulse 1408 of the second pulse sequence segment 1404. As explained above, the frequency (e.g., $\omega_{RF1}$) within a pulse segment or a single pulse may not be a single frequency. The frequency within a pulse sequence segment or a single pulse can vary over a set of frequencies (e.g., over a range of frequencies).

Following the first set of time intervals 1414, a second set of time intervals 1424 begins. During the second set of time intervals 1424, the broadband NMR electronics switch to a receiving mode of operation. The second set 1424 includes two time intervals 1426, 1428. The first time interval 1426 is dedicated to detecting a resonant signal at the first frequency ($\omega_{RF1}$) generated by the first pulse sequence segment 1402 (e.g., within the first shell). In the embodiment shown in FIG. 14, a single echo 1410 is detected at the first frequency. The second time interval 1428 is dedicated to detecting a resonant signal at the second frequency ($\omega_{RF2}$) generated by the second pulse sequence segment 1404 (e.g., within the second shell). Again, a single echo 1410 is detected at the second frequency.

Next, a third set of time intervals 1430 follows. During the third set of time intervals 1430, the broadband NMR electronics are switched back to a transmitting mode of operation. During this set of time intervals 1430, one more refocusing pulse 1408 is applied at each of the two different frequencies (e.g., $\omega_{RF1}$ and $\omega_{RF2}$). Then, a fourth set of time intervals 1432 follows. During the fourth set of time intervals 1432, the broadband NMR electronics are switched to a receiving mode of operation. During the fourth set of time intervals 1432, resonant signals (e.g., echoes) 1410 are detected at each of the two different frequencies (e.g., $\omega_{RF1}$ and $\omega_{RF2}$). The third and fourth sets of time intervals 1430, 1432 can be repeated a plurality of times (e.g., $N_E$=10, $N_E$=100, and $N_E$=1000) until the NMR pulse sequence comes to an end. In some embodiments, the time intervals have equal lengths across the switching schedule. In other embodiments, the time intervals have varying lengths. In various embodiments, the time intervals are at least as long as the excitation pulse and/or refocusing pulse that they are dedicated to applying. Also, the time intervals are at least as long as the echoes that they are dedicated to detecting. In further embodiments, the length of the time intervals is no greater than 1 ms. In yet further embodiments, the length of the time intervals is no greater than 100 μs.

FIGS. 14 and 16 show two switching schedules 1408, 1608 for NMR pulse sequences, 1400, 1600 in accordance with embodiments of the present disclosure. In FIG. 14, the switching schedule 1408 also modulates between a transmitting mode 1410 and a receiving mode 1412. In this case, within each mode, the broadband NMR electronics are switched between three different frequencies (e.g., $\omega_{RF1}$, $\omega_{RF2}$ and $\omega_{RF3}$). Similarly, in FIG. 16, the switching schedule 1608 also modulates between a transmitting mode 1610 and a receiving mode 1612 and within each mode, the broadband NMR electronics are switched between $N_S$ number of different frequencies (e.g., $\omega_{RF1}$, $\omega_{RF2}$, $\omega_{RF3}$, ... $\omega_{RFNs}$). In this manner, various embodiments of the present disclosure apply pulse sequence segments at various different frequencies and detect resonant signals from a plurality of different shells within the substance.

Figure 17:
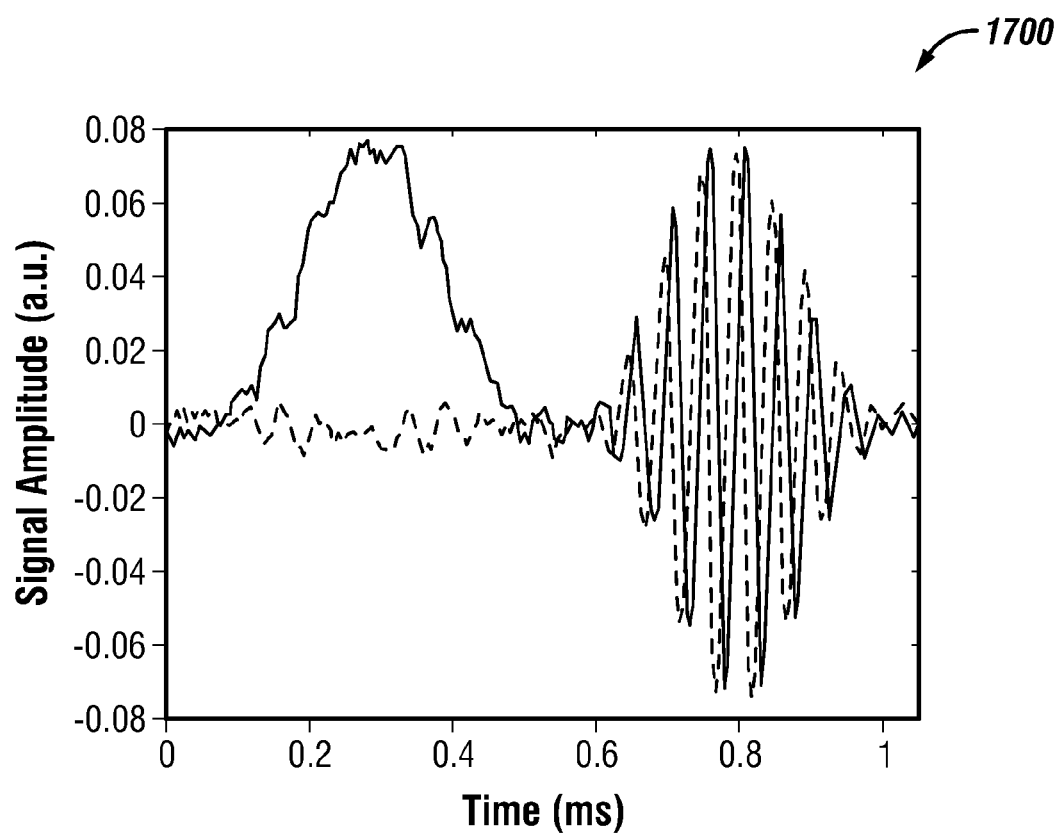
FIG. 17 shows a plot of signal amplitude versus time in accordance with one embodiment of the present disclosure.

FIG. 17 shows a plot 1700 of measured signal amplitude versus time in accordance with one embodiment of the present disclosure. More specifically, FIG. 17 shows asymptotic echoes that were detected for an NMR sequence with two interposed pulse sequence segments (e.g., $N_S$=2). The segments generated resonant signals within two shells of a doped-water sample. The doped-water sample had a $T_2$ relaxation time of 120 ms. The two interposed pulse sequence segments were applied to the sample using broadband NMR electronics. The first pulse sequence segment was applied at 2.0 MHz (e.g., $\omega_{RF}/2\pi$=2.0 MHz) and the frequency difference between the first pulse sequence segment and the second pulse sequence segment was 20 kHz (e.g., $\Delta\omega_{RF}/2\pi$=20 kHz=11.8 $\omega_1$). Also, the excitation pulses for each segment had a duration of 140 μs (e.g., $T_{90}$=140 μs). The echoes between each shell were separated by 500 μs (e.g., $T_S$=500 μs) and the sequence was repeated 128 times (e.g., N=128). The receiver frequency was kept constant at the center frequency of the first pulse sequence segment (e.g., $\omega_{RF}/2\pi$=2.0 MHz) so the first echo sequence was demodulated to zero frequency (e.g., baseband). The second echo sequence was demodulated to an offset frequency of 20 kHz (e.g., $\Delta\omega_{RF}/2\pi$=20 kHz). The echoes from each resonant signal were distinguished by the placement in time (e.g., $T_S$=500 μs). In various other embodiments, the echoes can also be distinguished by their frequency content.

Illustrative embodiments of the present disclosure are also directed to multi-segment sequences that are applied to generate interactions between shells and these interactions between shells are used to determine an NMR property. Such multi-segment sequences influence magnetization in one shell of a substance by manipulating spins in other shells of the substance. In one embodiment, such a method includes applying an NMR pulse sequence to the substance. The NMR pulse sequence includes at least a first pulse sequence segment at a first set of frequencies and a second pulse sequence segment at a second set of frequencies. The second pulse sequence segment generates a resonant signal within a shell of the substance and the first pulse sequence segment generates a characteristic within the resonant signal through interaction with another shell. The resonant signal is detected and an NMR property is determined based upon the characteristic within the detected resonant signal.

In various embodiments, the characteristic may be an imaginary component within the detected resonant signal that is introduced by the first pulse sequence segment. For example, the first pulse sequence segment may introduce an asymmetry in longitudinal magnetization within the shell. In another example, the characteristic may be a phase shift within the detected resonant signal.

In some embodiments, the NMR property that is determined is an NMR property of the substance, such as a long spin-lattice $T_1$ relaxation time of the substance. In another example, the NMR property is a property of the NMR measurement itself. In one specific example, the property of the NMR measurement is the magnitude of the applied oscillating field. Details of how interactions between shells can be used to determine (1) a long spin-lattice $T_1$ relaxation time of the substance and (2) a magnitude of the applied oscillating field are described below.

As explained above, multi-segment sequences can be advantageously used to generate interaction between a plurality of shells, to detect spins with long spin-lattice relaxation times ($T_1$), and to determine the length of such relaxation times. Measurements produced from such sequences can be used as log quality control indicators. For example, the measurements can be used to warn an operator about incomplete polarization during fast logging operations. Such multi-segment sequences can function as "partial" saturation recovery sequences.

Figure 18:
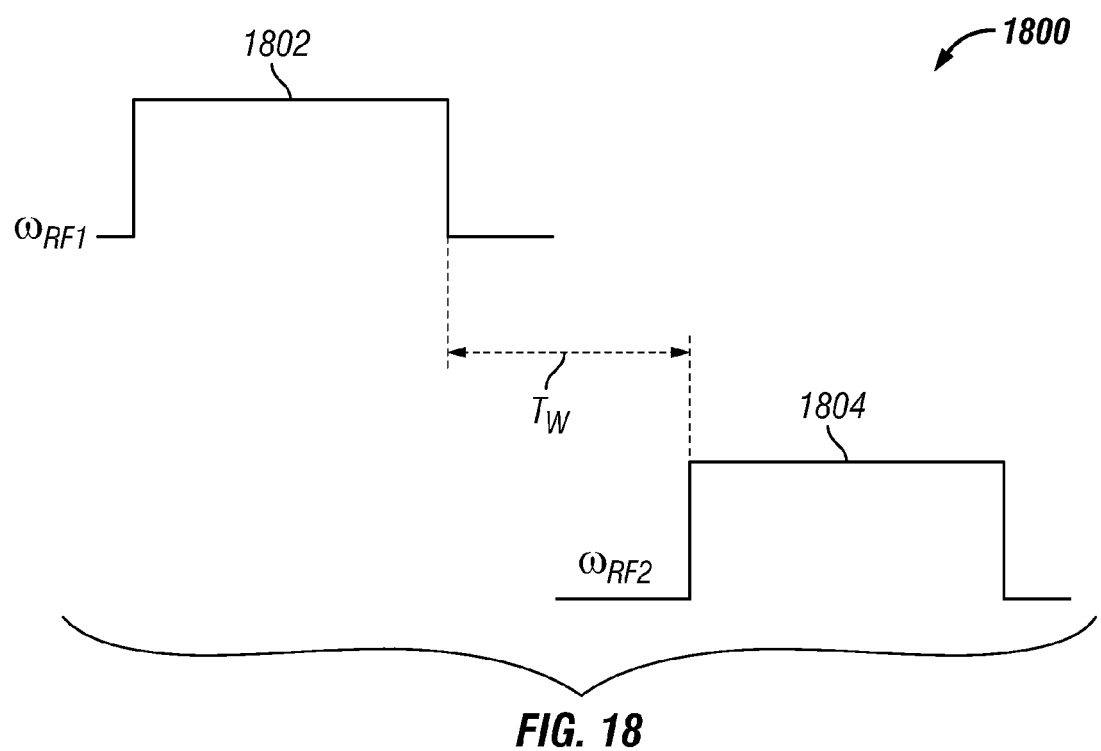
FIG. 18 shows a multi-segment sequence for determining T1 relaxation time in accordance with one embodiment of the present disclosure.

FIG. 18 shows a multi-segment sequence 1800 for determining $T_1$ relaxation time in accordance with one embodiment of the present disclosure. The sequence 1800 includes a first pulse sequence segment 1802 at a first set of frequencies ($\omega_{RF1}$) that is applied to a first shell and a second pulse sequence segment 1804 at a second set of frequencies ($\omega_{RF2}$) that is applied to a second shell. The pulse sequence 1800 includes a waiting period ($T_W$) between the first pulse sequence segment 1802 and the second pulse sequence segment 1804. In some cases, the waiting period ($T_W$) is between 1 ms and 10 s. In one specific example, the waiting period ($T_W$) is less than 1 s. Also, in another specific example, the pulse sequence segments are CPMG sequences. In some cases, the second pulse sequence segment 1804 is initiated before the first shell reaches thermal equilibrium. If the waiting period ($T_W$) is much greater than the $T_1$ relaxation time, then the first pulse sequence segment 1802 will not have the desired interaction on the second shell. When the waiting period ($T_W$) is approximately equal to or smaller than the $T_1$ relaxation time, then the first pulse sequence segment 1802 will have the desired interaction on the second shell and this interaction can be detected to determine whether the waiting period ($T_W$) is bigger or smaller than the $T_1$ relaxation time.

An average frequency ($\omega_{RF2}$) of the second pulse sequence segment 1804 is offset from an average frequency ($\omega_{RF1}$) of the first pulse sequence segment 1802 by a frequency difference ($\Delta\omega_{RF}$). In various embodiments, the frequency difference is less than 10$\omega_1$. In some specific embodiments, the frequency difference is between 1$\omega_1$ and 4$\omega_1$. The amount of interaction between the first shell and the second shell can be controlled by varying the frequency difference ($\Delta\omega_{RF}$) and/or the waiting period ($T_W$). The first pulse sequence segment 1802 generates an asymmetry in at least a portion of the longitudinal magnetization with respect to a static frequency offset axis of the second pulse sequence segment 1804. The asymmetry introduces a non-zero imaginary component into echoes generated within the second shell. This imaginary component decays exponentially as $\exp(-T_W/T_1)$. This imaginary component of the resonant signal within the second shell is detected. The imaginary component and the known value of the waiting period ($T_W$) can be used to determine the $T_1$ relaxation time. In some cases, the partial saturation recovery sequences advantageously increase SNR for nuclei with long $T_1$ components. In contrast, in conventional saturation recovery sequences, SNR approaches zero as $T_1$ approaches infinity.

Figure 20:
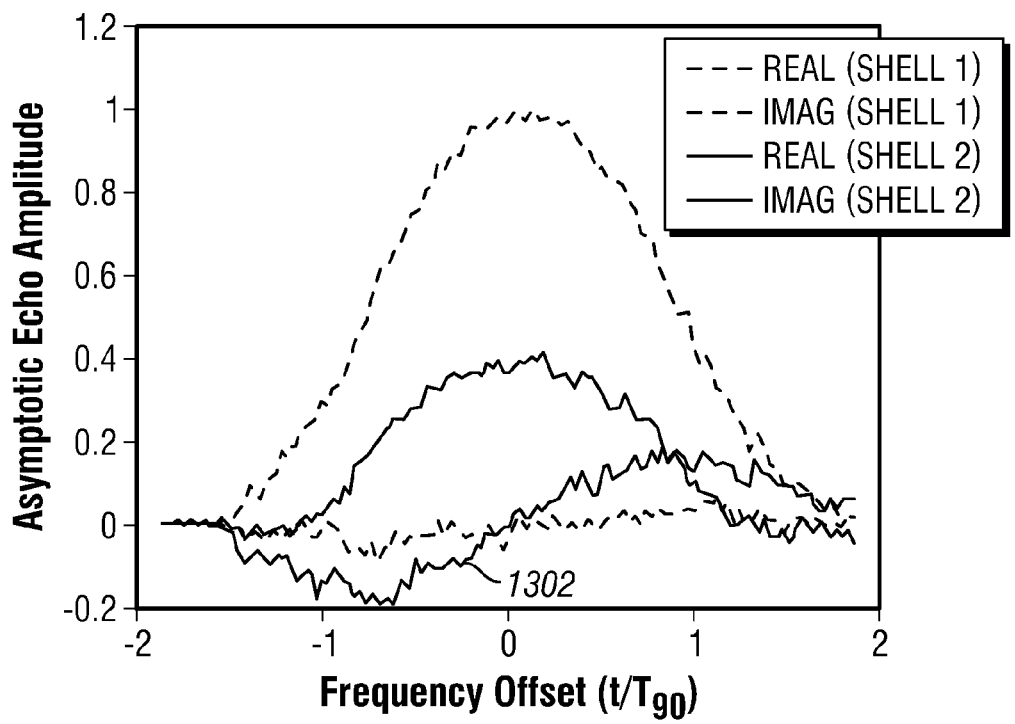
FIG. 20 shows a measured plot of asymptotic echo amplitude versus echo acquisition time in accordance with one embodiment of the present disclosure.

FIG. 19 shows a simulated plot 1900 of asymptotic echo amplitude versus echo acquisition time in accordance with one embodiment of the present disclosure, while FIG. 20 shows a measured plot 2000 of asymptotic echo amplitude versus echo acquisition time in accordance with one embodiment of the present disclosure. In particular, the Figures show simulated and measured asymptotic echo amplitudes for a partial saturation recovery sequence. In this case, the sequence includes a waiting period of 10 ms between segments (e.g., $T_W$=10 ms). Each pulse sequence segment was a CPMG sequence. The partial saturation recovery sequence was applied to a doped-water sample. The doped-water sample had a $T_1$ and $T_2$ relaxation time of approximately 120 ms (e.g., $T_1 \approx T_2$=120 ms). The pulse sequence was applied to the sample using a broadband NMR system. The Larmor frequency of the first shell was 0.94 MHz and the frequency difference between the shells was 10 kHz (e.g., $\Delta\omega_{RF}/2\pi$=10 kHz). The excitation pulses for each segment were 70 μs in length (e.g., $T_{90}$=70 μs). The echo spacing within each shell was 4 ms (e.g., $T_E$=4 ms) and the pulse sequence was repeated 128 times (e.g., N=128). As shown in FIGS. 19 and 20, the measured asymptotic echo amplitude corresponds well with the simulated asymptotic echo amplitude for the partial saturation recovery sequence. The asymptotic echo produced by the second shell has a non-zero imaginary component 1902. As explained above, the non-zero imaginary component can be used to determine the $T_1$ relaxation time. Further measurements demonstrated similar favorable results for various different values of the waiting period ($T_W$).

As explained above, in another illustrative example, a multi-segment sequence is used to determine the magnitude of an applied oscillating field ($B_1$). Various embodiments of the present disclosure are directed to a fast and accurate method that determines an average magnitude of an RF magnetic field ($B_1$), or equivalently a nutation frequency ($\omega_1 = \gamma B_1$), that is applied by an NMR system. The multi-segment sequence uses the Bloch-Siegert phase shift (B-S phase shift) to determine the magnitude of an applied oscillating field.

Figure 21:
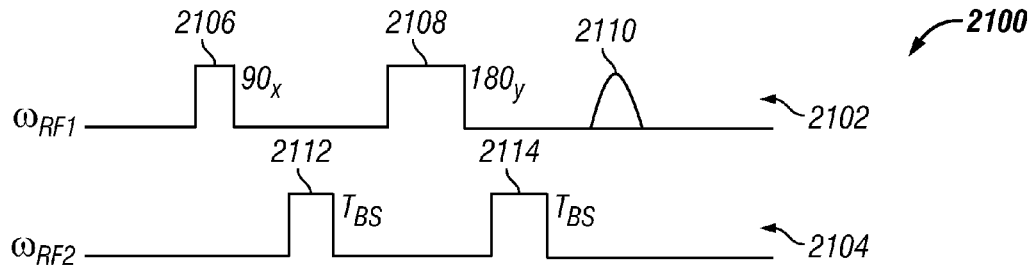
FIG. 21 shows a multi-segment sequence for determining an applied oscillating field ($B_1$) in accordance with one embodiment of the present disclosure.

FIG. 21 shows a multi-segment sequence 2100 for determining an applied oscillating field ($B_1$). The sequence 2100 includes a first pulse sequence segment 2102 at a first frequency ($\omega_{RF1}$) (e.g., set of frequencies) and a second off resonant pulse sequence segment 2104 at a second frequency ($\omega_{RF2}$) (e.g., set of frequencies). The difference between the two pulses is $\Delta\omega_{RF1}$. In the pulse sequence segment of FIG. 21, the first segment 2102 includes an excitation pulse 2106, a refocusing pulse 2108 and an echo 2110. In various embodiments, the excitation pulses have a length of $T_{90}$ and the refocusing pulses have a length of $T_{180}$. In this case, the first segment 2102 is a Hahn spin-echo sequence (SE). The second segment 2104 includes an off-resonant pulse 2112 that is applied after the excitation pulse 2106. The second segment 2104 also includes another off-resonant pulse 2114 that is applied after the refocusing pulse 2108. The off-resonant pulses each have a length of $T_{BS}$.

Figure 22:
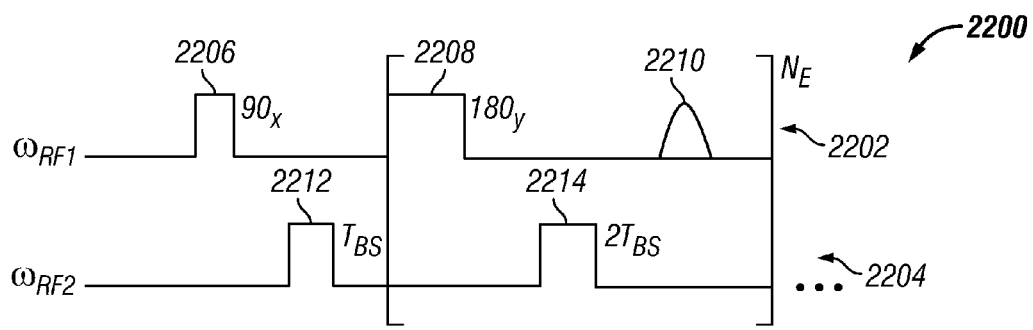
FIG. 22 shows a multi-segment sequence for determining an applied oscillating field ($B_1$) in accordance with another embodiment of the present disclosure.

FIG. 22 shows another multi-segment sequence 2200 for measuring an applied oscillating field ($B_1$). In this embodiment, the sequence 2200 includes a first pulse sequence segment 2202 at a first frequency ($\omega_{RF1}$) and a second off-resonant pulse sequence segment 2204 at a second frequency ($\omega_{RF2}$). The first segment 2202 includes an excitation pulse 2206 and refocusing pulse 2208, and an echo 2210. The refocusing pulse 2208 and the echo 2210 (e.g., refocusing cycle) are repeated a number of times ($N_E$). In this case, the first segment is a CPMG sequence. The second segment 2204 includes a first off-resonant pulse 2212 that is applied after the excitation pulse 2206 and another second off-resonant pulse 2214 that is applied after the refocusing pulse 2208. As shown in FIG. 22, the pulse sequence segments 2202, 2204 are interposed within each other. In this case, the second off-resonant pulse 2212 is repeated after each refocusing pulse 2208 (e.g., $N_E$ number of times). Also, in this case, the first off-resonant pulse 2212 has a length of $T_{BS}$, while the second off-resonant pulse 2214 has a length of 2 $T_{BS}$.

Figure 23:
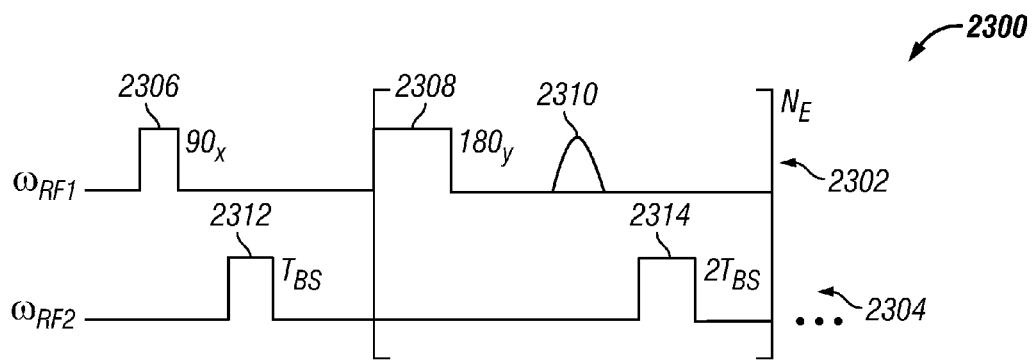
FIG. 23 shows a multi-segment sequence for determining an applied oscillating field ($B_1$) in accordance with yet another embodiment of the present disclosure.

FIG. 23 shows another multi-segment sequence 2300 for measuring an applied oscillating field ($B_1$). In this case, a second off resonant pulse sequence segment 2304 includes a second off-resonant pulse 2314 that is applied after an echo 2310. The multi-segment sequences shown in FIGS. 21-23 are specific examples and the embodiments presented herein are not limited to any specific sequences and pulse lengths.

In these specific examples, the pulses have a length of $T_{BS}$ and 2 $T_{BS}$ and the pulses introduce B-S phase shifts that are $\varphi_{BS}$ and 2 $\varphi_{BS}$, respectively (e.g., because $\varphi_{BS} = \omega_1^2 T_{BS}/(2\Delta\omega_{RF})$). Such B-S phase shifts can also be produced by varying other pulse characteristics. In particular, such phase shifts can be produced by changing the pulse length ($T_{BS}$), the pulse amplitude ($\omega_1$), or the frequency offset ($\Delta\omega_{RF}$).

In illustrative embodiments, the multi-segment sequences (e.g., 2100, 2200, 2300, are applied a plurality of times (e.g., a number of "scans"). In some embodiments, the pulses have equal and opposite frequency offsets ($\pm\Delta\omega_{RF}$), which removes the dependence of B-S phase shift ($\varphi_{BS}$) on resonant frequency offset, as shown in Equation 24 below. For example, in a first application of a multi-segment sequence (e.g., a first scan), the frequency offset is $\pm\Delta\omega_{RF}$, while in a second application of the multi-segment sequence (e.g., second scan) the frequency offset is $-\Delta\omega_{RF}$.

The first and second off-resonant pulses induce a B-S phase shift ($\varphi_{BS}$) in the echoes of the resonant signal and this B-S phase shift can be used to determine the applied oscillating field ($B_1$). As explained above, the pulse sequences are applied using an NMR system. In some embodiments, the NMR system is a broadband system that applies off-resonant pulses with a frequency offset ($\Delta\omega_{RF}$) of several $\omega_1$ from the Larmor frequency. For example, at a Larmor frequency of 2 MHz and a nutation frequency $\omega_1 = 2\pi \times 10$ kHz (corresponding to $T_{90}$=25 μs), the offset frequency might be $8\omega_1 = 2\pi \times 80$ kHz. The NMR system also includes a coil to excite nuclear spins and produce a resonant signal within a shell. The coil produces a time-varying linear RF magnetic field that can be expressed as the sum of two circularly-polarized magnetic fields using the following equation:

$$\cos(\omega_0 t) = \frac{\exp(i\omega_0 t) + \exp(-i\omega_0 t)}{2}, \quad \text{Eq. 12}$$

where $\omega_0$ is the excitation frequency, t is time, and $i=\sqrt{-1}$. The two fields rotate clockwise and counter-clockwise with time. The effect of the counter-clockwise rotating field on the resonant signal is to shift the resonant frequency by an amount ($\omega_{BS}$), as shown by the following equation:

$$\omega_{BS} = \frac{(\gamma B_1)^2}{4\omega_0} \equiv \frac{\omega_1^2}{4\omega_0} \quad \text{Eq. 13}$$

where $B_1$ is the amplitude of each circularly-polarized RF field. The counter-clockwise rotating field can be viewed as being offset in frequency from the resonant (clockwise rotating) field by an amount $\omega_0 - (-\omega_0) = 2\omega_0$. In most cases, $\omega_1$ is much less than $\omega_0$ and this so-called B-S frequency shift is small and can be ignored. However, it is possible to increase the shift by decreasing the frequency offset from $2\omega_0$ to some other value $\Delta\omega_{RF}$. As explained above, off-resonant RF pulses at a frequency ($\omega_0 - \Delta\omega_{RF}$) can be applied for increasing the shift. The effect of such an off-resonant excitation pulse is expressed by the following equation:

$$\omega_{BS} = \frac{\omega_1^2}{2\Delta\omega_{RF}} \qquad \text{Eq. 14}$$

where $\Delta\omega_{RF}$ is the frequency offset of the off-resonant pulse, and $\omega_1$ is $\gamma B_1$ (e.g., $\omega_1 \equiv \gamma B_1$). In illustrative embodiments, the frequency offset ($\Delta\omega_{RF}$) is much larger than $\omega_1$ and the off-resonant pulse does not excite any additional magnetization and thus does not change the amplitude of the spin echo. However, the off-resonant pulse does produce a measurable phase shift. This phase shift effect can be described by using the rotating frame of the pulse. In the rotating frame, the effective magnetic field for the spin packet at $\Delta\omega_{RF}$ is given by:

$$\gamma B_{eff} = \sqrt{(\Delta\omega_{RF})^2 + \omega_1^2} \qquad \text{Eq. 15}$$

The off-resonant pulse modifies the magnitude of the effective field, and thus the precession frequency, from its free-precession value of $\Delta\omega_{RF}$ by an amount that is the B-S phase shift.

Figure 24:
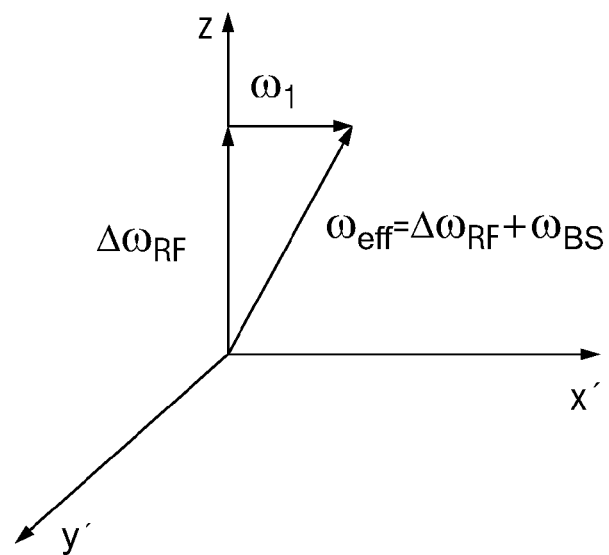
FIG. 24 shows an effective on-resonance magnetic field in a rotating frame of an off-resonant pulse in accordance with yet another embodiment of the present disclosure.

FIG. 24 shows an effective on-resonance magnetic field in the rotating frame of the off-resonant pulse. Using trigonometry, as shown in FIG. 24, the following relationship is determined:

$$\omega_{eff}^2 = (\Delta\omega_{RF} + \omega_{BS})^2 = (\Delta\omega_{RF})^2 + \omega_1^2 \Rightarrow \omega_{BS} \approx \frac{\omega_1^2}{2\Delta\omega_{RF}} \qquad \text{Eq. 16}$$

Since the effective field is approximately aligned to the static field (z-axis) far off-resonance (e.g., when $\Delta\omega_{RF}$ much greater than $\omega_1$), the pulse will produce almost no additional magnetization. However, it will produce additional precession about the z-axis, resulting in a phase shift for the resonant signal at $\Delta\omega_{RF}$ of:

$$\phi_{BS} = \int_0^{TB} \omega_{BS}(t)\,dt = \int_0^{T_{BS}} \frac{(\gamma B_1(t))^2}{2\Delta\omega_{RF}(t)} dt \qquad \text{Eq. 17}$$

where $T_{BS}$ is the duration of the off-resonant pulse. Because the magnitude of the effect decreases only as the inverse of the offset frequency ($\Delta\omega_{RF}$), even frequency-selective pulses applied far off-resonance can produce significant B-S phase shifts. The precise value of the B-S phase shift depends on the amplitude and frequency profile of the off-resonant pulse, as shown in Equation 17. In the case of fixed-amplitude (rectangular) and fixed-frequency pulses, Equation 17 simplifies to:

$$\phi_{BS} = T_{BS}\left(\frac{\omega_1^2}{2\Delta\omega_{RF}}\right) = \theta_{nom}\left(\frac{\omega_1}{2\Delta\omega_{RF}}\right) \qquad \text{Eq. 18}$$

where $\theta_{nom}$ is the nominal tipping angle of the off-resonant pulse (e.g., $\theta_{nom} \equiv \omega_1 T_{BS}$). In an inhomogeneous static field the B-S phase shift is also a function of the resonant frequency offset ($\Delta\omega_0$) within a shell, as shown below:

$$\phi_{BS}(\Delta\omega_0) = \frac{\omega_1^2 T_{BS}}{2(\Delta\omega_{RF} - \Delta\omega_0)} \qquad \text{Eq. 19}$$

Rectangular pulses in a constant static field gradient excite a frequency span of approximately $2\omega_1$, (e.g., the region where $|\Delta\omega_0| \leq \omega_1$), thus defining the shell. In some embodiments, where $\Delta\omega_{RF}$ is much larger than $\omega_1$, $\Delta\omega_{RF}$ is also much larger than $|\Delta\omega_0|$ within the excited volume (e.g., shell). The denominator in Equation 19 can then be expanded as a Taylor series to determine the following relationship:

$$\phi_{BS}(\Delta\omega_0) = T_{BS}\left(\frac{\omega_1^2}{2\Delta\omega_{RF}}\right)\left[1 + \frac{\Delta\omega_0}{\Delta\omega_{RF}} + O(\Delta\omega_0^2)\right] \qquad \text{Eq. 20}$$

The first-order dependence on resonant frequency can be removed by taking the difference between two applications (e.g., scans) of multi-segment sequences (e.g., 2200, 2300) with offset frequencies of $+\Delta\omega_{RF}$ and $-\Delta\omega_{RF}$, as explained above. In this case, the phase shift is approximately constant across the excited sample volume, and there is almost no distortion of the echo shape. The shift is given by:

$$\phi_{BS}(+\Delta\omega_0) - \phi_{BS}(-\Delta\omega_0) = \qquad \text{Eq. 21}$$
$$T_{BS}\left(\frac{\omega_1^2}{\Delta\omega_{RF}}\right)[1 + O(\Delta\omega_0^2)] \approx T_{BS}\left(\frac{\omega_1^2}{\Delta\omega_{RF}}\right)$$

Equation 21 can be re-written to solve for the applied oscillating field ($B_1$) based upon the measured B-S phase shift ($\varphi_{BS}$), the length of the off-resonant pulse ($T_{BS}$), the frequency offset ($\Delta\omega_{RF}$), and the excitation frequency ($\omega_0$), as shown below:

$$B_1 \approx \frac{1}{\gamma}\sqrt{\frac{\Delta\omega_{RF}}{T_{BS}}[\phi_{BS}(+\Delta\omega_0) - \phi_{BS}(-\Delta\omega_0)]} \qquad \text{Eq. 22}$$

The B-S phase shift ($\varphi_{BS}$) can be determined more accurately by increasing the resonant signal. The resonant signal can be increased by generating multiple spin echoes and then adding the echoes. A CPMG sequence, such as the one shown in FIG. 22 or 23, can be used for this purpose. In various embodiments, in order to measure the B-S shift with a CPMG sequence, the CPMG condition is satisfied (e.g., the initial transverse magnetization is aligned with the effective axis of the refocusing cycle) and the initial transverse magnetization is phase-shifted by the first off-resonant pulse. As a result, the effective refocusing axis is also rotated by the same amount. A second off-resonant pulse that creates a phase shift of $2\varphi_{BS}$ can be added to the refocusing cycle for this purpose. This behavior can be obtained by increasing the length of the second off-resonant pulse by a factor of 2, by increasing the amplitude of the off-resonant pulse by a factor of $\sqrt{2}$, or by a combination of both such techniques. In some embodiments, the amplitudes of the off-resonant pulses are constant, thus allowing the sequence to be transmitted using highly-efficient nonlinear power amplifiers. In various embodiments, the second off-resonant pulses within each CPMG refocusing cycle can be applied before the echo (e.g., 2200), or after the echo (e.g., 2300). The spin dynamics of these sequences are similar, except for a reversal in the sign of the phase shift ($\varphi_{BS}$). The application of RF pulses is followed by a certain "dead time" where the receiver is not used (e.g., because of pulse feed through, duplexer switching time or other reasons). The gap between the application of RF pulses and the generation of echoes is larger in the multi-segment sequence shown in FIG. 23 than the multi-segment sequence shown in FIG. 22 and so the sequence in FIG. 22 is less susceptible to dead time effects. As a result, shorter echo spacing is possible, which results in higher SNR and more accurate estimation of the B-S phase shift ($\varphi_{BS}$).

In illustrative embodiments, the second segment and its off-resonant pulses are phase cycled. In some cases, the off-resonant pulses excite small but often non-negligible amounts of transverse magnetization, which produce amplitude variations in the final echo and can make it difficult to measure the phase shift ($\varphi_{BS}$) precisely. This effect can be particularly pronounced for rectangular pulses, which may have poor frequency selectivity. Such unwanted magnetization can be eliminated by phase cycling the off-resonant pulses. Table 1 shows an example of four-part phase cycles that can be used to measure the B-S phase shift for a given frequency offset ($\Delta\omega_{RF}$). The phase shifts in Table 1 are shown in multiples of $\pi/2$. The four-part phase cycles include two phase-alternating pairs (PAPs) with opposite phases for the off-resonant pulses. The cycle is repeated for a frequency offset of $-\Delta\omega_{RF}$ and the phases are subtracted from each other to get the final value of the phase shift ($\varphi_{BS}$), as shown in Equation 22. This differential computation also makes the result independent of the absolute phase of the echo. Thus, in some cases, a total of four PAPs are sufficient for measuring the B-S phase shift.

TABLE 1

| Step | 0 | 1 | 2 | 3 |
| --- | --- | --- | --- | --- |
| Excitation Pulses | 2 | 2 | 0 | 0 |
| Refocusing Pulses | 3 | 3 | 1 | 1 |
| Off-resonant Pulses | 2 | 0 | 2 | 0 |
| Acquisition | 2 | 2 | 0 | 0 |

In illustrative embodiments, the length of the refocusing pulses ($T_{BS}$) is an integer multiple of $2\pi/\Delta\omega_{RF}$. In such embodiments, the rotating frames of the first sequence segment (e.g., CPMG pulses) and the second sequence segment (e.g., off-resonant pulses) are aligned after each off-resonant pulse. In some cases, it may not be possible to ensure that this synchronicity condition is precisely satisfied (e.g., because of pulse transients, limited timing precision of the spectrometer, or other factors). For example, pulse turn-on and turn-off transients may reduce the effective length of both the first off-resonant pulse (e.g., $T_{BS}$) and the second off-resonant pulse (e.g., 2 $T_{BS}$) by the same amount ($\Delta t$). As a result, the effect can be removed by lengthening both pulses by $\Delta t$. In the absence of this correction, there will be a static phase offset between the rotating frames of the off-resonant pulses and the CPMG pulses. As a result, the echo will exhibit the same phase offset, which is given by:

$$\varphi_{off} = 2\Delta\omega_{RF} \times \Delta t \qquad \text{Eq. 23}$$

where the factor of two is used because of two applications of multi-segment sequences with opposite values of $\Delta\omega_{RF}$ (e.g., a first scan at $+\Delta\omega_{RF}$ and a second scan at $-\Delta\omega_{RF}$). Such static phase offsets can be removed by applying the multi-segment sequence with two values of $T_{BS}$: ($T_{BS,1}$) and ($T_{BS,2}$). In such an embodiment, measured phase shifts (including the offset) may be given by $\varphi_1$ and $\varphi_2$. The true phase shifts $\varphi_{BS,1} = \varphi_1 - \varphi_{off}$ and $\varphi_{BS,2} = \varphi_2 - \varphi_{off}$, can be estimated because the shifts linearly depend on $T_{BS}$:

$$\frac{\phi_1 - \phi_{off}}{\phi_2 - \phi_{off}} = \frac{T_{BS,1}}{T_{BS,2}} \Rightarrow \phi_{off} = \frac{\phi_1 T_{BS,2} - \phi_2 T_{BS,1}}{T_{BS,2} - T_{BS,1}} \qquad \text{Eq. 24}$$

The phase of a complex echo signal $z(t) = x(t) + iy(t)$ can be estimated by finding the average in-phase and quadrature components, as follows:

$$\phi = \tan^{-1}\left(\frac{\int_0^{T_{acq}} x(t)\,dt}{\int_0^{T_{acq}} y(t)\,dt}\right) \approx \tan^{-1}\left(\frac{\sum_{i=0}^{N_{acq}-1} x[i]}{\sum_{i=0}^{N_{acq}-1} y[i]}\right) \qquad \text{Eq. 25}$$

where $N_{acq}$ data points are measured within an acquisition window of length $T_{acq}$. The error in this estimate is minimized when the window has approximately the same width as the echo itself. The next process is to estimate $\omega_1$ by inverting the measured B-S phase shift. According to Equation 24, two measurements are sufficient since the phase shift ($\varphi_{BS}$) is dependent on $\omega_1$ and known properties of the off-resonant pulses (e.g., length and frequency offset).

Figure 25:
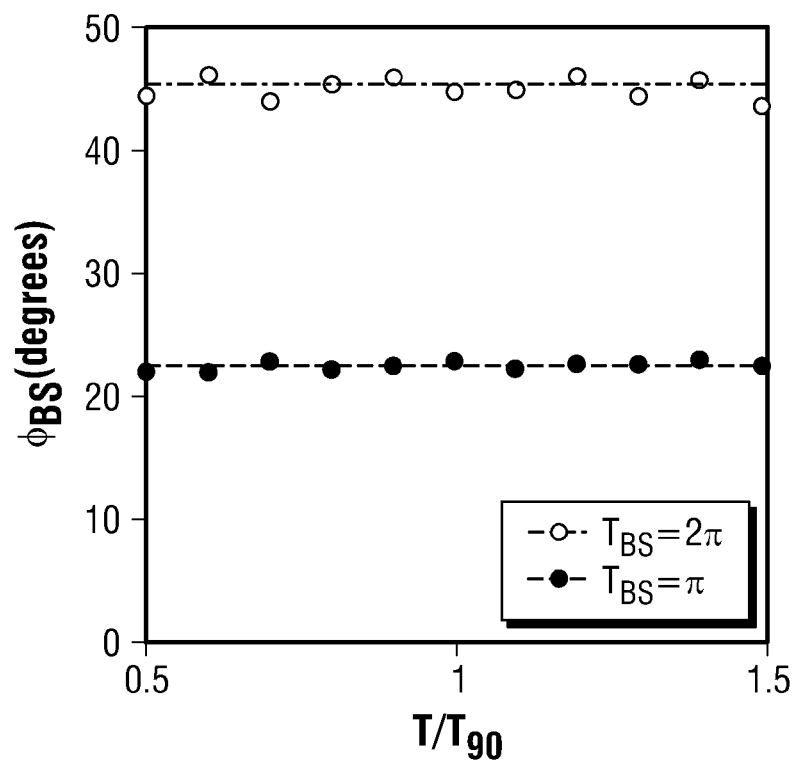
FIG. 25 shows a plot of amplitude of asymptotic echoes as a function of various on-resonant pulse lengths (T) and two values of off-resonant pulse lengths ($T_{BS}$) in accordance with one embodiment of the present disclosure.
Figure 26:
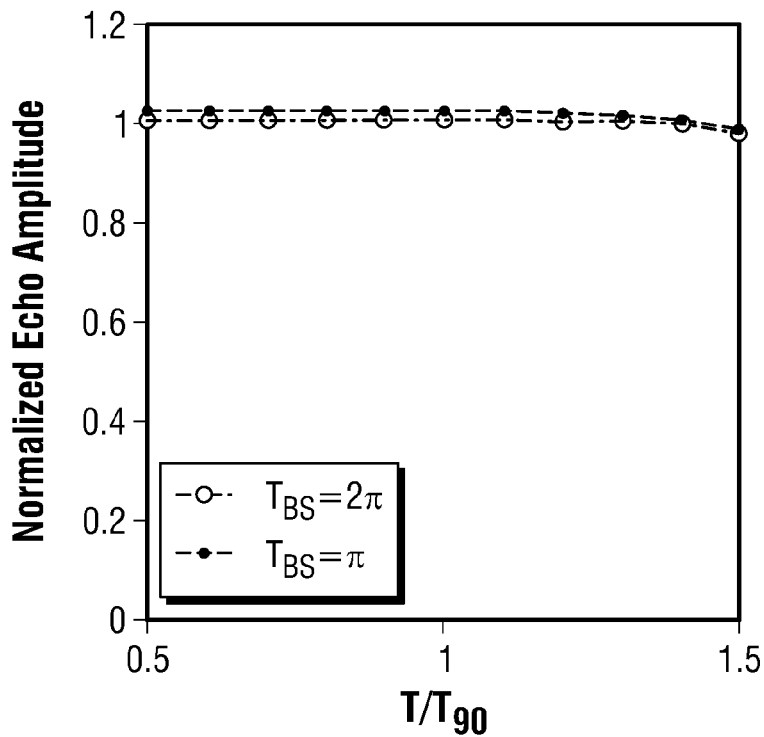
FIG. 26 shows a plot of amplitude of asymptotic echoes as a function of various on-resonant pulse lengths (T) and two values of off-resonant pulse lengths ($T_{BS}$) in accordance with one embodiment of the present disclosure.

In illustrative embodiments, variations in pulse parameters within the first pulse sequence segment, such as flip angles of the excitation and refocusing pulses, do not complicate the inversion process by causing changes in the B-S phase shift ($\varphi_{BS}$). The flip angle of a pulse length (T) can be determined based upon the pulse length (T), the gyromagnetic ratio ($\gamma$), and the magnitude of the applied oscillating field ($B_1$) (e.g., flip angle is equal to $\gamma B_1 T$). FIG. 25 shows phase of asymptotic echoes as a function of various pulse lengths for off-resonant pulses ($T_{BS}$). In particular, FIG. 25 shows that the B-S phase shift ($\varphi_{BS}$) is substantially constant for a wide range of flip angles. As a result, $\omega_1$ can be estimated accurately using one or two phase-shift measurements. FIG. 26 shows amplitude of asymptotic echoes as a function of various pulse lengths for off-resonant pulses ($T_{BS}$). In particular, FIG. 26 shows that the echo amplitude is substantially unaffected by the off-resonant pulses. The plots in FIG. 25 and FIG. 26 were generated by normalizing the nutation frequency (e.g., setting $\omega_1 = 1$), setting the ratio of lengths of the refocusing and excitation pulses within the first sequence segment to 2, and the frequency offset ($\Delta\omega_{RF}$) was set to $8\omega_1$. As a result, the nominal B-S phase shifts expected for $T_{BS} = 2\pi$ and $T_{BS} = \pi$ were $\pi/4$ (45°) and $\pi/8$ (22.5°), respectively. The sequence for measuring the B-S shift was implemented on a broadband NMR system, as described herein. The pulse lengths and delays were set to integer multiples of the frequency offset ($\Delta\omega_{RF}$) to minimize static phase offsets. In addition, a small timing correction (on the order of 1 µs) was applied between the excitation pulse and the first refocusing cycle. This correction ensured that the initial transverse magnetization was aligned with the effective refocusing axis.

Figure 27:
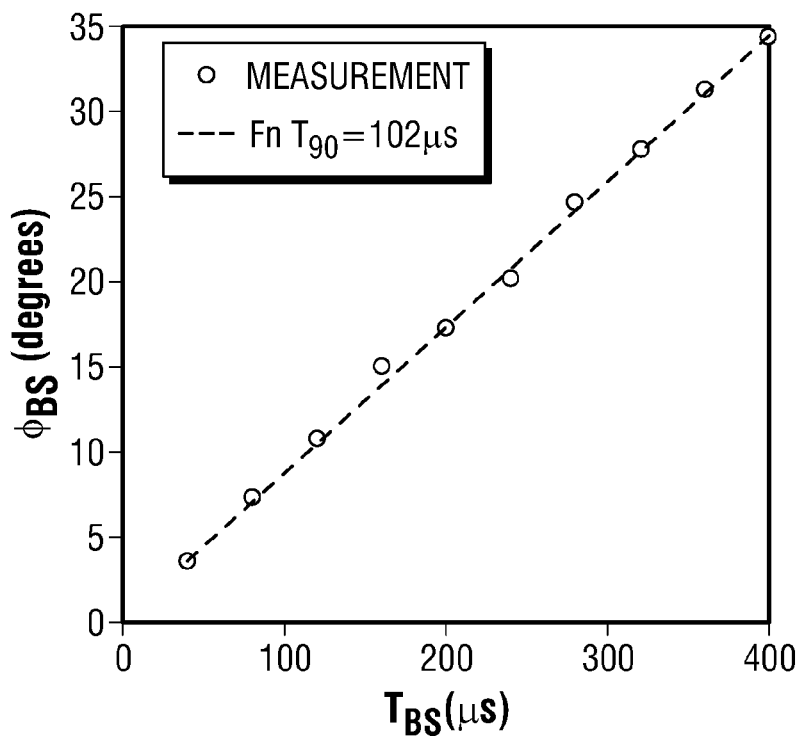
FIG. 27 shows a plot of measured B-S phase shift for a doped-water sample for various off-resonant pulse lengths ($T_{BS}$) in accordance with one embodiment of the present disclosure.

FIG. 27 shows a measured B-S phase shift for a doped-water sample for various off-resonant pulse lengths ($T_{BS}$). The plot in FIG. 27 was generated by applying a multi-segment sequence 2300, as shown in FIG. 23, to a doped-water sample. The doped water had a $T_2$ of approximately 110 ms. The parameters of the multi-segment sequence included: $\omega_{RF}/2\pi=1.48$ MHz; $T_E=2.4$ ms; $N_E=50$; $\Delta\omega_{RF}/2\pi=25$ kHz; excitation pulse length=80 µs; and refocusing pulse length=160 µs. Static phase offset was estimated and removed by using the smallest and largest values of $T_{BS}$, as shown in Equation 24. The remaining phase shift is a linear function of $T_{BS}$ with a slope corresponding to $T_{90}=102$ µs, (e.g., $\omega_1/2\pi=1/(4\,T_{90})=2.45$ kHz). In this case, two values of $T_{BS}$ were used to measure $T_{90}$.

Figure 28:
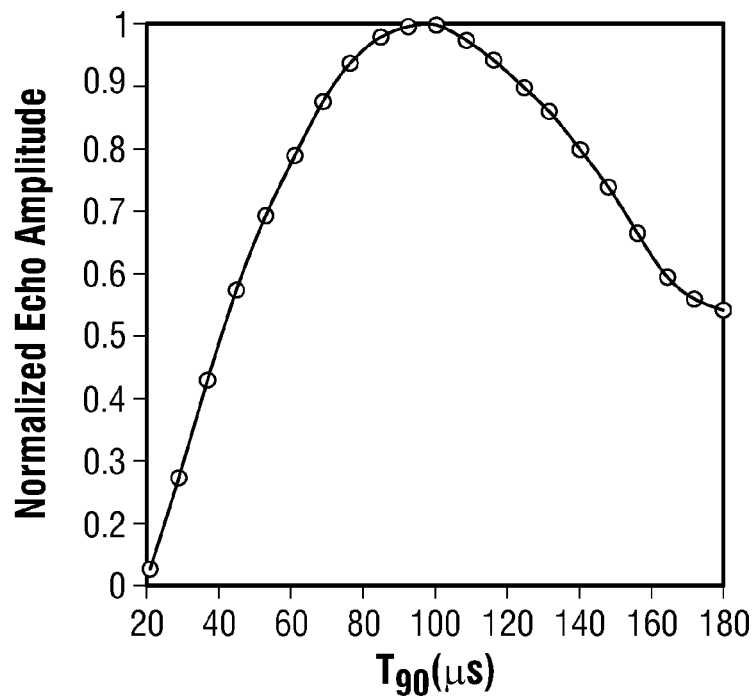
FIG. 28 shows a plot of normalized echo amplitude as a function of excitation pulse length in accordance with one embodiment of the present disclosure.

The results in FIG. 27 were in agreement with conventional approaches for determining the applied oscillating field, such as using measured nutation curves. A measured nutation curve was determined by varying the excitation and refocusing pulse widths within the first segment, while keeping the ratio between them fixed. The resultant echo amplitudes were plotted and the location of the peak was found. Such a measured nutation curve is shown in FIG. 28. As shown in FIGS. 27 and 28, the two techniques described above (e.g., based on measuring the B-S phase shift and a nutation curve, respectively) are in good agreement, except for the fact that the peak of the nutation curve occurs at slightly shorter pulse lengths (e.g., 96 is as opposed to 102 µs). The difference is caused by a spin-dynamics effect, namely, the multiplicity of coherence pathways that contribute to the asymptotic CPMG echo shape in inhomogeneous fields. Similar results were obtained at other offset and Larmor frequencies, showing that the using the B-S phase shift can be a faster and more accurate way to measure the magnitude of the $B_1$ field and calibrate pulse lengths, as compared to conventional methods.

Illustrative embodiments are also directed to determining the magnitude of an applied oscillating field ($B_1$) that is inhomogeneous. In an inhomogeneous field, the measured NMR signal can be determined as a function of both $\omega_1$ and resonant frequency offset ($\Delta\omega_0$), as follows:

$$V_{x,y}(t) \approx \frac{2\chi}{\mu_0} \int\int f(\Delta\omega_0, \omega_1) F(\Delta\omega_0) m_{x,y}(\Delta\omega_0, \omega_1)\omega_{RF}^2 d\Delta\omega_0 d\omega_1, \quad \text{Eq. 26}$$

where $\chi$ is the nuclear susceptibility, $F(\Delta\omega_0)$ is the frequency response of the detection system, $m_{x,y}(\Delta\omega_0,\omega_1)$ is the local transverse magnetization, and the function $f(\Delta\omega_0,\omega_1)$ can be determined from $B_0$ and $B_1$ field maps, a spin density map of the sample, and a coil efficiency factor. In the presence of the B-S phase shift, Equation 26 can be rewritten as:

$$V_{x,y}(t) \approx \frac{2\chi}{\mu_0} \int\int \exp\left(\frac{i\omega_1^2 T_{BS}}{\Delta\omega_{RF}}\right) \quad \text{Eq. 27}$$
$$f(\Delta\omega_0, \omega_1) F(\Delta\omega_0) m_{x,y}(\Delta\omega_0, \omega_1)\omega_{RF}^2 d\Delta\omega_0 d\omega_1$$

Equation 27 above shows that the off-resonant pulses will change both the shape of the echo, as well as the phase of the echo.

Illustrative embodiments of the present disclosure can also detect changes within the applied oscillating field ($B_1$). Magnetic debris often causes significant changes in the static magnetic field distribution $B_0(\vec{r})$ of NMR well-logging tools. As a result, the location and shape of the sensitive volume (shell) changes, leading to calibration errors in basic NMR measurements such as porosity. The multi-segment sequences can be combined with other measurements of $B_1$ (for example, from a pickup loop) to detect such $B_0$ changes. The skin depth at the low Larmor frequencies used in well-logging is usually significantly larger than the depth of investigation. Therefore, the dependence of $B_1$ on salinity is spatially uniform (e.g., can be modeled as a uniform scaling of $B_1(\vec{r})$ by a factor $\alpha$). In particular, the $B_1$ values measured by the multi-segment sequences (at the sensitive volume) and the pickup loop (near the tool) scale by the same factor as a function of salinity. Deviation from uniform scaling indicates that the location of the sensitive volume has changed. The known spatial dependence of $B_1(\vec{r})$ can be used to estimate the magnitude and direction of this shift.

In the embodiments, described above, the shells are spatially separated by using a difference in applied frequency between pulse sequence segments. In additional or alternative embodiments, the shells can also be spatially separated by using different transmit and receive coils, and/or using the motion of the sample.

Various embodiments of such multi-segment sequences for determining the applied oscillating field can be used in both medical and oilfield applications. The sequences can be used to calibrate the amplitude and/or duration of applied RF pulses so that the pulses produce the desired effect on nuclear spins. The calibration is repeated periodically because the magnetic field generated by a given pulse can depend significantly on the presence and properties of the sample. For example, the temperature of the sample may change over time and will have an impact on the magnitude of the applied field. As a result, in some cases, RF pulse lengths in downhole NMR tools are adjusted by 20% or more as a function of temperature and coil quality factor (e.g., which is a function of formation conductivity). Illustrative embodiments of the multi-segment sequences advantageously determine the magnitude of the applied oscillating field quickly and accurately, as compared to conventional methods. For example, one conventional method, as described above, varies RF pulse durations and plots the NMR signal amplitude as a function of pulse duration and determines peaks. This method is time consuming because it requires several NMR measurements (e.g., acquisitions) to determine the peaks. In another example, an inductive pick up loop is used to measure the applied oscillating field. Such a system, however, requires additional components, namely, the additional inductive pick up loop. In addition, the system detects the oscillating field near the location of the loop, which does not usually coincide with the NMR sensitive volume (shell).

Illustrative embodiments of the present disclosure are also directed to applying multi-segment NMR sequences to different sets of atomic nuclei. Such an NMR pulse sequence includes at least a first pulse sequence segment at a first set of frequencies applied to a first set of atomic nuclei, such as carbon nuclei, and a second pulse sequence segment at a second set of frequencies applied to a second set of atomic nuclei, such as sodium nuclei. The second pulse sequence segment is initiated before the first set of atomic nuclei reach thermal equilibrium. In some embodiments, the segments are interposed within each other, as described above. In some cases, the first set of atomic nuclei and the second set of atomic nuclei are from different chemical species (e.g., different atoms, ions or molecules). In other cases, the first set of atomic nuclei and the second set of atomic nuclei are from the same chemical species.

In some embodiments, more than two sets of atomic nuclei are investigated within the same shell using two or more pulse sequence segments. The set of atomic nuclei can be one or more of hydrogen (e.g., $^1$H protons, $^2$H deuterium), fluorine (e.g., $^{19}$F), sodium (e.g., $^{23}$Na) and carbon (e.g., $^{13}$C). Table 2 below shows various properties for each nucleus.

TABLE 2

| Nucleus | $^1$H | $^2$H | $^{19}$F | $^{23}$Na | $^{13}$C |
|---|---|---|---|---|---|
| Spin, I | 1/2 | 1 | 1/2 | 3/2 | 1/2 |
| Gyromagnetic ratio, $\gamma$ (kHz/G) | 4.26 | 0.654 | 4.01 | 1.127 | 1.071 |
| Natural abundance | 99.985% | 0.015% | 100% | 100% | 1.1% |
| Quadrupole moment (mb) | 0 | 2.86 | 0 | 100.6 | 0 |

The frequency for each pulse sequence segment is selected so that segment produces resonant signals within a specific set of atomic nuclei. To this end, the pulse sequence segments are selected to match the Larmor frequency of a specific set of nuclei. The Larmor frequency ($\omega_0$) for a specific set of nuclei can be determined from the magnitude of the static magnetic field ($B_0$) and the gyromagnetic ratio ($\gamma$) of the set of nuclei (e.g., $\omega_0 = \gamma B_0$). The gyromagnetic ratios for several nuclei are shown above in Table 2.

In illustrative embodiments, the pulse sequence segments are applied to a substance and the nuclei within the substance using a broadband NMR system, as further described below. The system can advantageously measure NMR signals from multiple nuclei at different Larmor frequencies in parallel and without physical changes in the hardware. Furthermore, by using a broadband system, the amplitude of the oscillating (RF) magnetic field is inversely proportional to its frequency (e.g., $B_1 \propto 1/\omega_{RF}$) and, in addition, is near resonance (e.g., $\omega_{RF} \approx \omega_0$). Thus, the sequence pulse lengths (T) at any given position in the sample (implying a fixed value of $B_0$) are invariant with the gyromagnetic ratio ($\gamma$) of the atomic nuclei, as shown below:

$$T \propto \frac{1}{\omega_1} = \frac{1}{\gamma B_1} \propto \frac{1}{\gamma\left(\frac{1}{\omega_{RF}}\right)} \approx \frac{1}{\gamma\left(\frac{1}{\omega_0}\right)} = \frac{1}{\gamma\left(\frac{1}{\gamma B_0}\right)} = B_0 \qquad \text{Eq. 28}$$

Accordingly, in some embodiments, an appropriate pulse length can be determined for the first set of atomic nuclei and similar pulse lengths can be used for other sets of atomic nuclei. For example, pulse lengths determined for sensitive nuclei (such as $^1$H) can be reused for less-sensitive nuclei (such as $^{13}$C), and do not have to be determined again. This saves considerable measurement time. Thus, the various different pulse segments can advantageously have pulses with similar lengths (T).

When the NMR system applies a pulse sequence segment having a particular frequency (e.g., over a limited bandwidth), the thickness of the shell will be inversely proportional to gyromagnetic ratio of the nuclei within the substance. This behavior occurs because the coil current and $B_1$ amplitude of the NMR system is inversely proportional to the Larmor frequency (e.g., $B_1 \propto 1/\omega_{RF}$). In one particular embodiment, the gradient ($g_z = |dB_0/dz|$) of the static field within the shell increases linearly with the static field, that is, $g_z \propto B_0$. In this case, we have:

$$B_1 \propto \frac{1}{\omega_0} = \frac{1}{\gamma B_0}, \; g_z \propto B_0 \qquad \text{Eq. 29}$$

$$\Delta z \approx \frac{2B_1}{g_z} \propto \frac{1}{\gamma B_0^2}.$$

where $\Delta z$ is the shell thickness. Due to the relationship in Equation 29, signal amplitude of the resonant signal (in voltage units) scales as:

$$\gamma^3 I(I+1) B_0^2 \Delta z \propto I(I+1) \gamma^2 \qquad \text{Eq. 30}$$

where I is the spin of the atomic nucleus. The number of signal averages (e.g., scans) used to obtain a given SNR in voltage units scales as:

$$N \propto \frac{1}{I^2(I+1)^2 \gamma^4} \qquad \text{Eq. 31}$$

where N is the number of signal averages.

Figure 29:
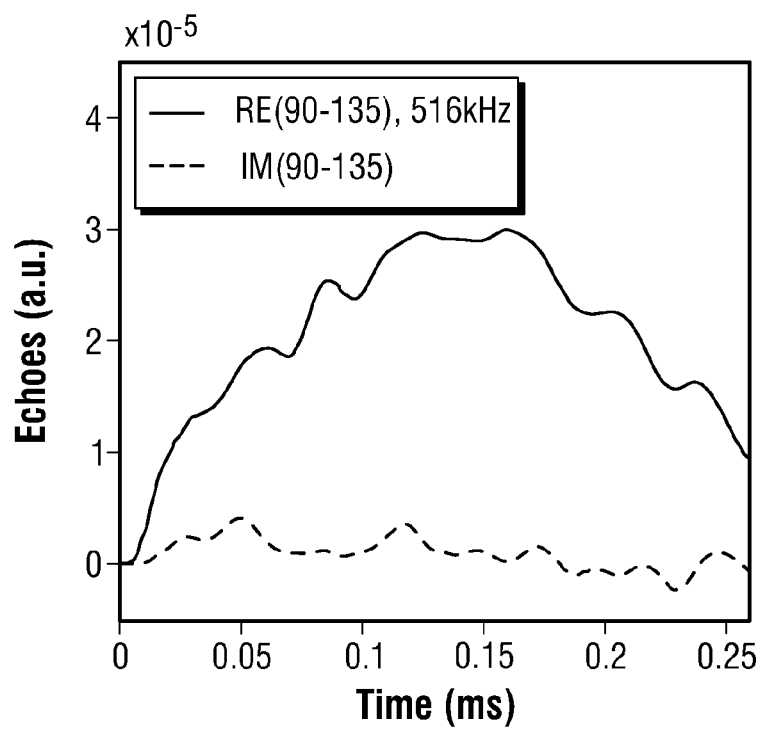
FIG. 29 shows a plot of measured asymptotic CPMG echoes for a sodium sample in accordance with one embodiment of the present disclosure.
Figure 30:
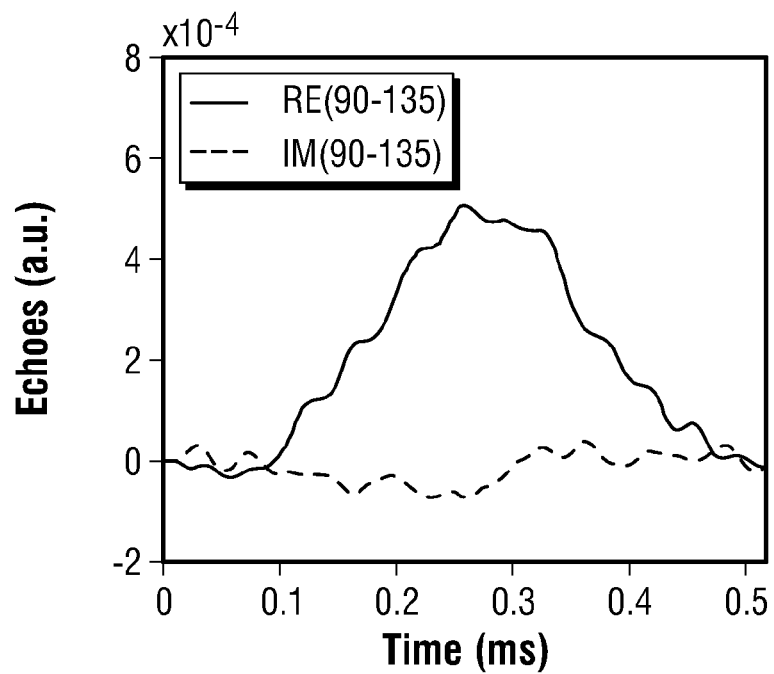
FIG. 30 shows a plot of measured asymptotic CPMG echoes for a deuterium sample in accordance with one embodiment of the present disclosure.

FIGS. 29 and 30 show measured asymptotic CPMG echoes for a sodium sample (250 ppK NaCl (brine)) and a deuterium sample (40% D$_2$O, 60% H$_2$O (heavy water doped with NiCl$_2$)), respectively. FIGS. 29 and 30 were produced by summing the echoes within the resonant signal from each sample. Data was taken at multiple Larmor frequencies with various pulse sequences. The results match spin dynamics simulations well. Additional CPMG measurements (not shown) were used to estimate T$_2$ for these samples. The sodium sample had a proton relaxation time of 2 seconds (T$_{2H} \approx 2$ s) and a sodium relaxation time that was much shorter (T$_{2Na}$=42 ms). The sodium relaxation time case was dominated by quadrupolar interactions. On the other hand, the deuterium sample had a proton relaxation time of T$_{2H}$=200 ms and a deuterium relaxation time that was substantially longer (T$_{2D}$=420 ms). This longer relaxation time occurs in spite of the fact that $^2$H is quadrupolar (I=1). There are two reasons for this longer relaxation time. Firstly, the quadrupolar moment of $^2$H is small, resulting in little quadrupolar relaxation. Secondly, protons have enhanced dipolar relaxation relative to deuterons. In this sample, dipolar relaxation is dominated by interactions between target nuclei and unpaired electrons within paramagnetic ions in solution. As a result, both longitudinal and transverse relaxation rates are proportional to the square of the nuclear gyromagnetic ratio:

$$R_1 = \frac{1}{T_1} \propto I(I+1)(\gamma_n \gamma_e)^2, \qquad \text{Eq. 32}$$

$$R_2 = \frac{1}{T_2} \propto I(I+1)(\gamma_n \gamma_e)^2.$$

where $\gamma_n$ and $\gamma_e$ are the nuclear and electronic gyromagnetic ratios, respectively, and I is the nuclear spin. The significantly higher gyromagnetic ratio of protons relative to deuterons results in enhanced dipolar relaxation for the proton nucleus. FIGS. 29 and 30 were generated using a broadband NMR system. The broadband NMR system applied pulse sequences with rectangular 90 degree excitation pulses and rectangular 135 degree refocusing pulses. The sequence and sample parameters for FIG. 29 included $T_E$=800 µs/900 µs; $T_{acq}$=262 µs; $T_R$=200 ms; and N=16384, where $T_E$ is the echo spacing, $T_{acq}$ is the acquisition time, $T_R$ is the time between repetitions of the sequences, and N is the number of times the sequences are repeated. The sequence and sample parameters for FIG. 30 included $\omega_0$=2π×342 kHz; $T_E$=1 ms; $T_{acq}$=262 µs, $T_R$=1.0 s, and N=1024.

Figure 31:
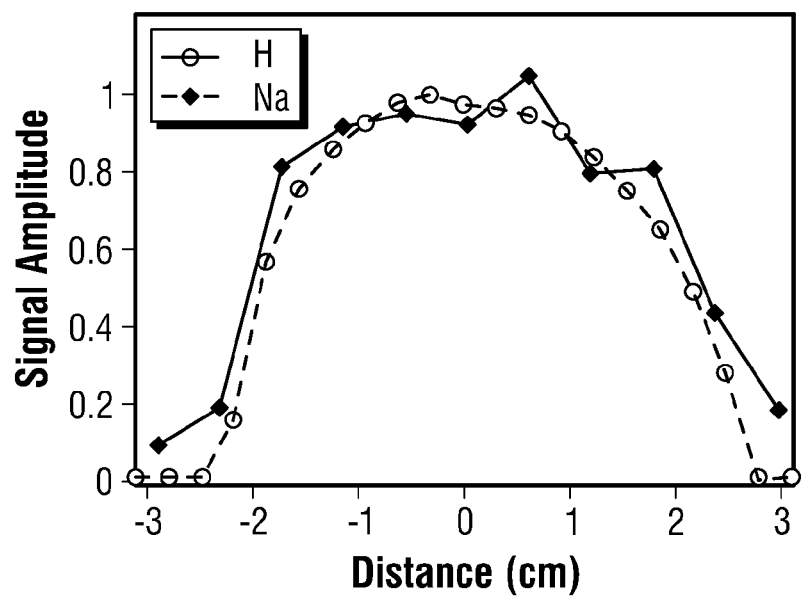
FIG. 31 shows a plot of measured proton and sodium depth profiles for a brine sample in accordance with one embodiment of the present disclosure.

Illustrative embodiments of the present invention are also directed to depth profiling of multiple nuclei. FIG. 31 shows the measured proton and sodium depth profiles of a brine sample. The wait times between successive scans can be kept short (e.g., less than 200 ms) for measuring sodium nuclei because sodium nuclei have short $T_1$ times. As a result, the sodium profile can be measured relatively quickly (e.g., only 2.5 times slower than the proton profile, in this case). Such sodium profiles can be used to estimate the brine content in a mixture of oil and brine as a function of radial distance from the tool (depth) during NMR well logging. Such a measurement can be referred to as an "NMR salinity log." FIG. 31 shows a multi-nuclear depth profile that was generated using a broadband system. In particular, FIG. 31 shows a normalized proton and sodium depth profiles of a 250 ppK brine solution located at a center frequency of 2.0 MHz for the proton nuclei and 529 kHz for the sodium nuclei. The experimental time required to acquire each point in the profiles was 64 seconds (proton, N=16) and 150 seconds (sodium, N=1024).

Illustrative embodiments of the present disclosure use broadband NMR electronics to apply multi-segment sequences at different frequencies and/or to detect resonant signals at different frequencies. Conventional narrowband NMR electronics can switch frequencies at the end of a complete pulse sequence, such as a CPMG sequence. To switch between frequencies, such conventional narrowband systems use banks of fixed capacitors and mechanical switches that are coupled to a coil. The mechanical switches tune the coil to different frequencies by switching between a pre-set number of fixed capacitors. Such narrowband systems suffer from several disadvantages. Firstly, the switches within the capacitor banks introduce noise into the NMR measurement. Secondly, a predetermined discrete set of narrowband frequencies can be set because each frequency is dependent on a separate capacitor. Thirdly, the frequency switching process introduces dynamics and may not maintain phase coherence of the pulse sequence waveform. Fourthly, the switching process is slow (e.g., 10-100 ms switching times).

Exemplary embodiments presented herein avoid such problems. Broadband NMR electronics can switch between frequencies that are outside a natural resonant frequency bandwidth of a coil with a tuned circuit. In other words, broadband electronics do not depend on tuning a coil to set a particular frequency. In contrast to conventional narrowband systems, which use mechanical switches and banks of fixed capacitors to tune the coil, various embodiments of the broadband electronics described herein achieve multi-frequency operation without a need for hardware modulation (e.g., switching between fixed capacitors or tuning between variable capacitors). In this manner, the broadband electronics are frequency insensitive and allow the pulse sequence frequency to be dynamically varied by a spectrometer while maintaining phase coherence of an output waveform.

As explained above, in some cases, the broadband NMR electronics can switch between frequencies with a frequency difference ($\Delta\omega_{RF}$) as great as 10% of an initial applied frequency. In various other embodiments, the frequency can be even greater (e.g., 20% 30% or 50%). Also, in some embodiments, the broadband NMR electronics can switch between frequencies in less than 5 µs. In yet further embodiments, the broadband NMR electronics can switch between frequencies in less than 20 µs or 50 µs. Furthermore, in some embodiments, the broadband NMR electronics can operate within a frequency range of 100 kHz and 3.2 MHz.

Figure 32A:
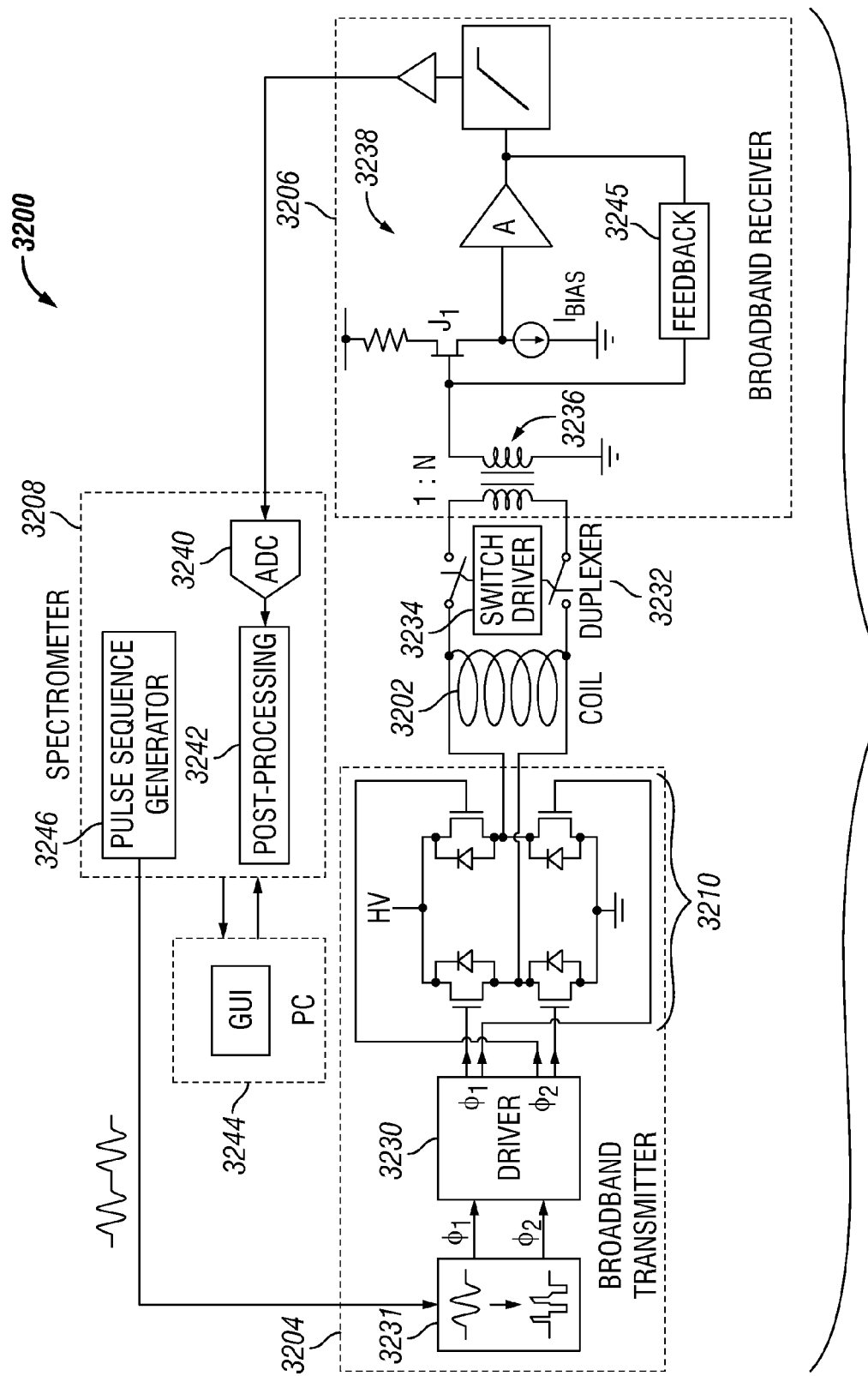
FIG. 32A shows a broadband NMR device in accordance with one embodiment of the present disclosure.

FIG. 32A shows broadband NMR device 3200 in accordance with one embodiment of the present disclosure. The broadband NMR device 3200 includes a coil 3202 that is coupled to broadband NMR electronics 3204, 3206, 3208. A sample substance is located inside and/or outside of the coil 3202. The broadband NMR electronics include a broadband transmitter 3204 and a broadband receiver 3206. Each of the transmitter 3204 and the receiver 3206 are coupled to the coil 3202.

Figure 32B:
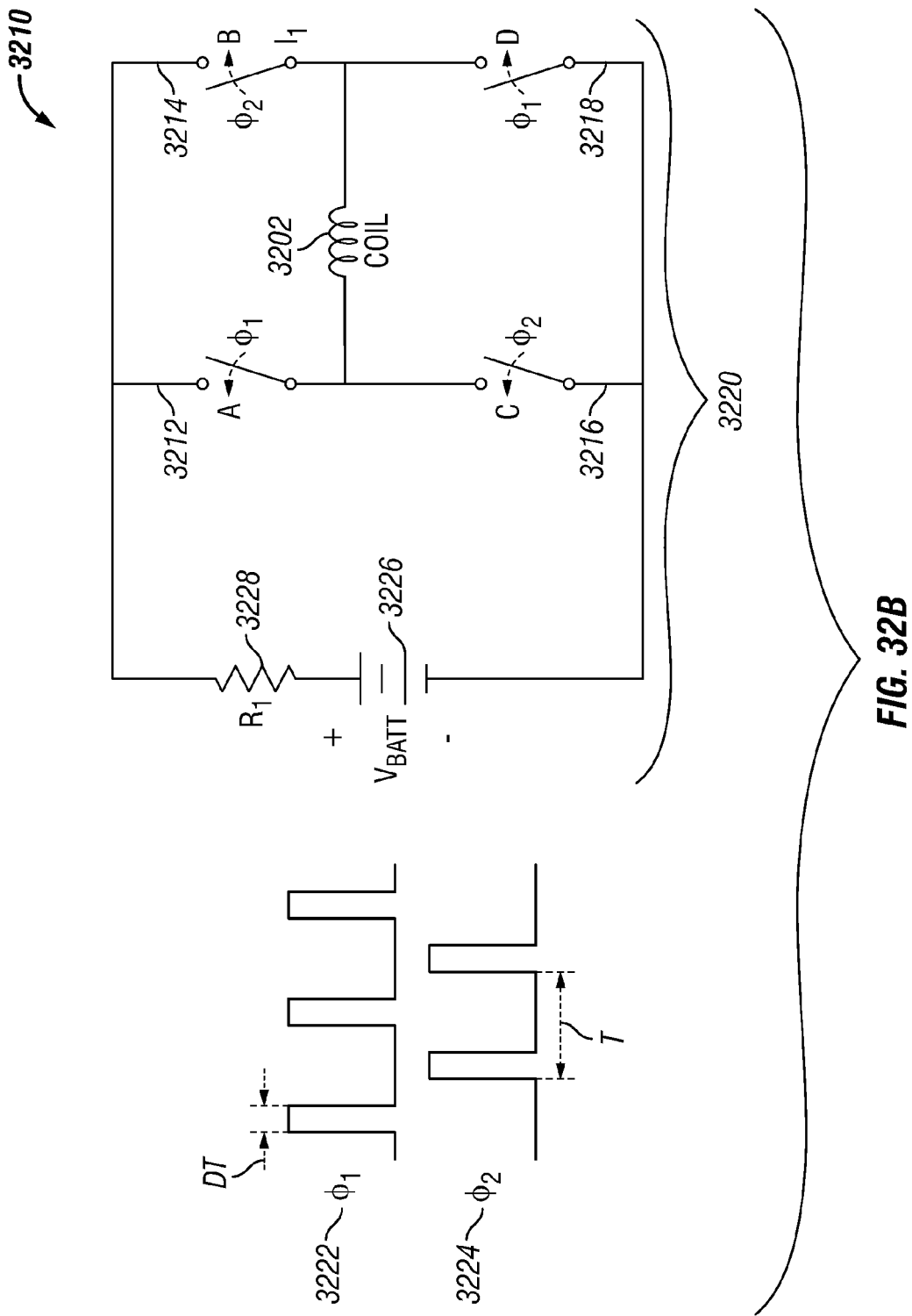
FIG. 32B shows a non-resonant NMR transmitter circuit in accordance with one embodiment of the present disclosure.

The broadband NMR transmitter 3204 includes a non-resonant NMR transmitter circuit 3210 that is coupled to the coil 3202. The transmitter circuit 3204 is "non-resonant" because the resonant frequency of the circuit does not need to match the Larmor frequency of interest. In contrast, as explained above, conventional circuits set their resonant frequencies to match the Larmor frequency of interest by selecting a particular capacitance for the circuit. Although the non-resonant transmitter circuit 3210 and coil 3202 may use capacitors and have some associated capacitance, this capacitance is not specifically selected to match a Larmor frequency of interest. FIG. 32B shows a non-resonant NMR transmitter circuit 3210 in accordance with one specific embodiment of the present disclosure. In this specific example, the NMR transmitter circuit 3210 includes a set of four switches: A 3212, B 3214, C 3216 and D 3218. These switches control the timing and the direction of the current flow in the coil. Turning these switches on and off using a certain switching logic generates an alternating current in the coil and thus produces RF irradiation. The switching logic often includes a period of positive current followed by a period of negative current, simulating a sinusoidal waveform. Repeating this pattern at a given frequency allows the generation of RF power at a particular frequency. In one particular embodiment, the switches 3212, 3214, 3216, 3218 are transistors, such as metal-oxide-semiconductor field-effect transistors (MOSFET), insulated gate bi-polar transistors (IGBT), or various other switches based upon the high frequency switching (HFS) family. In various embodiments, the switches can switch at less than 10 ns. The switches 3212, 3214, 3216, 3218 are arranged in a circuit 3220 known as an H-bridge, as shown in FIG. 32B. In one embodiment, the switches 3212, 3214, 3216, 3218 are controlled by two non-overlapping digital signals denoted as $\varphi_1$ and $\varphi_2$ 3222, 3224. The signals $\varphi_1$ and $\varphi_2$ 3222, 3224 include a switching logic, which is used to drive the two sets of switches, (A and D) and (B and C), such that a voltage source $V_{batt}$ 3226 is connected with alternating polarity across the coil 3202 and an oscillatory coil current ($I_1$) is created. A load resistor $R_1$ 3228 or fuse can be used in series with the voltage source to limit the current that is applied to the switches 3212, 3214, 3216, 3218. The digital signals denoted as $\varphi_1$ and $\varphi_2$ 3222, 3224 are used to control the switches 3212, 3214, 3216, 3218 and a desired frequency of an NMR sequence (e.g., a multi-segment sequence) is achieved by repeating these signals at the desired frequency. In some embodiments, other digital signals can be used to control each of the switches 3212, 3214, 3216, 3218 individually. For example, the signals may include high components (e.g., $\varphi_{1H}$ and $\varphi_{2H}$) that control the high-side switches 3212, 3214 and low components (e.g., $\varphi_{1L}$ and $\varphi_{2L}$) that control the low-side switches 3216, 3218.

The broadband NMR transmitter 3204 also includes a driver 3230 that is coupled to the non-resonant NMR transmitter circuit 3210. In one particular embodiment, the driver 3230 can be a computer processor. The driver 3230 is used to control the switches 3212, 3214, 3216, 3218 within the transmitter circuit 3210. The driver 3230 switches the switches 3210 according to the switching logic within the digital signals (e.g., $\varphi_1$ and $\varphi_2$). In various embodiments, the driver 3230 also receives NMR pulse sequences from an NMR spectrometer 3208. In some embodiments, the NMR pulse sequences are sent along a plurality of channels. An adder circuit (not shown) can be used to combine the plurality of channels. Also, in various embodiments, the transmitter 3204 includes a comparator 3231 for receiving the NMR pulse sequences from the spectrometer 3208 and generating a square waveform that is then provided to the driver 3230. The NMR pulse sequences can be translated by the driver 3230 into the particular switching logic by selecting positive and negative waveforms of the NMR pulse sequences and then conditioning the waveforms to an appropriate voltage. In this manner, modulating hardware, such as a tuning capacitor, is not necessary in order to achieve a particular frequency. Instead, the frequency is modulated directly by the spectrometer 3208.

The coil 3202 is also coupled to the broadband NMR receiver 3204 so that NMR resonant signals can be detected within the sample. The coil 3202 is coupled to the broadband receiver 3206 using a duplexer 3232. The duplexer 3232 decouples the receiver 3206 from the coil 3202 when the coil is operating in a transmitting mode (e.g., transmitting an NMR pulse sequence). In this manner, the duplexer 3232 protects the receiver 3206 during a transmitting mode. In one particular embodiment, the duplexer 3232 includes switches and a switch driver 3234 that opens the switches during a transmitting mode and closes the switches during a receiving mode of operation. In various embodiments, the duplexer 3232 includes two back-to-back field effect transistors (FETs) that are controlled by an isolated driver circuit. This configuration produces a bidirectional and broadband switch. The switch is bidirectional because the state of the switch is independent of the polarity of the voltage on the coil. For example, such a switch will remain OFF regardless of whether the voltage across the coil is positive or negative. The switch is broadband because a reference voltage for the driver is not connected to the same ground terminal as the remainder of the driver circuit. Control signals can be passed to the switch using various isolated signal transmission methods, such as magnetic transmission methods (e.g., using a transformer) or optical transmission methods (e.g., using an optoisolator). In some embodiments, a duplexer is not used when the device 3200 includes separate transmit and receive coils.

Figure 32C:
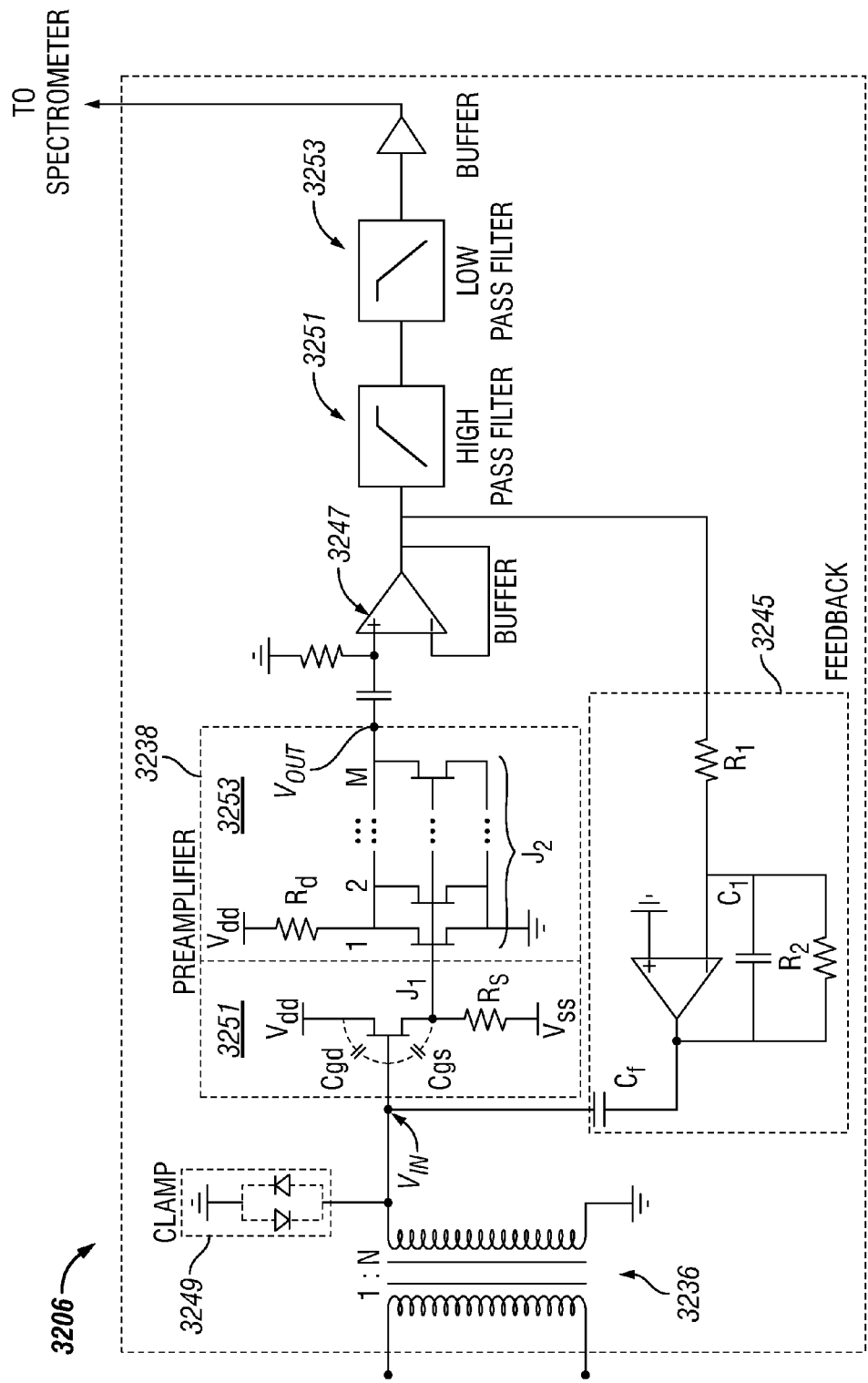
FIG. 32C shows a broadband NMR receiver in accordance with one embodiment of the present disclosure.

FIG. 32C shows the broadband NMR receiver 3206 in more detail. The broadband NMR receiver can receive and process resonant NMR signals over a broad frequency range. In some embodiments, the ratio of the highest operating frequency and lowest operating frequency is greater than 5. In various embodiments, this ratio is as great as 30 or 50. The highest operating frequency and lowest operating frequency are defined by the frequency range over which the performance of the receiver is satisfactory for its application. For example, in one case, the frequency range is the range over which the input-referred noise of the receiver is less than that of a 1-$\Omega$ resistor. This level of noise is considered adequate for NMR coils with resistance of 1$\Omega$ or larger. In various embodiments, the frequency range satisfying this condition is 3 MHz to 0.1 MHz Various embodiments of the broadband NMR receiver 3206 include a transformer 3236 that receives the NMR resonant signal from the coil 3202 and amplifies the signal by proving a voltage gain. In some embodiments, the transformer is directly coupled to the duplexer 3232. The transformer 3236 may be a step-up transformer with a turn ratio of 1:N. The turn ratio may be in the range of 1:2 to 1:10. For low frequency operation (e.g., below 5 MHz), the transformer 3236 may include a soft magnetic core to increase the inductance and performance of the transformer. However, in some embodiments, higher turn ratios can also be used. For higher frequency operation (e.g., above 5 MHz), a transformer 3236 without a magnetic core can be used. In illustrative embodiments, the transformer 3236 includes a low insertion loss and a bandwidth that significantly exceeds the highest operating frequency of the receiver 3206. In some embodiments, for transformers 3236 with magnetic cores, a magnetic shield may be installed around the transformer. The shield reduces the magnetic field projected from the NMR magnet into the transformer 3236, which improves the performance of the transformer.

The receiver 3206 also includes a preamplifier 3238 that follows the transformer 3236. In some embodiments, the preamplifier is directly coupled to the transformer 3236. The transformer 3236 provides a broadband passive and low-noise voltage gain of a NMR signal that is detected at the coil 3202. This voltage gain occurs before the preamplifier 3238. In some cases, such a transformer-coupled topology results in a low noise figure (NF) over a wide frequency range. In one specific example, the transformer 3236 has a turn ratio of 1:10 to amplify an input signal above a noise floor of the preamplifier 3238. Such a configuration can produce a low input-referred noise at frequencies up to 10 MHz (e.g., 0.1 nV/Hz$^{1/2}$, which is equal to the thermal noise produced by a 0.6$\Omega$ resistor at 300 K). After the transformer, the NMR signal is passed to the preamplifier 3238, which further amplifies the NMR signal.

The preamplifier 3238 includes a common-drain amplifier stage 3251 and a common-source amplifier stage 3253. In FIG. 32C, the common-drain amplifier stage 3251 includes a transistor ($J_1$) that is configured as a common-drain amplifier. The transistor ($J_1$) has an input signal fed at the gate of the transistor and an output signal taken from the source of the transistor (e.g., also known as a source follower). In one specific embodiment, the transistor ($J_1$) is a junction gate field-effect transistor (JFET). A gate-source capacitance ($C_{gs}$) and a gate-drain capacitance ($C_{gd}$) are intrinsic to the transistor ($J_1$). By configuring the transistor ($J_1$) as a source follower, the preamplifier 3238 advantageously applies the gate-drain capacitance ($C_{gd}$) at an input terminal of the transistor. The gate-drain capacitance ($C_{gd}$) is much smaller than the gate-source capacitance ($C_{gs}$) when the transistor ($J_1$) is biased in its usual region of operation (e.g., known as saturation). The maximum RF frequency that can be amplified by the preamplifier 3238 with low noise (e.g., useful bandwidth of the preamplifier) is proportional to:

$$1/\sqrt{C_{input}} \qquad \text{Eq. 33}$$

where $C_{input}$ is the total capacitance at the input of the transistor ($J_1$). The transistor ($J_1$) contributes a significant portion of total capacitance at the input of the transistor ($C_{input}$), so reducing its contribution from the gate-source capacitance ($C_{gs}$) to the gate-drain capacitance ($C_{gd}$) significantly increases the bandwidth of the preamplifier.

In FIG. 32C, a single transistor is shown within the common-drain amplifier stage 3251 of the preamplifier 3238. In other embodiments, however, the common-drain amplifier stage 3251 can include a plurality of common-drain amplifiers that are, for example, coupled in parallel (e.g., a plurality of transistors configured as source followers and coupled in parallel).

Once the NMR signal passes the common-drain amplifier stage 3251, the NMR signal is further amplified by the common-source amplifier stage 3253, which provides a voltage gain to the signal. In the embodiment shown in FIG. 32C, the common-source amplifier stage includes 3253 a number (M) of transistors that are coupled in parallel. In some embodiments, the number of transistors (M) can be between 2 and 10. The common-source stage 3253 reduces the noise that the stage contributes to a level that is 1/M times that contributed by the common-drain amplifier stage 3251 (in power units). By making M much larger than 1, the noise contributed by the stage can be reduced, thus minimizing the noise floor of the preamplifier 3238.

The examples above use JFETs (e.g., as $J_1$ and as $J_2$), however, other types of transistors can also be used, such as bipolar junction transistors (BJT) and/or metal oxide field effect transistors (MOSFET). In various embodiments, the transistors have low current and voltage noise, and also include small capacitances between their terminals.

Figure 32D:
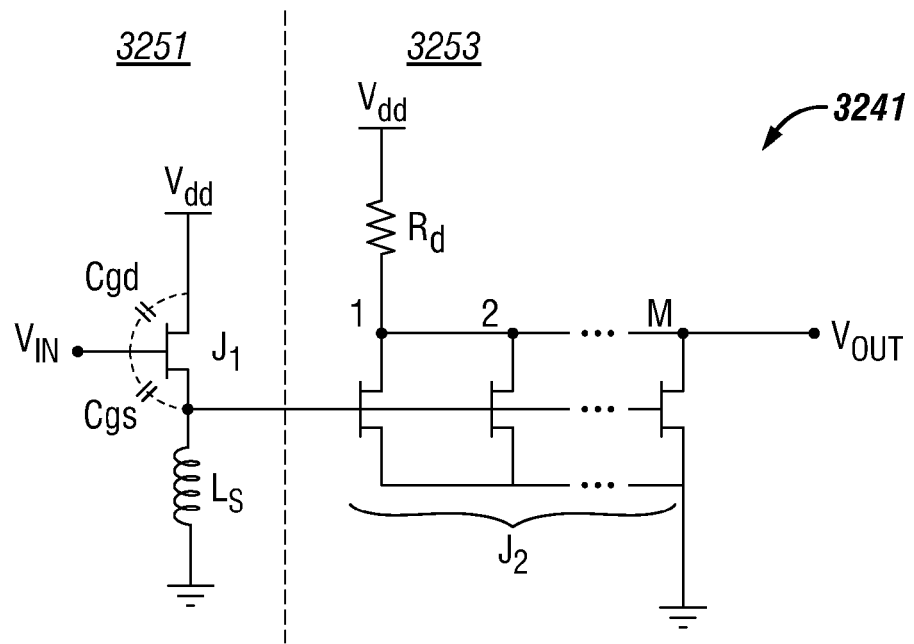
FIG. 32D shows a preamplifier in accordance with one embodiment of the present disclosure.

FIG. 32D shows another embodiment of a preamplifier 3241 that can be used with the NMR receiver 3206. The preamplifier 3238 of FIG. 32C uses a resistor ($R_s$) at the source of the transistor ($J_1$) to set a DC bias current through the transistor. A negative power supply ($V_{SS}$) is applied at an end of the resistor ($R_S$) because of a DC voltage drop across the resistor. In one specific embodiment, the resistor is 820Ω and the power supply is −5 V. In contrast to the preamplifier 3238 of FIG. 32C, the preamplifier 3241 of FIG. 32D replaces the resistor ($R_S$) with a large inductor ($L_S$) that is coupled to the transistor ($J_1$). In one specific embodiment, the inductor has an inductance of 470 µH. By using such an arrangement, the preamplifier 3241 of FIG. 32D can omit the use of the power supply ($V_{SS}$).

Figure 32E:
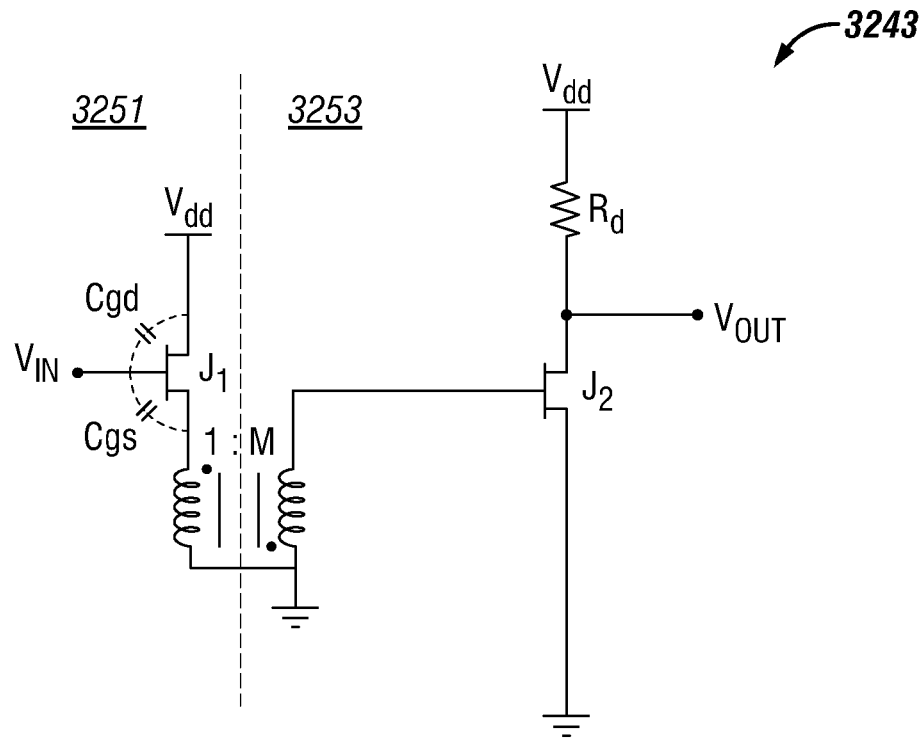
FIG. 32E shows a preamplifier in accordance with another embodiment of the present disclosure.

FIG. 32E shows yet another embodiment of a preamplifier 3243 that can be used with the NMR receiver 3206. In this embodiment, the preamplifier 3243 includes a second transformer that is coupled between the common-drain amplifier stage 3251 and the common-source amplifier stage 3253. The second transformer amplifies the NMR signal by providing a voltage gain to the signal. In some embodiments, the voltage gain provided by the transformer is substantially noiseless. The transformer may be step-up transformer with a turns ratio of 1:M (e.g., between 1:2 and 1:10). In some embodiments, the second transformer includes a magnetic core, while, in other embodiments, a core is not used. If a magnetic core is used, then the transformer may be enclosed with a magnetic shield. The shield prevents the magnetic field of the NMR magnet from penetrating the transformer core.

This second transformer is followed by the common-source amplifier stage 3253. In this specific embodiment, the common-source amplifier stage 3253 includes a single transistor ($J_2$) configured as a common-source amplifier. Other embodiments, however, may include additional transistors. The second transformer reduces the noise contributed by the common-source amplifier stage 3253 to a level that is $1/M^2$ times that contributed by the common drain amplifier stage 3251 (in power units). Thus, the noise contribution of the common-source amplifier stage 3253 and later stages can be made insignificant for relatively small values of M, and, in this manner, the configuration creates a very low-noise preamplifier. For example, in an embodiment where M is 4, the total input-referred noise of the preamplifier is only 6.25% larger than that of the common drain amplifier stage alone. In various embodiments, the preamplifier 3243 also advantageously saves a significant amount of power. In particular, the resistor or the inductor at the transistor ($J_1$) can be omitted because the primary side of the second transformer sets the DC bias point for the transistor ($J_1$) and the secondary side of the transformer does not need to consume DC power.

In various embodiments, the preamplifiers 3238, 3241, 3243 described herein have increased bandwidth (e.g., over 3 MHz for a typical NMR coil of inductance 15 µH), improved settling time, and similar input-referred noise, as compared to conventional preamplifiers. One conventional example of a transformer-coupled preamplifier for low frequency operation (e.g., less than 50 kHz) is the SR-554, which can be obtained from Stanford Research Systems™.

As shown in FIG. 32C, the broadband receiver 3206 includes a DC blocking network 3247 that is disposed after the preamplifier 3238. The DC blocking network 3247 sets an output ($V_{out}$) of the preamplifier 3238 to ground, which maximizes the overall dynamic range of the receiver 3206.

In the specific embodiment of FIG. 32C, the broadband receiver 3206 also includes a feedback network 3245. The feedback network is coupled to the preamplifier 3238 and configured to reduce settling time of the preamplifier. In this case, the feedback network is coupled to an input ($V_{in}$) of the preamplifier 3238 at one end and after the DC blocking network 3247 at the other end. The feedback network 3245 removes unwanted high-frequency resonances between inductive impedance at the NMR coil 3202 and capacitive input impedance ($C_{input}$) at the preamplifier 3238. These resonances are produced by RF pulses that are applied to the coil 3202 by the transmitter 3204 and can adversely affect the settling time of the receiver 3206. To reduce the settling time, without adding noise, the particular feedback network 3245 shown in FIG. 32C uses an op-amp based integrator circuit followed by a small feedback capacitor ($C_f$). The feedback network 3245 produces a noiseless damping resistance ($R_{damp}$) between the input of the preamplifier ($V_{in}$) and ground to remove these resonances. The noiseless damping resistance ($R_{damp}$) can be defined by:

$$R_{damp} = \tau/(AC_f) \qquad \text{Eq. 34}$$

where $\tau = R_1 C_1$ is the time constant of the integrator circuit, and A is the overall voltage gain of the preamplifier. Other types of feedback networks can also be used. For example, a feedback resistor ($R_f$) can replace the capacitor ($C_f$) and a voltage gain circuit can replace the integrator circuit.

In various embodiments, the settling time of the receiver can be further improved by limiting the signal amplitude at various locations within the receiver 3206 using diode clamps. In the embodiment shown in FIG. 32C, a diode clamp 3249 is coupled between the transformer 3236 and the input ($V_{in}$) of the preamplifier 3238 (e.g., at the gate of the transistor (J1)). The diode clamp 3249 includes a pair of cross-coupled diodes that limit maximum signal amplitude across the diodes to approximately a threshold voltage of each diode ($V_{on}$). Typical values of the threshold voltage ($V_{on}$) for silicon diodes range from 0.6 V to 0.7 V. Similar diode clamps can also be used at other locations within the receiver 3206, such as after the output ($V_{out}$) of the preamplifier and/or between the common-drain stage (J1) and common-source stage (J2).

The broadband NMR electronics 3204, 3206, 3208 also include a spectrometer 3208. In some embodiments, the output of the preamplifier 3238 is passed through further stages of analog filtering before being sent to the spectrometer 3208. For example, high-pass and low-pass filters can set the minimum and maximum detectable NMR frequency, respectively. The cutoff frequencies of these filters can be varied based on the application.

In some embodiments, the detected resonant signal is output by the broadband receiver 3238 in analog form. In such embodiments, the spectrometer 3208 may include a digitizer 3240 for converting the detected resonant signal into digital data. Furthermore, in various embodiments, demodulation of the NMR signal can occur within the spectrometer 3208. In various other or alternative embodiments, however, demodulation of the NMR signal can also occur within the broadband NMR receiver 3206. The spectrometer 3208 also includes a post-processor 3242 that is used to interpret the detected digital resonant data and to determine NMR properties from the detected data. This data can be presented to a user using an operator module 3244 with a graphical user interface (GUI). In various embodiments of the present disclosure, the operator interface 3244 and the GUI are not part of the broadband NMR electronics 3204, 3206, 3208. The spectrometer 3208 also includes a pulse sequence generator 3246. The pulse sequence generator 3246 generates NMR sequences based upon parameters selected by an operator at the operator module 3244. The pulse sequence generator 3246 provides the sequences to the transmitter 3204. In one particular embodiment, the spectrometer 3208 is a Kea™, which can be obtained from Magritek™. The spectrometer 3208 can be controlled from the operator module 3244 using Prospa™ software, which can also be obtained from Magritek™.

Further details of broadband NMR electronics (e.g., non-resonant NMR systems) are described in U.S. Publication No. 2012/0001629 published on Jan. 5, 2012.

FIG. 33 shows a broadband NMR system 3300 for applying multi-segment sequences to a substance 3302 in accordance with one embodiment of the present disclosure. The system 3300 includes an NMR module 3304. In various embodiments, the NMR module 3304 includes an electromagnetic device 3306 for applying a static magnetic field to the substance 3302. In some embodiments, the electromagnetic device 3306 is a magnet or an array of magnets. The magnets can be formed from a samarium-cobalt (SmCo) magnetic material.

The NMR module 3304 also includes at least one coil (e.g., antenna) 3308 and broadband NMR electronics 3310 electronically coupled to the coil. The coil 3308 and broadband NMR electronics 3310 apply an oscillating field to the substance 3302 (e.g., a radio frequency (RF) field). In accordance with exemplary embodiments of the present disclosure, the oscillating field applied to the substance includes a multi-segment sequence, such as a sequence with interposed pulse sequence segments. The coil 3308 and broadband NMR electronics 3310 are also used to detect resonant signal that originate within the substance 3302.

The broadband NMR electronics 3310 are electronically coupled to a processor 3312 and a memory 3314 (e.g., a computer system). The memory 3314 can be used to store computer instructions (e.g., computer program code) that are interpreted and executed by the processor 3312. The memory 3314 may be a digital memory such as a random-access memory, a flash drive, a hard drive, or a disc drive.

In alternative or additional embodiments, the multi-segment sequences described herein may be implemented as a series of computer instructions fixed either on a non-transitory tangible medium, such as a computer readable medium (e.g., a diskette, CD-ROM, ROM, field-programmable array (FPGA) or fixed disk) or transmittable to a computer system, via a modem or other interface device, such as a communications adapter connected to a network over a tangible medium (e.g., optical or analog communications lines). The series of computer instructions can embody all or part of the multi-segment sequences described herein.

The multi-segment sequences described herein and various other NMR pulse sequences may be stored within the memory 3314 as software or firmware. The processor 3312 may be configured to retrieve the sequences from memory 3314 and provide instructions to the broadband NMR electronics 3310 to apply the sequences to the substance 3302. The detected resonant signals may also be communicated from the broadband electronics 3310 to the processor 3312 for storage on the memory 3314.

The processor 3312 is also electronically coupled to a communications module 3316. The communications module 3316 communicates with an operator module 3318. The operator module 3318 also includes a communications module 3320 so that the operator module 3318 can communicate with the NMR module 3304. A communications link 3322 between the operator module 3318 and the NMR module 3304 can be established using, for example, a hard-wired link, an optical link, acoustic link, and/or a wireless link. The operator module 3318 includes a processor 3324 and a memory 3326 (e.g., a computer system). The processor 3324 and memory 3326 support a graphical user interface (GUI) 3328, such as a monitor, a touch screen, a mouse, a keyboard and/or a joystick. The GUI 3328 allows an operator to control and communicate with the NMR module 3304. The processor 3324 is also electronically coupled to one or more information input devices 3330. In some embodiments, the input device 3330 is a port for communicating with a removable medium (e.g., a diskette, CD-ROM, ROM, USB and/or fixed disk). In additional or alternative embodiments, the input device 3330 is a modem and/or other interface device that is in communication with a computer network (e.g., Internet and/or LAN). In various embodiments, the NMR module 3304 and the operator module 3318 can be used to perform functions selected from the following non-limiting list:

Communicate instructions to the NMR module 3304 to initiate and/or terminate NMR measurements;
Communicate instructions to change parameters of NMR sequences to the NMR module 3304 (e.g., pulse amplitude of sequences, pulse lengths, timing between pulses, shape of pulses, and/or frequency of pulses);
Communicate detected NMR signal data from the NMR module 3304 to the operator module 3318;
Communicate NMR pulse sequences from the operator module 3318 to the NMR module 3304;
Perform analysis of detected NMR signal data to determine NMR properties of substances at the operator module 3318 and/or the NMR module 3304;
Display various plots of NMR properties to the operator at the operator module 3318; and
Download NMR pulse sequences from the operator module 3318 to the NMR module 3304.

Illustrative embodiments of the present disclosure are not limited to the system shown 3300 in FIG. 33. Various modifications can be made to the system 3300. For example, in one specific embodiment, the NMR module 3304 lacks the processor 3312 and the memory 3314. In such an embodiment, the processor 3324 and memory 3326 on the operator side 3318 support the broadband NMR electronics 3310. Furthermore, in some embodiments, the NMR module 3304 and the operator module 3318 can be physically located in two separate locations. For example, in a borehole application, the NMR module 3304 can be located downhole, while the operator module 3318 is located at the surface. In various other embodiments, the NMR module 3304 and the operator module 3318 can be physically located in the same place as a single system. This may be the case when the system is used in a surface environment such as a laboratory.

Figure 34:
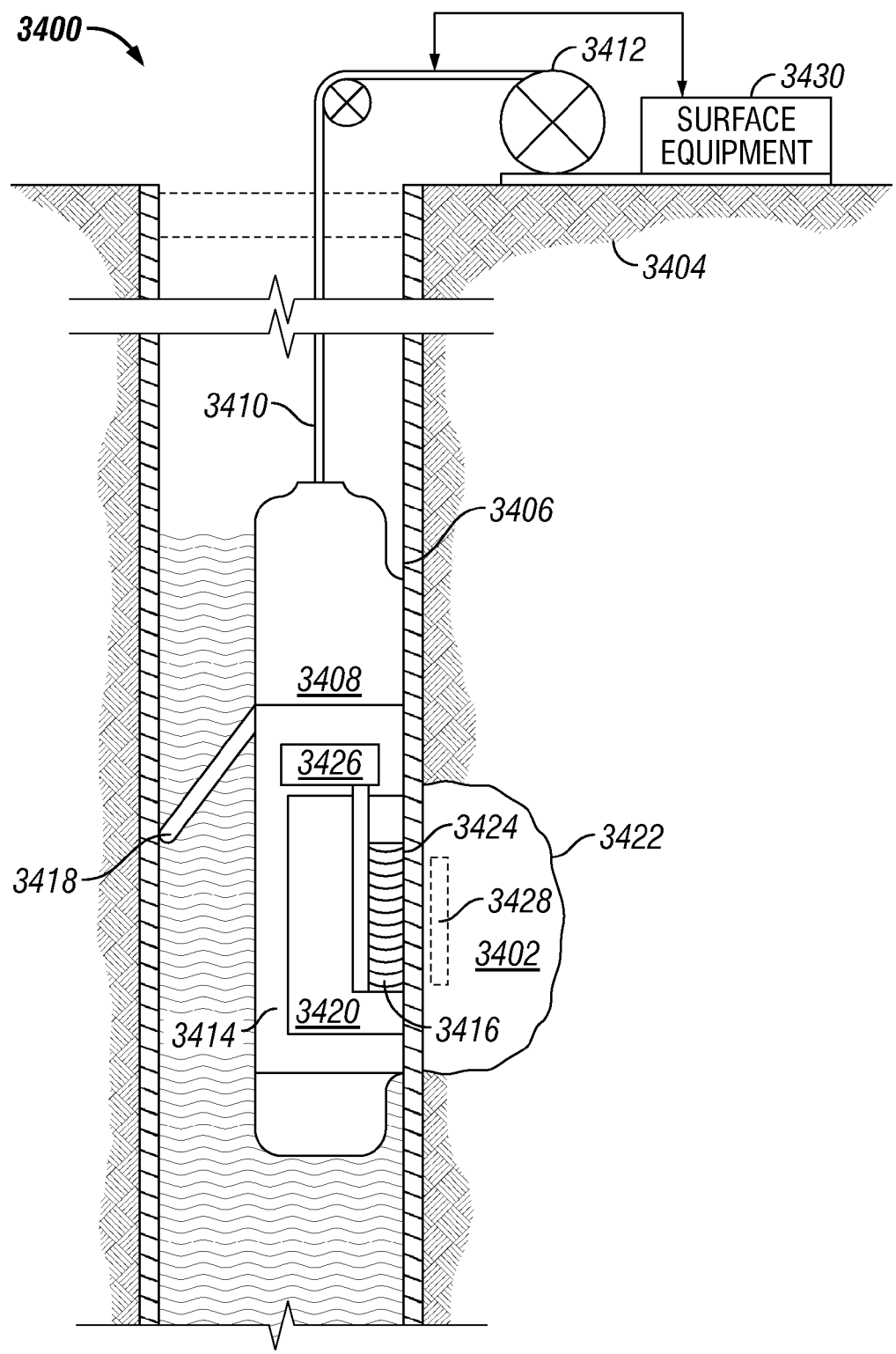
FIG. 34 shows a wireline system for applying multi-segment sequences to a substance in accordance with one embodiment of the present disclosure.

Illustrative embodiments of the present disclosure are further directed to oil and gas field applications. FIG. 34 shows a wireline system 3400 for applying multi-segment sequences to a substance 3402 in accordance with one embodiment of the present disclosure. The wireline system 3400 is used to investigate, in situ, a substance 3402 within an earth formation 3404 surrounding a borehole 3406 to determine a characteristic of the substance (e.g., characteristics of solids and liquids within the earth formation). As shown in FIG. 34, a wireline tool 3408 is disposed within the borehole 3406 and suspended on an armored cable 3410. A length of the cable 3410 determines the depth of the wireline tool 3408 within the borehole 3406. The length of cable is controlled by a mechanism at the surface, such as a drum and winch system 3412. Although the wireline tool 3408 is shown as a single body in FIG. 34, the tool may alternatively include separate bodies.

As shown in FIG. 34, the wireline tool 3408 includes an NMR logging module 3414 that is used to apply multi-segment sequences. The NMR logging module 3414 includes a face 3416 that is shaped to contact the borehole wall 3406 with minimal gaps or standoff. In some embodiments, a retractable arm 3418 is used to press the body of the wireline tool 3408 and the face 3416 against the borehole wall 3406. The NMR logging module 3414 also includes an electro-magnetic device 3420 for applying a static magnetic field to a sensitivity zone 3422 within the earth formation 3404. As explained above, in some embodiments, the electro-magnetic device 3420 is a magnet or an array of magnets formed from a magnetic material.

The NMR logging module 3414 also includes at least one coil 3424 and broadband NMR electronics 3426 electronically coupled to the coil. The coil 3424 and broadband NMR electronics 3426 apply an oscillating field to an area of interest 3428 within the earth formation 3404. The area of interest 3402 is located within the sensitivity zone 3422 of the electro-magnetic device 3420. In accordance with exemplary embodiments of the present disclosure, the oscillating field applied to the earth formation 3404 includes multi-segment sequences, such as the interposed sequences described above. The static magnetic field and oscillating field generate resonant signals within the area of interest 3428. These resonant signals are detected by the coil 3424. The detected resonant signals are used to determine characteristics of the substance 3402 within the area of interest 3428.

The wireline system 3400 includes surface equipment 3430 for supporting the wireline tool 3408 within the borehole 3406. In various embodiments, the surface equipment 3430 includes a power supply for providing electrical power to the wireline tool 3408. The surface equipment 3430 also includes an operator interface for communicating with the NMR logging module 3414. Such an operator interface has already been described with reference to FIG. 33. In some embodiments, the NMR logging module 3414 and operator module communicate through the armored cable 3410.

Figure 35:
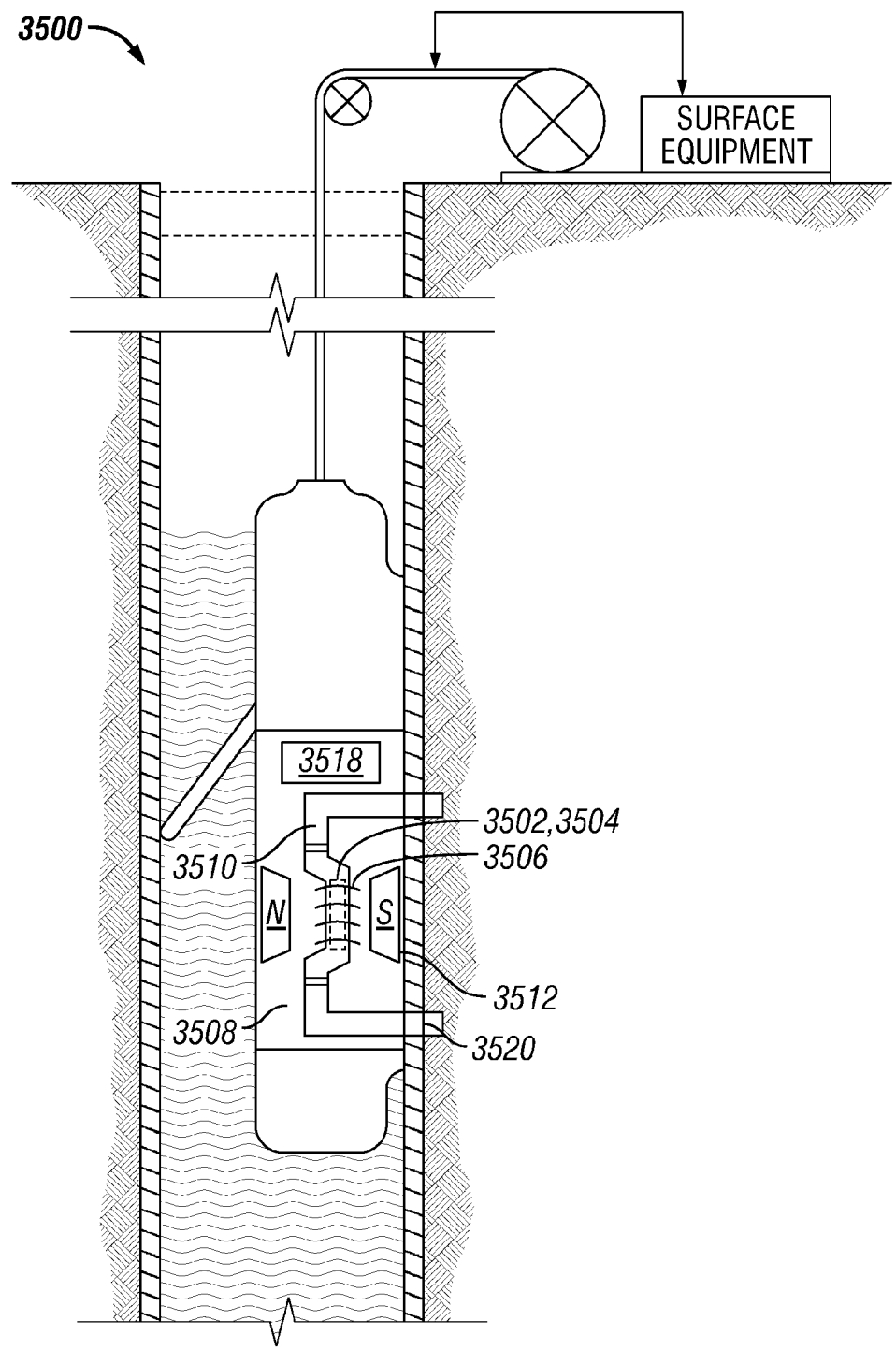
FIG. 35 shows another wireline system for applying multi-segment sequences to a substance in accordance with one embodiment of the present disclosure.

FIG. 35 shows another wireline system 3500 for applying multi-segment sequences to a substance 3502 in accordance with one embodiment of the present disclosure. In contrast to FIG. 34, which shows an embodiment where the area of interest 3428 is outside of the coil 3424, FIG. 35 shows an illustrative embodiment where the coil 3506 is used to analyze substances located within the coil. To this end, the wireline system 3500 includes a flow line NMR module 3508. The flow line NMR module 3508 includes a flow line (or chamber) 3510 that is at least partially disposed within the coil 3506. The area of the flow line 3510 disposed within the coil 3506 is defined as an area of interest 3504. An electro-magnetic device 3512, such as a magnet or a coil, can be used to apply a static magnetic field to the area of interest 3504. A probe module 3514 is used to probe an earth formation 3516. A formation fluid is pumped into the flow line 3510 from the probe module 3514. The formation fluid (e.g., substance) flows through the flow line 3510 and into the area of interest 3504 where the formation fluid is analyzed using a multi-segment sequence applied by the coil 3506 and broadband NMR electronics 3518. In an alternative or additional embodiment, the formation fluid is passed to a separate chamber that is disposed within the coil and the formation fluid is analyzed within the separate chamber. Once the analysis is performed, in some embodiments, the formation fluid flows to a pump-out module 3520 that expels the formation fluid from the flow line 3510.

Figure 36:
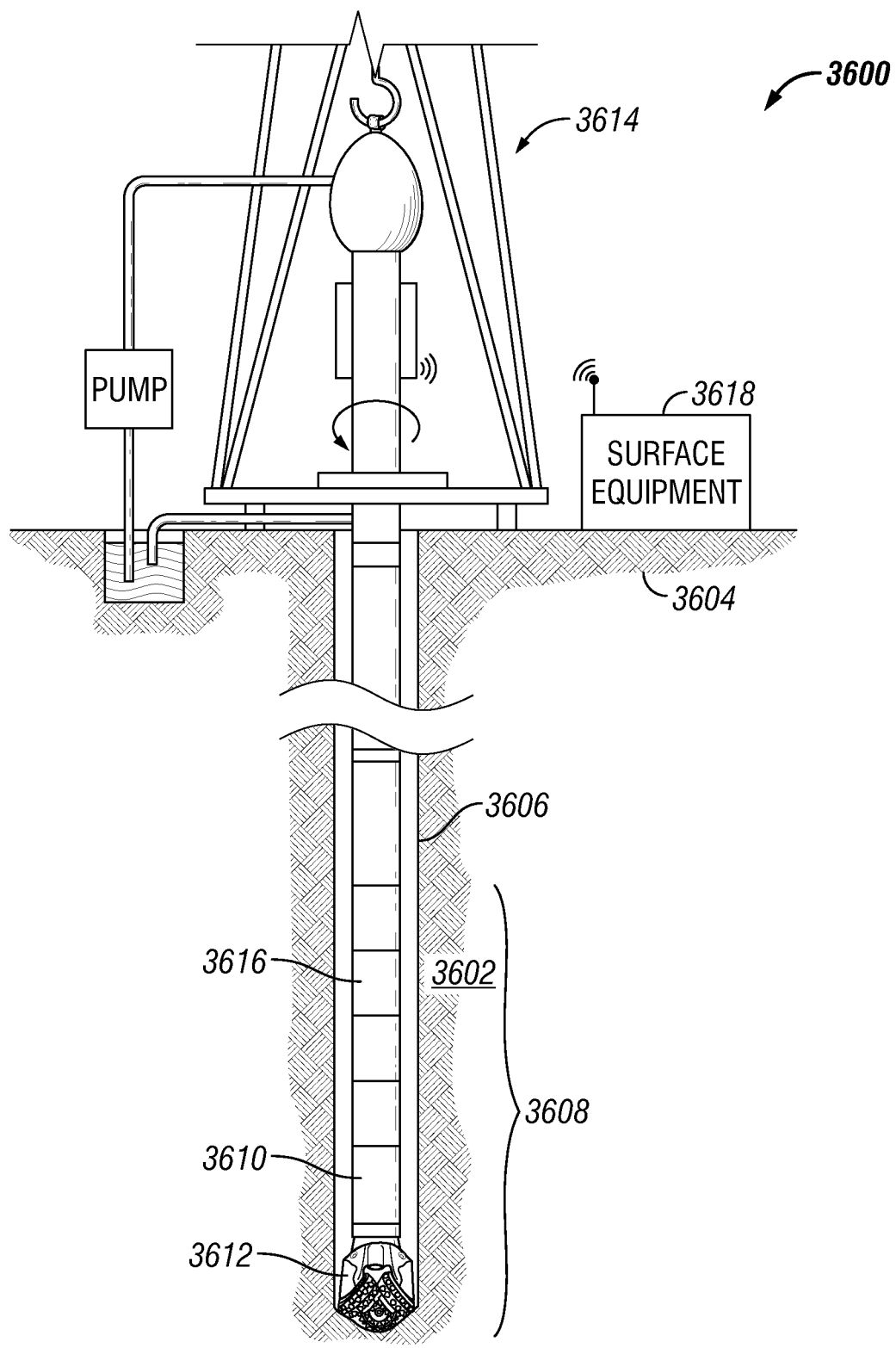
FIG. 36 shows a logging-while-drilling (LWD) system for applying multi-segment sequences to a substance in accordance with one embodiment of the present disclosure.

Illustrative embodiments of the present disclosure can also be applied in logging-while-drilling (LWD) systems. FIG. 36 shows a LWD system 3600 for applying multi-segment sequences to a substance in accordance with one embodiment of the present disclosure. The LWD system 3600 can be used to investigate, in situ, a substance 3602 within an earth formation 3604 surrounding a borehole 3606 to determine a characteristic of the substance, while a drilling operation is performed. The LWD system 3600 includes a drill string 3608 that is suspended within the borehole. The drill string 3608 includes a drill collar 3610 with a drill bit 3612 disposed at the lower-end of the drill collar. The LWD system 3600 also includes a surface system with a derrick assembly and platform assembly 3614 positioned over the borehole 3606. The derrick assembly 3614 rotates the drill string 3608 and, as the drill string rotates, the drill bit 3612 drills deeper into the borehole 3606. An LWD NMR logging module 3616 is disposed within the drill collar 3610 so that the module can log the surrounding earth formation as the drilling operation is performed. The logging module 3616 communicates with surface equipment 3618, which includes an operator interface for communicating with the module. Such an operator interface has already been described with reference to FIG. 33. In various embodiments, the NMR logging module 3616 and operator module can communicate via any one of a wired-drill pipe connection, an acoustic telemetry connection, optical communication and/or electronic communication.

Figure 37:
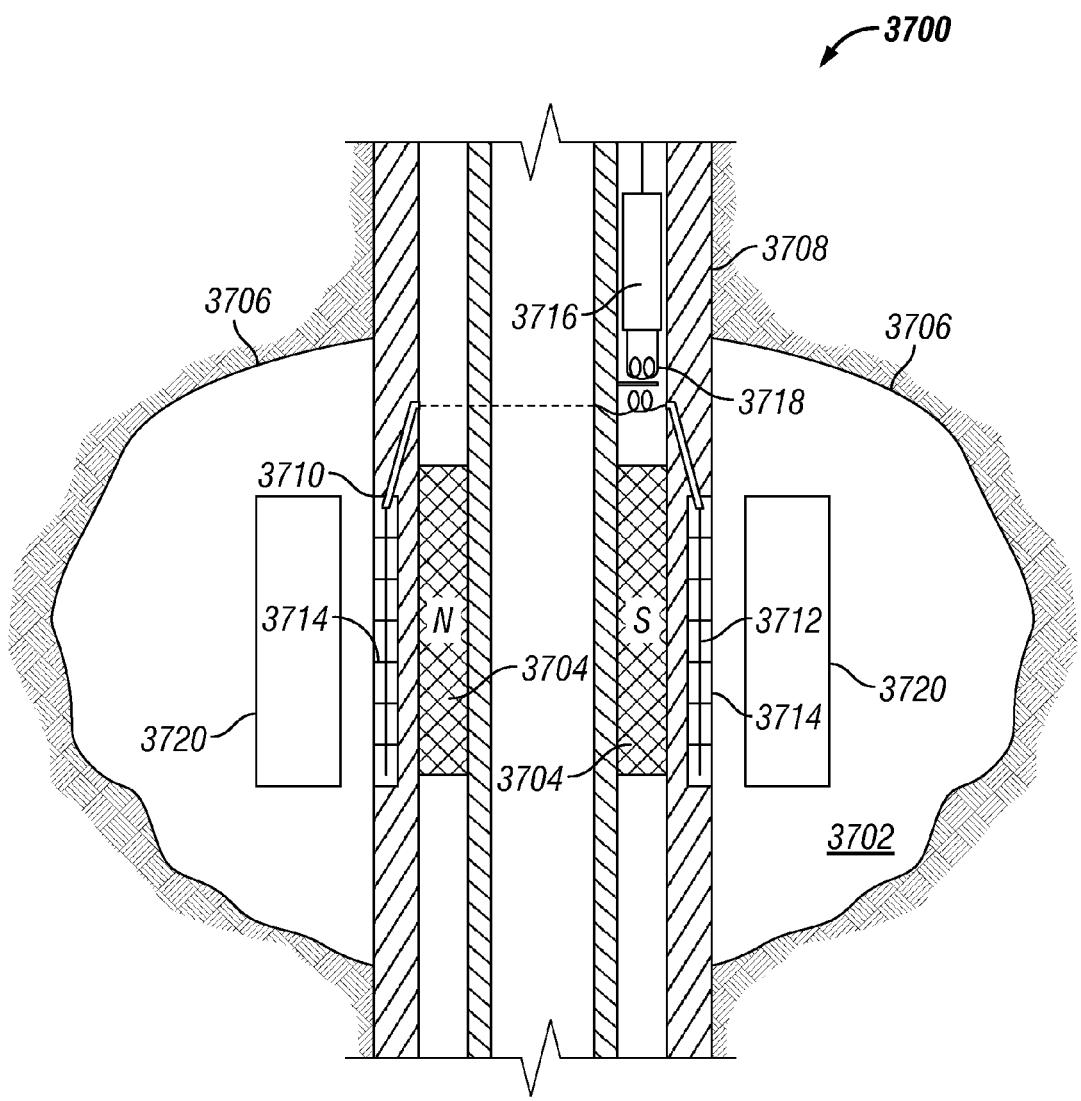
FIG. 37 shows an LWD NMR logging module for applying multi-segment sequences to a substance in accordance with one embodiment of the present disclosure.

FIG. 37 shows an LWD NMR logging module 3700 for applying multi-segment sequences to a substance 3702 in accordance with one embodiment of the present disclosure. The module 3700 includes a cylindrical magnet 3704 that generates a static magnetic field within a zone of sensitivity 3706 within the earth formation. The module 3700 also includes a drill collar 3708 with an axial slot 3710. A coil 3712 is disposed within the slot 3710 and the slot is filled with a ceramic insulator. The slot 3712 is sealed using a cover 3714. In some embodiments, the cover 3714 is formed from a non-magnetic material and/or non-conductive material. The coil 3712 is composed of at least two diametrically opposed conductors. At one end, the conductors are grounded to the drill collar 3708. At the other end, the conductors are coupled to broadband NMR electronics 3716. The broadband NMR electronics 3716 include a transformer and the conductors are coupled to the transformer via, for example, pressure feed-throughs. The transformer 3718 maintains a 180 degree phase difference between the currents in the diametrically opposite conductors. The coil 3712 applies an oscillating magnetic field to an area of interest 3720 within the zone of sensitivity 3706. In some embodiments, the oscillating magnetic field is axially symmetric to facilitate measurements during rotation of the drill string. In accordance with exemplary embodiments of the present disclosure, the oscillating field applied to the earth formation includes multi-segment sequences. In additional or alternative embodiments, the coil 3712 can also be configured so that the drill collar itself 3708 produces the oscillating magnetic field. Further details of NMR LWD systems are described in U.S. Pat. No. 5,629,623, issued on May 13, 1997.

Various embodiments of the present disclosure are not limited to oilfield borehole applications, such as LWD systems and wireline systems. Exemplary embodiments of the present disclosure can also be implemented in surface environments, such as laboratories. Furthermore, illustrative embodiments are not limited to oil and gas field applications. Various embodiments described herein may also have application in chemical production, food production, material inspection and infrastructure inspection (e.g., building and bridges). In one particular embodiment, cheese can be analyzed using multi-segment sequences in order to determine an oil-to-water ratio within the cheese. In the specific example of analyzing cheese, a two-dimensional measurement can be made. The efficiency of such a measurement can be increased using the systems and pulses sequences described above.

Furthermore, the broadband NMR systems and devices described herein, including the transmitter 3214 and the receiver 3206, are not limited to implementing NMR techniques and sequences. The systems and devices described herein can also be used to implement other magnetic resonance (MR) techniques and sequences, such as nuclear quadrupole resonance (NQR) techniques and sequences. For example, the receiver 3206 described herein can be used to process NQR signals that have been obtained from a substance.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

We claim:

1. A method for determining a nuclear magnetic resonance (NMR) property, the method comprising:
   i) applying a static magnetic field to a substance;
   ii) operating NMR transmitter circuitry to apply an NMR pulse sequence to the substance, wherein the NMR pulse sequence includes at least one pulse sequence segment applied at a first frequency and at least one other pulse sequence segment applied at a second frequency offset from the first frequency, wherein the at least one pulse sequence segment applied at the first frequency generates at least one resonant signal within a first area of interest in the substance, and wherein the at least one other pulse sequence segment applied at the second frequency generates at least one other resonant signal within a second area of interest in the substance that is offset from the first area of interest;
   iii) operating NMR receiver circuitry to detect the at least one resonant signal generated by the at least one pulse sequence segment applied at the first frequency in ii);
   iv) operating the NMR receiver circuitry to detect the at least one other resonant signal generated by the at least one pulse sequence segment applied at the second frequency in ii);
   v) operating a processor to analyze the at least one resonant signal detected in iii) and the at least one other resonant signal detected in iv) to determine an NMR property of the substance for the first and second areas of interest in the substance; and
   vi) operating a display device to display the NMR property of the substance for the first and second areas of interest in the substance.

2. The method according to claim 1, wherein the NMR pulse sequence includes a waiting period between the at least one pulse sequence segment applied at the first frequency and the at least one other pulse sequence segment applied at the second frequency.

3. The method according to claim 1, wherein the NMR transmitter circuitry comprises a non-resonant NMR transmitter circuit.

4. The method according to claim 1, wherein:
   the first and second areas of interest in the substance material are offset in depth into the substance.

5. The method according to claim 1, wherein:
   the at least one pulse sequence segment applied at the first frequency and the at least one other pulse sequence segment applied at the second frequency in ii) are diffusion edit pulse sequences for measuring a molecular diffusion coefficient of the substance at the first and second areas of interest in the substance.

6. The method according to claim 1, wherein:
   the at least one other pulse sequence segment applied at the second frequency is initiated before the first area of interest in the substance reaches a point of thermal equilibrium.

7. The method according to claim 1, wherein:
   the at least one pulse sequence segment applied at the first frequency and the at least one other pulse sequence segment applied at the second frequency are interleaved with one another in ii) to avoid interaction between the first and second areas of interest in the substance.

8. The method according to claim 1, wherein:
   parts of the at least one pulse sequence segment applied at the first frequency are interposed with corresponding parts of the at least one other pulse sequence segment applied at the second frequency in ii).

9. The method according to claim 8, wherein:
   the interposed parts of the at least one pulse sequence segment applied at the first frequency and the at least one other pulse sequence segment applied at the second frequency include an excitation pulse and a series of refocusing pulses.

10. The method according to claim 8, wherein:
   the NMR transmitter circuitry is configured to modulate phase or timing of interposed excitation pulses that are part of the at least one pulse sequence segment applied at the first frequency and the at least one other pulse sequence segment applied at the second frequency.

11. The method according to claim 10, wherein:
the modulation of phase or time of the interposed excitation pulses is configured to compensate for Bloch-Siegert phase shift.

12. The method according to claim 1, wherein:
the NMR property of the substance is selected from the group consisting of a $T_1$ relaxation time, a $T_2$ relation time, a diffusion property, and correlation function of such properties.

13. The method according to claim 1, wherein:
the method is performed by a downhole logging tool, the substance comprises a formation disposed adjacent the downhole logging tool, and the first and second areas of interest are offset radially from the downhole logging tool.

14. A method for determining a nuclear magnetic resonance (NMR) property, the method comprising:
i) applying a static magnetic field to a substance;
ii) operating NMR transmitter circuitry to apply an NMR pulse sequence to the substance, wherein the NMR pulse sequence includes at least one pulse sequence segment applied at a first frequency and at least one other pulse sequence segment applied at a second frequency offset from the first frequency, wherein the at least one pulse sequence segment applied at the first frequency generates at least one resonant signal within a first area of interest in the substance, wherein the at least one other pulse sequence segment applied at the second frequency generates at least one other resonant signal within a second area of interest in the substance that is offset from the first area of interest, and wherein the at least one resonant signal generated by the at least one pulse sequence segment applied at the first frequency influences a particular component of the at least one other resonant signal generated by the at least one other pulse sequence segment applied at the second frequency;
iii) operating NMR receiver circuitry to detect the particular component of the at least one other resonant signal generated by the at least one pulse sequence segment applied at the second frequency in ii);
iv) operating a processor to analyze the particular component of the at least one other resonant signal detected in iii) to determine an NMR property of the substance; and
v) operating a display device to display the NMR property of the substance.

15. The method according to claim 14, wherein:
the NMR transmitter circuitry is configured to modulate the influence of the least one resonant signal generated by the at least one pulse sequence segment applied at the first frequency on the particular component of the at least one other resonant signal.

16. The method according to claim 15, wherein:
the modulation of the influence of the least one resonant signal is controlled by varying a frequency difference and/or waiting period between the at least one pulse sequence segment applied at the first frequency and the at least one other pulse sequence segment applied at the second frequency.

17. The method according to claim 14, wherein:
the least one resonant signal generated by the at least one pulse sequence segment applied at the first frequency is configured to introduce a non-zero imaginary component in the least one other resonant signal.

18. The method according to claim 17, wherein:
the operation of the NMR receiver circuitry detects the non-zero imaginary component in the least one other resonant signal; and
the operation of the processor analyzes the non-zero imaginary component in the least one other resonant signal to determine the NMR property of the substance.

19. The method according to claim 18, wherein:
the NMR property comprises a $T_1$ relaxation time for the substance.

20. The method according to claim 14, wherein:
the least one resonant signal generated by the at least one pulse sequence segment applied at the first frequency is configured to introduce a phase delay component in the least one other resonant signal.

21. The method according to claim 20, wherein:
the operation of the NMR receiver circuitry detects the phase delay component in the least one other resonant signal; and
the operation of the processor analyzes the phase delay component in the least one other resonant signal to determine the NMR property of the substance.

22. The method according to claim 21, wherein:
the NMR property comprises a magnitude of an applied oscillating field.

23. The method according to claim 14, wherein the NMR transmitter circuitry comprises a non-resonant NMR transmitter circuit.

24. The method according to claim 14, wherein:
the method is performed by a downhole logging tool, the substance comprises a formation disposed adjacent the downhole logging tool, and the first and second areas of interest are offset radially from downhole logging tool.

* * * * *